US008481271B2

(12) United States Patent
Galon et al.

(10) Patent No.: US 8,481,271 B2
(45) Date of Patent: Jul. 9, 2013

(54) VITRO METHOD FOR THE PROGNOSIS OF PROGRESSION OF A CANCER AND OF THE OUTCOME IN A PATIENT AND MEANS FOR PERFORMING SAID METHOD

(75) Inventors: Jérôme Galon, Paris (FR); Franck Pages, Boulogne-Billancourt (FR); Wolf-Herman Fridman, Paris (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 1103 days.

(21) Appl. No.: 12/090,832

(22) PCT Filed: Sep. 28, 2006

(86) PCT No.: PCT/IB2006/003168
§ 371 (c)(1),
(2), (4) Date: Oct. 23, 2008

(87) PCT Pub. No.: WO2007/045996
PCT Pub. Date: Apr. 26, 2007

(65) Prior Publication Data
US 2009/0215053 A1 Aug. 27, 2009

Related U.S. Application Data

(60) Provisional application No. 60/764,356, filed on Feb. 2, 2006.

(30) Foreign Application Priority Data

Oct. 19, 2005 (EP) .................................... 05292200

(51) Int. Cl.
*G01N 33/53* (2006.01)
*G01N 33/574* (2006.01)

(52) U.S. Cl.
USPC ......................................... 435/7.1; 435/7.23

(58) Field of Classification Search
None
See application file for complete search history.

(56) References Cited

U.S. PATENT DOCUMENTS

| 5,556,763 | A | 9/1996 | Ochoa et al. ................ 435/7.23 |
| 5,605,805 | A | 2/1997 | Verwer et al. ................ 435/7.24 |
| 5,965,366 | A | 10/1999 | Ochoa et al. ...................... 435/6 |
| 6,656,683 | B1 | 12/2003 | Reuben et al. ..................... 435/6 |
| 2005/0006533 | A1 | 1/2005 | Corjon |
| 2005/0065333 | A1 | 3/2005 | Seth |

FOREIGN PATENT DOCUMENTS

| WO | WO 96/25664 | 8/1996 |
| WO | 03070265 A2 | 8/2003 |
| WO | 2005007186 A1 | 1/2005 |

OTHER PUBLICATIONS

De Gruijl et al (British J of Cancer, 1999, 79:1127-1132, IDS).*
Menon et al (Cancer immunology immunotherapy, 2003, 52:121-126).*
Johnson et al (Lung Cancer, 2000, 27:27-35).*
Takanami et al (Journal of Thoracic and Cardiovascular Surgery, 2001, 121:1058-1063).*
Zola et al; Cellular Immunology, 1992, 145:175-186; abstract Only (2 pages).*
Schumacher et al (Cancer research, 2001, 61:3932-3936).*
Naito et al (Cancer Research, 1998, 58:3491-3494).*
Funada et al (Oncol Rep, 2003, 10:309-313).*
Gao et al (J Clinical oncology, 2007, 25:2586-2593).*
Grabenbauer et al (Clinical Cancer Research, 2006, 12:3355-3360).*
Nakano et al (Cancer Research, 2001, 61:51532-51536).*
Nagtegaal et al (BMC Cancer, 2001, 1:7).*
Tosi et al (Eur J Cancer, 1992, 28A:1365-1370).*
Grabenbauer et al (I.J. Radiation Oncology, Oct. 1, 2005, vol. 63, Supplement, p. S16, abstract #28, IDS).*
Zhang et al (New England J medicine, 2003, 348:203-213, IDS).*
Axdorph et al., "T-cell-rich B-cell lymphoma—diagnostic and therapeutic aspects," *APMIS*, 110:379-390, 2002.
De Gruijl et al., "Expression of CD3-zeta on T-cells in primary cervical carcinoma and in metastasis-positive and -negative pelvic lymph nodes," *Brit. J. Cancer*, 79:1127-1132, 1999.
Diederichsen et al., "Prognostic value of the CD4+/CD8+ ratio of tumour infiltrating lymphocytes in colorectal cancer and HLA-DR expression on tumour cells," *Cancer Immunol. Immunother.*, 52:423-428, 2003.
Drescher and Lynch, "Tumor infiltrating lymphocytes (TILs): Lessons learned in 30 years of study," *Clin. Appl. Immunol. Rev.*, 5:149-166, 2005.
Hahn et al., "Therapeutic outcome of Epstein-Barr Virus Positive T/NK Cell Lymphoma in the Upper Aerodigestive Tract," *Yoneshi Medical Journal*, 43:175-182, 2002.
Ishigami et al., "CD3-zetachain expression of intratumoral lymphocytes is closely related to survival in gastric carcinoma patients," *Cancer*, 94:1437-1442, 2002.
Kuss et al., "Effector CD8+CD45RO-CD27-T cells have signalling defects in patients with squamous cell carcinoma of the head and neck," *Brit. J. Cancer*, 88:223-230, 2003.
Maki et al., "Decreased CD3 ζ molecules of T lymphocytes from patients with hepatocellular carcinoma associated with hepatitis C virus," *Hepatology Res.*, 27:272-278, 2003.
Maki et al., "Decreased expression of CD28 coincides with the downmodulation of CD3ζ and augmentation of caspase-3 activity in T cells from hepatocellular carcinoma-bearing patients and hepatitis C virus-infected patients," *J. Gastroent. Hepatology*, 19:1348-1356, 2004.

(Continued)

*Primary Examiner* — Laura B Goddard
(74) *Attorney, Agent, or Firm* — Whitham, Curtis, Christofferson & Cook, P.C.

(57) ABSTRACT

The present invention relates to the prognosis of the outcome of a cancer in a patient, which prognosis is based on the quantification of one or several biological markers that are indicative of the presence of, or alternatively the level of, the adaptive immune response of said patient against said cancer.

33 Claims, 14 Drawing Sheets

OTHER PUBLICATIONS

Nistico et al., "Host immunosurveillance contributes to the control of erbB-2 overexpression in HLA-A2-breast-cancer patients," *Int J. Cancer*, 84:598-603, 1999.

Oshikiri et al., "Prognostic Value of Intratumoral CD8+ T Lymphocyte in Extrahepatic Bile Duct Carcinoma as Essential Immune Response," *J. Surgical Oncology*, 84:224-228, 2003.

Pages et al., "Effector memory T cells, early metastasis, and survival in colorectal cancer," *N. Engl. J. Med.*, 353:2654-2666, 2005.

Phillips et al., "Tumour-infiltrating lymphocytes in colorectal cancer with microsatellite instability are activated and cytotoxic," *Brit. J. Surgery*, 91:469-475, 2004.

Prado-Garcia et al., "Effector, memory and naïve CD8+ T cells in peripheral blood and pleural effusion from lung adenocarcinoma patients," *Lung Cancer*, 47:361-371, 2005.

Reichert et al., "Signaling abnormalities, apoptosis, and reduced proliferation of circulating and tumor-infiltrating lymphocytes in patients with oral carcinoma," *Clin. Cancer Res.*, 8:3137-3145, 2002.

Tan et al., "Cutaneous lymphomas other than mycosis fungoides in Singapore: a clinicopathological analysis using recent classification systems," *Brit. J. Dermatology*, 149:542-553, 2003.

Valmori et al., "Circulating Tumor-reactive CD8(+) T cells in melanoma patients contain a CD45RA(+)CCR7(−) effector subset exerting ex vivo tumor-specific cytolytic activity," *Cancer Res.*, 62:1743-1750, 2002.

Zhang et al., "Intratumoral T Cells, Recurrence, and Survival in Epithelial Ovarian Cancer," *N. Engl. J. Med.*, 348:203-213, 2003.

Kuppner, M.C., et al., "Activation and adhesion molecule expression on lymphoid infiltrates in human glioblastomas." Journal of Neuroimmunology, 29 (1990) 229-238.

Ryschich, E., et al., "Control of T-Cell-Mediated Immune Response by HLA Class I in Human Pancreatic Carcinoma." Clinical Cancer Research, vol. 11, 498-504, Jan. 15, 2005.

Nagetaal, I. D., et al., "Local and distant recurreces in rectal cancer patients are predicted by the nonspecific immune response; specific immune response has only a systemic effect-a histopathological and immunohistochemical study." BMC Cancer. Jul. 16, 2001. 1:7. 11 pages.

Ryschich, E., et al., "Expression of HLA class I/II antigens and T cell immune response in human neuroendocrine tumors of the pancreas." Tissue Antigens. 2003: 62: 48-54.

Tomasini, D., et al., "Pityriasis lichenoides: a cytotoxic T-cell-mediated skin disorder. Evidence of human parvovirus B19 DNA in nine cases," Journal of Cutaneous Pathology, F Cutan Pathol 2004: 31: 531-538.

Katsura, Y., et al., "cytotoxic T-Cell Lymphoma Arising in Behcet Disease," International Journal of Hematology, Nov. 27, 2002. 282-285.

Galon, J., et al., "Type, Density, and Location of Immune Cells Within Human Colorectal Tumors Predict Clinical Outcome," Science, vol. 313. Sep. 29, 2006. 1960-1964.

Abbasciano et al. "Coagulation Disorders and Tumor Markers in the Diagnosis of Pancreatic Cancer", Oncology, Jan. 1, 1991, pp. 377-382, vol. 48.

Ahmed et al. "Alpha-V Beta-6 Integrin-A Marker for the Malignant Potential of Epithelial Ovarian Cancer", J Histochem Cytochem, Oct. 1, 2002, pp. 1371-1379, vol. 50, No. 10.

Banerjea et al. "Colorectal cancers with microsatellite instability display mRNA expression signatures characteristic of increased immunogenicity", Molecular Cancer, Aug. 6, 2004, pp. 1476-5498, vol. 3, No. 1, Biomed Central, London.

Collins et al. "Prospective Identification of Tumorigenic Prostate Cancer Stem Cells", Cancer Res, Jan. 1, 2005, pp. 10946-10951, vol. 65, No. 23.

Cozar et al. "Analysis of NK cells and chemokine receptors in tumor infiltrating CD4 T lymphocytes in human renal carcinomas", Cancer Immunol Immunother, Sep. 1, 2005, pp. 858-866, vol. 54, No. 9, Springer, Berlin.

Cresswell et al. "Distribution of lymphocytes of the Alpha-E and Beta-7 phenotype and E-cadherin in normal human urotherlium and bladder carcinomas", Clin Exp Immunol, Jan. 1, 2001.

Demeure et al. "T Lymphocytes infiltrating various tumor types express the MHC class II ligand lymphocyte activation gene-3 (LAG-3): role of LAG-3/MHC class interations in cell-cell contacts", European Journal of Cancer, Sep. 1, 2001, pp. 1709-1718, vol. 37, No. 13, Pergamon Press, Oxford.

Di Carlo et al. "Immunological mechanisms elicited at the tumor site by lymphocyte activation gene-3 (LAG-3) versus IL-12: Sharing a common Th1 anti-tumor immune pathway", Journal of Pathology, Jan. 1, 2005, pp. 82-91, vol. 205, No. 1, John Wiley & Sons Ltd, GB.

Diloretto et al. "Normal, Adjacent and Tumor Tissue Renin Levels in Carcinoma Tissues of the Kidney", Kidney International, Dec. 1, 1977, p. 498, vol. 12, No. 6, London.

Doherty et al. "Interferon Regulatory Factor Expression in Human Breast Cancer", Annals of Surgery, May 2001, pp. 623-629, vol. 233, No. 5.

Florek et al. "Prominin-1/CD133, a neural and hematopoietic stem cell marker, is expressed in adult human differentiated cells and certain types of kidney cancer", Cell Tissue Res, Jan. 1, 2005, pp. 15-26, vol. 319, No. 1, Berlin.

Gruber et al. "Correlation between the tumoral expression of Beta3-integrin and outcome in cervical cancer patients who had undergone radiotherapy", British Journal of Cancer, Dec. 14, 2004, pp. 41-46, vol. 92, No. 1.

Hilbe et al. "CD133 postitive endothelial progenitor cells contribute to the tumor vasculature in non-small cell lung cancer", J Clin Path, Sep. 1, 2004, pp. 965-969, vol. 57, No. 9.

Kato et al. "Expression of IL-17 mRNA in Ovarian Cancer", Biochemical and Biophysical Research Communications, Apr. 1, 2001, pp. 735-738, vol. 282, No. 3.

Kayed et al. "Indian Hedgehog Signalling Pathway: Expression and Regulation in Pancreatic Cancer", Int. J. Cancer, Jan. 1, 2004, pp. 668-676, vol. 110, No. 5.

Kim et al. "The Significance of Granzyme B Expression in Patients with Angiocentric Lymphoma of the Head and Neck", Cancer, Jun. 15, 2001, pp. 2343-2352, vol. 91, No. 12.

Grabenbaur et al. "Tumor Infiltrating T-cells Determine Outcome in Anal Carcinoma", I. J. Radiation Oncology, Oct. 1, 2005, p. S16, vol. 63, No. 2.

Kishi et al. "An Impaired Expression of Granulysin on NK Cells in Cancer Patients", Journal of Interferon and Cytokine Research, Oct. 1, 2001, pp. S109-S110, vol. 21, No. Suppl. 1, Mary Ann Lieber, New York.

Kothapalli et al. "Identification of Differentially Expressed Genes in Large Granular Lymphocyte Leukemia", Experimental Hematology, Jan. 1, 2000.

Kuniyasu et al. "Relative Expression of Type IV Collagenase, E-cadherin, and Vascular Endothelial Growth Factor/Vascular Permeability Factor in Prostatectomy Specimens Distinguishes Organ-confined from Pathologically Advance Prostate Cancers", Clinical Cancer Research, Jan. 1, 2001.

Kunz et al. "Strong Expression of the Lymphoattractant C-X-C Chemokine Mig is Associated With Heavy Infiltration of T Cells in Human Malignant Melinoma", Journal of Pathology.

Liu et al. "Chemokine receptors support infiltration of lymphocyte subpopulations in human hepatocellular carcinoma", Clinical Immunology, Feb. 1, 2005, pp. 174-182, vol. 114, No. 2, Academic Press.

Lobo et al. "The Immune Environment in Human Endometrium during the Window of Implantation", American Journal of Reproductive Immunology, Oct. 2004, pp. 244-251, vol. 52, No. 4.

Lowney et al. "Interferon Regulatory Factor-1 and -2 in Human Melanoma Specimens", Annals of Surgical Oncology, Sep. 1, 1999, pp. 604-608, vol. 6, No. 6.

Luboshits et al. "Elevated Expression of the CC Chemokine Regulated on Activation, Normal T Cell Expressed and Secreted (RANTES) in Advanced Breast Carcinoma", Cancer Research, Sep. 15, 1999, pp. 4681-4687, vol. 59, No. 18, American Association for Cancer Research, US.

Marth et al. "Interferon-Gamma expression is an independent prognostic factor in ovarian cancer", American Journal of Obstetrics and Gynecology, Nov. 1, 2004, pp. 1598-1605, vol. 191, No. 5, St. Louis.

Moran et al. "RANTES Expression Is a Prediction of Survival in Stage I Lung Adenocarcinoma", Clinical Cancer Research, Dec. 1, 2002, pp. 3803-3812, vol. 8, No. 12, The American Association for Cancer Research, US.

Nakashima et al. "Expression of vascular endothelial growth factor-A and vascular endothelial growth factor-C as prognostic factors for non-small cell lung cancer", Med Sci Monit, Jan. 1, 2004.

Niwa et al. "Correlation of Tissue and Plasma RANTES Levels with Disease Course in Patients with Breast and Cervical Cancer", Clinical Cancer Research, Feb. 1, 2001, pp. 285-289, vol. 7, No. 2.

Obermair et al. "Influence of Microvessel Density and Vascular Permeability Factor/Vascular Endothelial Growth Factor Expression on Prognosis in Vulvar Cancer", Gynegologic Oncology, Jan. 1, 1996.

Ohshima et al. "Expression of Chemokine Receptor CXCR3 and its Ligand, Mig, in Gastric and Thyroid Marginal Zone Lymphomas. Possible Migration and Autocrine Mechanism", Leukemia and Lymphoma, Feb. 1, 2003, pp. 329-336, vol. 44, No. 2.

Prigent et al. "Lymphocyte activation gene-3 induces tumor regression and antitumor immune responses", Eur. J. Immunol., Dec. 1, 1999, pp. 3867-3876, vol. 29, No. 12, Wiley—V. C. H. Verlag GmbH & Co., Germany.

Ropponen et al. "Prognostic Value of Tumor-Infiltrating Lymphocytes (TILs) in Colorectal Cancer", Journal of Pathology, 1997, pp. 318-324, vol. 182, No. 3.

Schumacher et al. "Prognostic Significance of Activated CD8+ T Cell Infiltrations within Esophageal Carcinomas", Cancer Research, May 15, 2001, pp. 3932-3936, vol. 61, No. 10.

Smith et al. "Expression of B-cell-attracting chemokine 1 (CXCL13) by malignant lymphocytes and vascular endothelium in primary central nervous system lymphoma", Blood Journal, Oct. 3, 2002, pp. 815-821, vol. 101, No. 3.

Steffens et al. "Renin-producing renal cell carcinomas—clinical and experimental investigations on a special form of renal hypertension", Urol Res, Feb. 1, 1992, pp. 111-115, vol. 20, No. 2.

Steffens et al. "Renin producing renal cell carcinoma", Eur Urol, Jan. 1, 1990, pp. 56-60, vol. 18, No. 1.

Steiner et al. "Funtion of pro-inflammatory interleukin IL-17", Eur Urol, Feb. 1, 2004, p. 19, vol. 3, No. 2.

Steiner et al. "Expression and Function of Pro-Inflammatory Interleukin IL-17 and IL-17 Receptor in Normal, Benign Hyperplastic, and Malignant Prostate", The Prostate, Aug. 1, 2003, pp. 171-182, vol. 56, No. 3, Wiley-Liss, New York.

Suzuki et al. "Mature dendritic cells make clusters with T cells in the invasive margin of colorectal cancer", The Journal of Pathology, Jan. 1, 2001, pp. 37-43, vol. 196, No. 1.

Tanaka et al. "Constitutive Up-Regulation of Integrin-mediated Adhesion of Tumor-infiltrating Lymphocytes to Osteoblasts and Bone Marrow-derived Stromal Cells", Cancer Research, Sep. 15, 1998, vol. 58, No. 18, American Association for Cancer Research, US.

Tartour et al. "Prognostic Value of Intratumoral Interferon Gamma Messenger RNA Expression in Invasive Cervical Carcinomas", Jan. 1, 1998.

Teruya-Feldstein, et al. "The Role of Mig, the Monokine Induced by Interferon-Gamma, and IP-10, the Interferon-Gamma-Inducible Protein-10, in Tissue Necrosis and Vascular Damage Associated with Epstein-Barr Virus-Positive Lymphoproliferative Disease", Blood Journal, Jan. 1, 1997.

Triebel et al. "A soluble lymphocyte activation gene-3 (sLAG-3) protein as a prognostic factor in human breast cancer expressing estrogene or progesterone receptors", Cancer Letters, Jun. 8, 2005, pp. 147-153, vol. 235, No. 1, New York.

Vaquero et al. "Expression and Significance of Vascular Permeability Factor in Tumour Infiltrating Lymphocytes of Brain Metastases", Jan. 1, 2001.

Weng et al. "Differential expression of cxci9(MIG), CXCL10(IP-10) and CXCR3 during adoptive immunotherapy", Proceedings of the American Association for Cancer Research, Jan. 1, 1999.

Xiao-Yan et al. "Relationship between dendritic cells and memory T lymphocytes in tumor site and prognosis of hepatocellular carcinoma", Database Medline, Mar. 16, 2005, pp. 671-675, vol. 85, No. 10, US National Library of Medicine, Bethesda.

Yoshino et al. "Therapeutic Implications of interferon regulatory factor (IRF)-1 and IRF-2 in diffusely infiltrating astrocytomas (DIA): response to interferon (IFN)-Beta in glioblastoma cells and prognostic value for DIA", Journal of Neuro-Oncology, Sep. 1, 2005, pp. 249-260, vol. 74, No. 3, Kluwer Academic Publishers, Bo.

Zeller et al. "Expression of the Adhesion Molecules CD49d and CD49e on G-CSF-Mobilized CD34+ Cells of Patients with Solid Tumors or Non-Hodgkin's and Hodgkin's Lymphoma and of Healthy Donors is Inversely Correlated with the Amount of Mobilized CD34+ Cells", Jan. 1, 1999.

Nijman et al, "T cell infiltration and MHC I and II expression in the presence of tumor antigens: An immunohistochemical study in patients with serious epithelial ovarian cancer", European Journal of Obstetrics & Gynecology, 2001, pp. 114-120, vol. 94, Elsevier Science Ireland Ltd.

\* cited by examiner

VITRO METHOD FOR THE PROGNOSIS OF PROGRESSION OF A CANCER AND OF THE OUTCOME IN A PATIENT AND MEANS FOR PERFORMING SAID METHOD

FIELD OF THE INVENTION

The present invention relates to the field of prognosis of the outcome of a cancer in a patient.

More precisely, this invention relates to the prognosis of the outcome of a cancer in a patient, which prognosis is based on the quantification of one or several biological markers that are indicative of the presence of, or alternatively the level of, the adaptive immune response of said patient against said cancer.

BACKGROUND OF THE INVENTION

Because cancer is the second leading cause of death, particularly in Europe and in the United States, vast amount of efforts and financial resources are being invested in developing novel therapeutical approaches. However, the need for reliable diagnostic and prognostic tools is a rate-limiting step in the successful application of a cancer therapy. This is best manifested by the fact that most of the currently known markers of cancer are poorly reliable.

To date, malignant tumors are generally classified according to the TNM system. The TNM (for "Tumor-Node-Metastasis") classification system uses the size of the tumor, the presence or absence of tumor in regional lymph nodes, and the presence or absence of distant metastases, to assign a stage to the tumor (AJCC Cancer Staging Manual, Lippincott, 5$^{th}$ edition, pp. 171-180, 1997). The assigned stage is used as a basis for selection of appropriate therapy and for prognostic purposes. When applied for staging colorectal cancers, the TNM system allows the distinction between (T) the degree of invasion of the intestinal wall, ranging from T0 to T4, (N) the degree of lymph node involvement, ranging from N0 to N3 and (M) the degree of metastasis, ranging from M0 to M1.

For colorectal cancers, a stage may be assigned to the tumor also according to the Duke's classification, Duke's classification allows the distinction between at least four main tumor stages, respectively (A) tumor confined to the bowel wall, (B) tumor extending across the bowel wall, (C) involvement of regional nodes and (D) occurrence of distant metastases.

However, the above clinical classifications, although they are to useful, are imperfect and do not allow a reliable prognosis of the outcome of the cancers. This is particularly true for the cancers assigned as Duke Class B, which are of a wide range of seriousness.

Instead of conventional clinical staging, it has been provided in the art a large number of biological markers, including genes and proteins, is that would be potentially useful for the diagnosis or the prognosis of a wide variety of cancers. Notably, it has been disclosed various methods for providing patterns of gene expression that would be potentially useful as cancer diagnosis or prognosis tools, including for diagnosis or prognosis of colorectal cancers.

In this context, various prior art works were aimed at showing a relationship between (i) the presence of, or the expression level of, various biological markers of the host immune response and (ii) the occurrence of a cancer or the stage of cancer development, mainly with the view of deciphering the mechanisms that underlie the escape from the immune response by tumour tissues, and eventually with the view of suggesting suitable anti-cancer immunotherapy strategies.

Illustratively, Nistico et al. (1999, Int. J. Cancer, Vol. 84: 598-603) had suggested the existence of a spontaneous immune response against the erbB-2 oncogene product in HLA-A2-positive breast cancer patient, the efficacy of which might be dependent on tumor HLA-class-I molecule expression and on CD3+-T-lymphocyte localization, i.e. in intratumoral (IT) or peritumoral (PT) tissue. According to these authors, these results could lead to the identification of new parameters that might be useful for defining more specific and more effective immunotherapeutic strategies against breast cancer.

Philips et al. (2004, British Journal of Surgery, Vol. 91: 469-475) had shown that tumour-infiltrating lymphocytes in colorectal cancer with microsatellite instability were activated and cytotoxic, by assaying both (i) the CD8/CD3 mRNA ratios and (ii) the CD3, CD4, CD8, IL-2Ra and Granzyme B protein production in the tumor tissue, although there was to no significant correlation between T cell markers mRNA copy numbers and immunohistochemical counts. These authors suggested that, in colorectal cancer with microsatellite instability, immunogenic mutated peptides might be produced, that would induce an antitumor immune response, and conclude that the said cancer model might help in understanding the host-tumour interactions, notably in view of improving immunotherapeutic strategies.

Maki et al. (2004, J. Gastroenterolgy and Hepatology, Vol. 19: 1348-1356) had shown an impairment of the cellular immune system in hepatocellular carcinoma-bearing patients, that was assessed by a decreased CD3ζ and CD28 protein expression by T cells, as well as by an increased caspase-3 activity in CD28 down-modulated T cells, suggesting the occurrence of a T cell apoptosis in HCC patients. According to these authors, a new modality of antitumor immune therapy might be established, that would be aimed at activating such T cells and prevent them from apoptosis. A CD3ζ decreased expression in T cells infiltrating cervical carcinoma has also been reported by Grujil et al. (1999, British Journal of Cancer, Vol. 79(7/8): 1127-1132). These authors suggested that, in order for vaccination strategies to be successful, it might be essential to first identify and counteract mechanisms leading to this loss of CD3ζ.

Impairment of the host immune response, through the assessment of the expression of CD3, CD4, CD8 and Fas Ligand proteins on tumor-infiltrating lymphocytes (TILs), was also shown in patients with oral carcinoma (Reichert et al. (2002, Clinical Cancer Research, Vol. 8: 3137-3145). Similar observations were made by Prado-Garcia et al. (2005, Lung Cancer, Vol. 47: 361-371) who had studied the evasion mechanisms of lung adenocarcinoma measured the percentages of CD3+, CD4+ and CD8+ cells in peripheral blood and pleural effusion, and further CD27, CD28, CD45R0, CD45RA, granzyme A, Fas and perforin protein expression in the CD8+ Tcell subsets. These authors had found a blocking of the immune response and suggested that further studies were needed for understanding the various mechanisms whereby adenocarcinoma cells inhibit CD8+ T cells in the initiation, growth and invasion processes of lung carcinoma, with the view of developing improved treatments for lung malignancies.

Similar observations were made by Kuss et al. (2003, British Journal of Cancer, Vol. 88: 223-230) who determined an expanded CD8+CD45RO-CD27− effector T cell subset endowed with a dysfunctional TcR signalling, in squalors cell carcinoma-bearing patients. These authors suggested further studies for confirming directly the hypothesis that would link the observed signaling defects with apoptosis and rapid lymphocyte turnover in patients with cancer.

Also, Valmori et al. (2002, Cancer Research, Vol. 62:1743-1750) have found that the presence of a CD45RA+CCR7-CD8+ PBL T cell subset having cytolytic activity in melanoma patients. These authors suggested that improved anti-tumor vaccination should be aimed at stimulating and maintaining such an effector immune response early in the course of the disease, at a time when such a response might be effective to eradicate minimal residual disease and prevent relapses.

The prior works related above disclose the use of numerous biological markers of the immune response in the course of understanding the immune response, mechanisms against various cancers. However, these prior works provide no data relating to a statistical significant relationship between (i) the presence of, or the expression level of, these biological markers and (ii) a prognosis of the outcome of the disease.

Other studies have presented data establishing a statistical correlation between the expression of biological markers of the immune response from the host and the outcome of various cancers.

Illustratively, Ishigami et al. (2002, Cancer, Vol. 94 (5): 1437-1442) showed that reduced CD3-$\zeta$ expression negatively correlated with lymph node involvement, depth of invasion, and clinical stage of gastric carcinoma. Notably, these authors had shown that a reduced CD3-$\zeta$ expression correlate with a reduced 5-year survival rate of the patients, but only for patients which were diagnosed as "Stage IV" of gastric carcinoma.

Oshokiri et al. (2003, Journal of Surgical Ontology, Vol. 84: 224-228) showed a statistical linkage between the infiltration of a cancer cell nest by CD8+ T cells and the survival of patients affected with extrahepatic bile duct carcinoma (EBDC). These authors showed that intratumoral CD8+ T cell immunoreactivity demonstrated a significant correlation with (i) fewer lymph node metastasis, (ii) reduced venous and perineural invasion, and (iii) better pTNM staging values. Thus, these authors showed that the level of CD8+ T cell infiltration correlated well with the conventional pTNM clinicopathological method and that the said biological marker was reliable for predicting the survival of patients with EBDC.

Also, Diederischen et al. (2003, Cancer Immunol, Immunother., Vol. 52: 423-428) showed that colorectal patients with low CD4+/CD8+ ratios in TILs had a better clinical course, with significantly higher 5-year survival, independent of the Dukes stage and age.

Additionally, Zhang et al. (2003, New England Journal of Medicine, Vol. 348(3) 203-213) showed, by immunostaining for CD that the presence or absence of intratumoral T cells correlates with the clinical outcome of advanced ovarian carcinoma after debulking and adjuvant chemotherapy. These results were obtained through immunostaining assays of tumor cryosections with monoclonal antibodies against CD3, CD4, CD8, CD83, CD45, CD45RO, CD19, CD57 and CD11c, as well as through flow cytometry of cells from fresh tumor samples using monoclonal antibodies against HLADR, CD3, CD4, CD8, CD16, CD19, CD45, IgG1 and IgG2a. These authors had detected the presence or absence of CD3+ tumor-infiltrating T cells within tumor-cell islets and in peritumoral stroma. These authors have found that patients whose tumors contained T cells had both a median duration of (i) progression-free survival and (ii) overall survival which was statistically higher than patients whose tumors did not contain T cells. These authors suggested to further validate the use of detection of intratumoral T cells in the classification and treatment of patients with ovarian carcinoma.

Although the prior art works reported above disclose good correlation between (i) the presence of, or the level of, some biological markers of the immune response and (ii) the outcome of cancers, the results of most of these prior art studies also show that the use of the said biological markers were viewed exclusively as a confirmation of a cancer staging with conventional clinicopathological staging methods, or as an additional information to the said conventional cancer staging methods. For example, the biological marker used by Ishigami et al. (2002, Supra) was found to be useable exclusively with gastric carcinoma-bearing patients who where already diagnosed as "Stage IV" of the disease. Similarly, Zhang et al. (2003, Supra) concluded that prospective studies were needed to validate detection of intratumoral (CD3+) T cells in the classification and treatment of patients with ovarian carcinoma. Similarly, Diederichsen et al. (2003, Supra) disclosed the CD4+/CD8+ ratio as a biological marker having a survival prognostic value in colorectal cancer. However, these authors did not suggest that the said biological marker might be sufficient per se for cancer prognosis, without simultaneous staging data generated by conventional clinicopathological staging methods.

Only Oshikiri et al. (2003, Supra) considered that the biological marker that they have used, namely the infiltration of a cancer cell nest by CD8+ T cells, would consist of a reliable marker for longer survival of patients with EBDC, since, notably, the said marker correlated well with pTNM staging values. However, Oshikiri et al. only used the said biological marker as a confirmation of a prior cancer staging by a conventional clinicopathological staging method. Further, the statistical correlation values found by Oshikiri et al. (2003) between (a) the number of intratumoral CD8+ T cells and (b) various clinical parameters like (i) fewer lymph node metastasis (P=0.005), (ii) reduced venous invasion (P=0.0021), (iii) reduced perineural invasion (P=0.0083) and (iv) better pTNM staging values (P=0.0356), were objectively too much low to suggest the one skilled in the art to make use of this biological marker for an accurate and reliable cancer prognosis without the concomitant use of conventional clinicopathological staging data.

There is thus no disclosure in the art of reliable methods of cancer prognosis that would make use exclusively of biological markers of the adaptive immune response from the host, without a need for concomitant clinicopathological data generated by conventional cancer staging methods.

Further, there is, today, no reliable marker available that would allow the prediction of the cancer outcome, in early-stage (stage I/II) colorectal cancer patients.

There is thus a need in the art for improved methods of prognosis of the outcome of cancers, including colorectal cancers, that would stage the disease in a more accurate and a more reliable way than the presently available methods, that is essentially, if not exclusively, clinicopathological staging methods.

Notably, the availability of improved prognosis methods would allow a better selection of patients for appropriate therapeutical treatments, including before and after surgery. Indeed, for numerous cancers including colorectal cancers, the selection of an appropriate therapeutical treatment after surgery is guided by the histopathological data provided by the analysis of the resected tumor tissue. Illustratively, for colorectal cancers, adjuvant chemotherapy treatments are prescribed mostly when involvement of lymph nodes is diagnosed, because of the toxicity of such treatment and its lack of benefit for the other patients.

SUMMARY OF THE INVENTION

The present invention relates to an in vitro method for the prognosis of patients for progression of a cancer, which method comprises the following steps:
   a) quantifying, in a tumor tissue sample from said patient, at least one biological marker indicative of the status of the adaptive immune response of said patient against cancer; and
   b) comparing the value obtained at step a) for said at least one biological marker with a predetermined reference value for the same biological marker; which predetermined reference value is correlated with a specific prognosis of progression of said cancer.

In some embodiments of the method, step a) consists of quantifying one or more biological markers by immunochemical techniques, preferably in two distinct tissues, and especially both (i) in the center of the tumor (CT) and (ii) in the invasive margin (IM).

In some other embodiments of the method, step a) consists of quantifying one or more biological markers by gene expression analysis in the whole tumor tissue sample.

This invention also relates to a kit for the prognosis of progression of a cancer in a patient, which kit comprises means for quantifying at least one biological marker indicative of the status of the adaptive immune response of said patient against cancer.

This invention also pertains to a kit for monitoring the effectiveness of treatment (adjuvant or neo-adjuvant) of a subject with an agent, which kit comprises means for quantifying at least one biological marker indicative of the status of the adaptive immune response of said patient against cancer.

DESCRIPTION OF THE FIGURES

FIG. 7C shows the combined tumour regions analysis of adaptive immune markers. Median DFS of patients with high- (bottom histograms) or low-densities (upper histograms) of adaptive immune cells in both tumour regions (CT plus IM) is represented.

(8a): Kaplan-Meier curves for the duration of DFS according to the Dukes stages (Dukes A: red (n=75), B: green (n=137), C: blue (n=99), and D: black line (n=95)) in 415 patients with colorectal cancer.

(8b): Kaplan-Meier curves for the duration of DFS according to the Dukes stages (as in 8a) and to the presence of Low-$CD3_{CT}$ plus Low-CD31M (thick lines, n=93) or High-$CD3_{CT}$ plus High-$CD3_{IM}$ (thin lines, n=109).

(8c): Kaplan-Meier curves for the duration of DFS according to the Dukes stages and to the presence of Low-$CD3_{CT}$ plus Low-$CD3_{IM}$ plus Low-$CD45RO_{CT}$ plus Low-$CD45RO_{IM}$ (thick, lines, n=25) or High-$CD3_{CT}$ plus High-$CD3_{IM}$ plus High-$CD45RO_{CT}$ plus High-$CD45RO_{IM}$ (thin lines, n=87). ** $P<10^{-4}$.

(8d): Kaplan-Meier curves for the duration of OS according to the Dukes stages and to the presence of Low-$CD3_{CT}$ plus Low-$CD3_{IM}$ plus Low-$CD45RO_{CT}$ plus Low-$CD45RO_{IM}$ (thick lines, n=25) or High-$CD3_{CT}$ plus High-$CD3_{IM}$ plus High-$CD46RO_{CT}$ plus High-$CD45RO_{IM}$ (thin lines, n=87).

Figure 9:
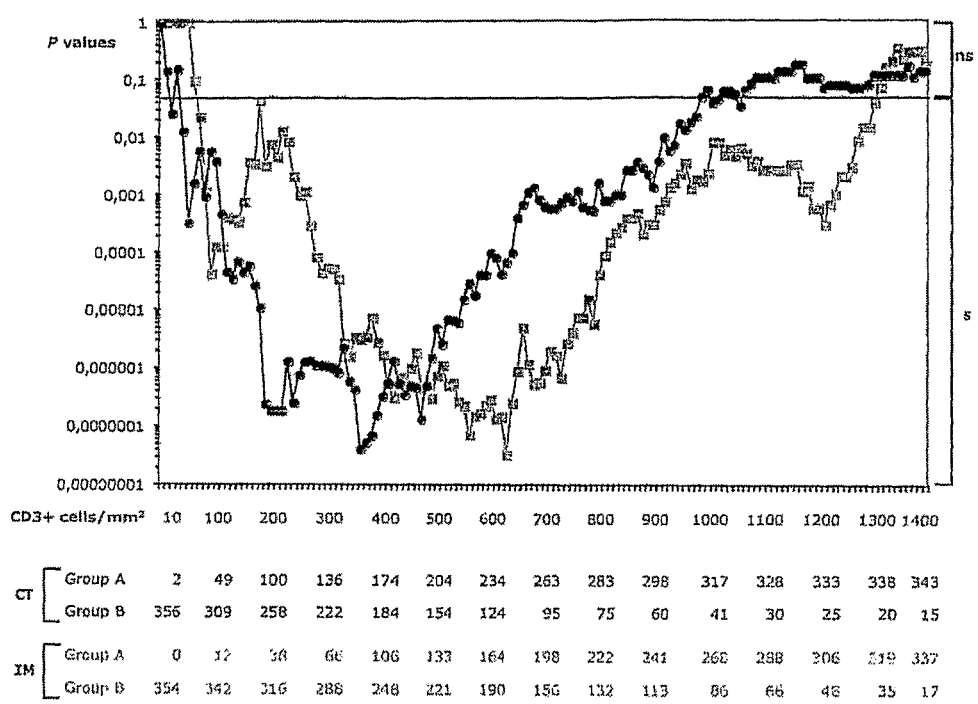

FIG. 9 Log-rank P values for the duration of DFS according to the presence of high-CD3+ density ($CD3^{HI}$, group A) and low high-CD3+ density ($CD3^{LO}$, group B) in the center of the tumor (black), and in the invasive margin of the tumor (grey). CD3+ cell densities (cell/mm$^2$), and the number of patients in each group (A and B) are represented. P-values are significant for a large interval of cut-offs (50-1000 cell/mm$^2$ in the center of the tumor, and 80-1300 cell/mm$^2$ in the invasive margin of the tumor). The results obtained are easily reproducible by other groups as a large range of cut of values, (centered on the minimum P value cut-off that was determined) and discriminate patient outcome.

Figure 10:
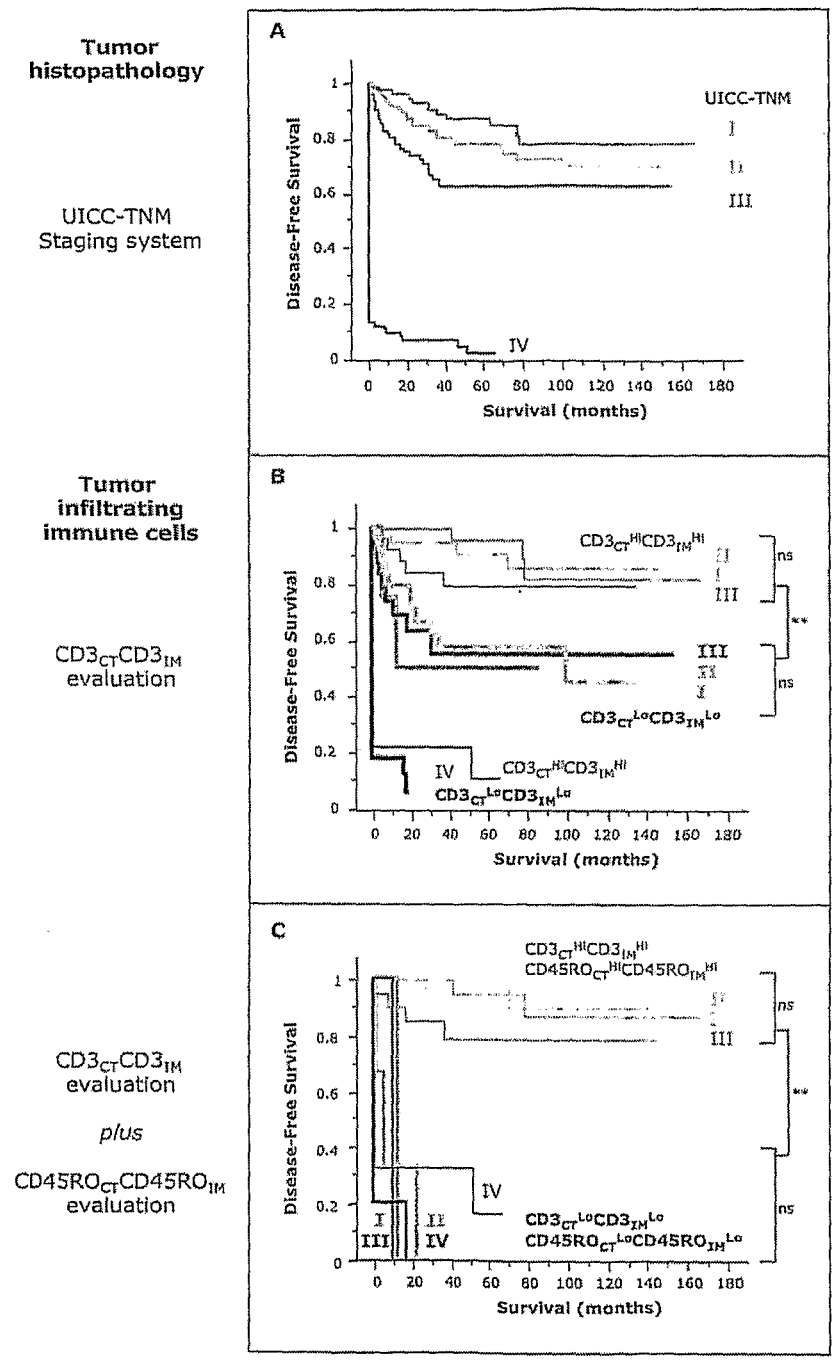

FIG. 10: (FIG. 10-A) Kaplan-Meier curves for the duration of disease-free survival according to the UICC-TNM stages (Stages I: red (n=75), II: green (n=137), III: blue (n=99), and IV: black line (n=95)) in patients with CRCs. (FIG. 10-B) Kaplan-Meier curves illustrate the duration of disease-free survival according to the UICC-TNM stages (as in panel A) and to the density of CD3+ cells in combined tumor: regions ($CD3_{CT}^{Lo}CD3_{IM}^{Lo}$, thick lines, n=93; $CD3_{CT}^{Hi}CD3_{IM}^{Hi}$, thin lines, n=109). The subgroup of patients that did not appear to have a coordinated in situ immune reaction in tumor regions (Hi/Lo or Lo/Hi for CD3+ cell densities) presented similar Kaplan-Meier curves as the entire cohort. (FIG. 10-C) Kaplan-Meier curves illustrate the duration of disease-free survival according to the UICC-TNM stages and to the density of CD3+ and CD45RO+ cells in combined tumor regions ($CD33_{CT}^{Lo}CD3_{IM}^{Lo}$ plus $CD45RO_{CT}^{Lo}CD45RO_{IM}^{Lo}$, thick lines, n=16; $CD3_{CT}^{Hi}CD3_{IM}^{Hi}$ plus $CD45RO_{CT}^{Hi}CD45RO_{IM}^{Hi}$, thin lines, n=88), Cut-off values were 250, 640, 60, and 190 for $CD3_{CT}$, $CD3_{IM}$, $CD45RO_{CT}$, and $CD45RO_{IM}$, respectively. Log-rank statistical test, ** $P<10^{-4}$.

Figure 11:
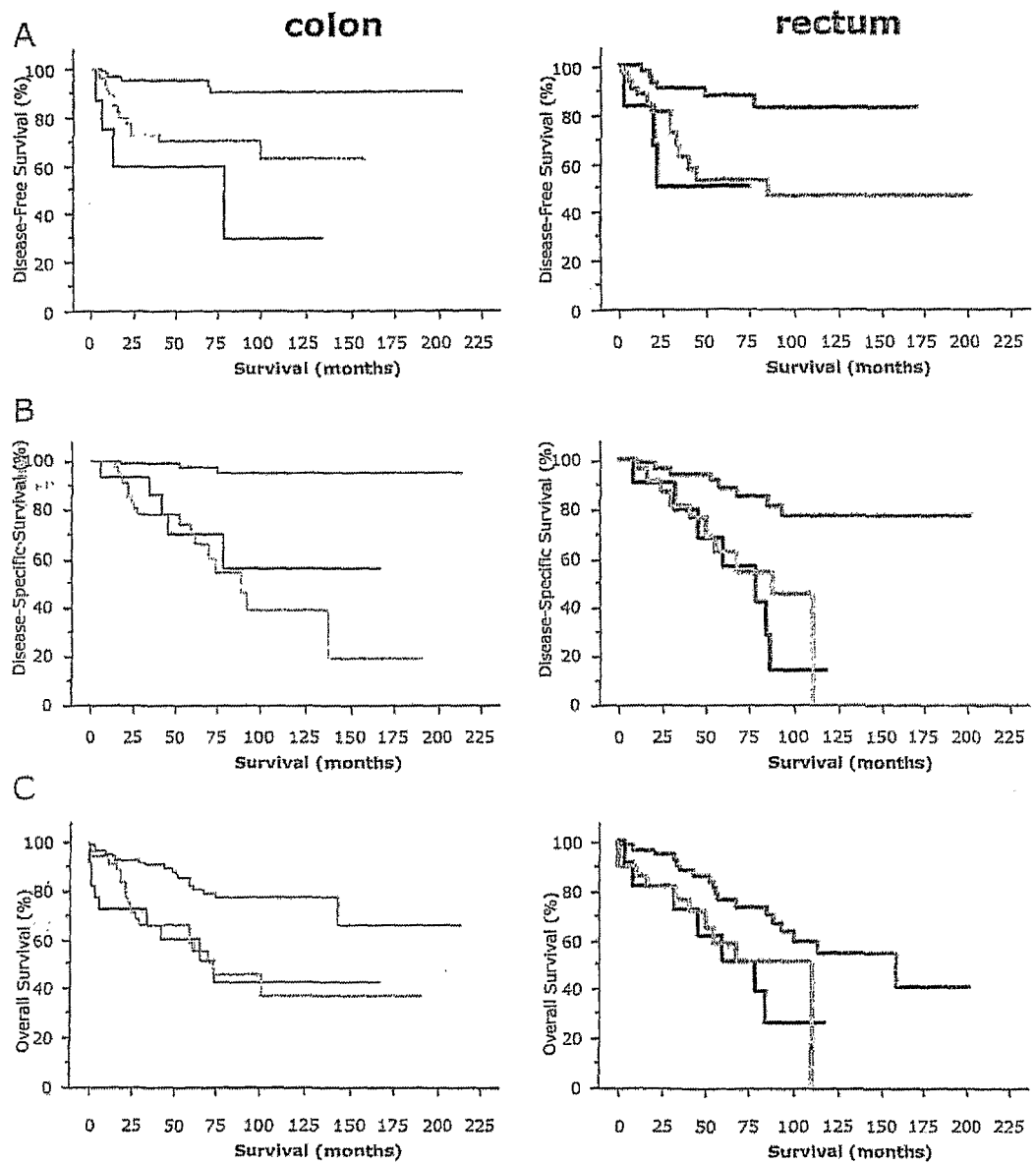

FIG. 11: Kaplan-Meier curves illustrating the duration of disease-free survival (A), disease-specific survival (B), and overall survival (C) according to the organization of CD8+ cells within the tumor regions (CT and IM) are represented. Presence of high densities of CD8+ cells in both tumor regions (CD8-CT/IM-hi, red), of heterogeneous densities of CD8+ cells in both tumor regions (CD8-CT/IM-het, green), of low densities of CD8+ cells in both tumor regions (CD8-CT/IM-lo, black), in patients with stage I/II colon cancer (left) and rectum cancer (right) (log-rank statistical test, P<0.001 for all comparisons).

Figure 12:
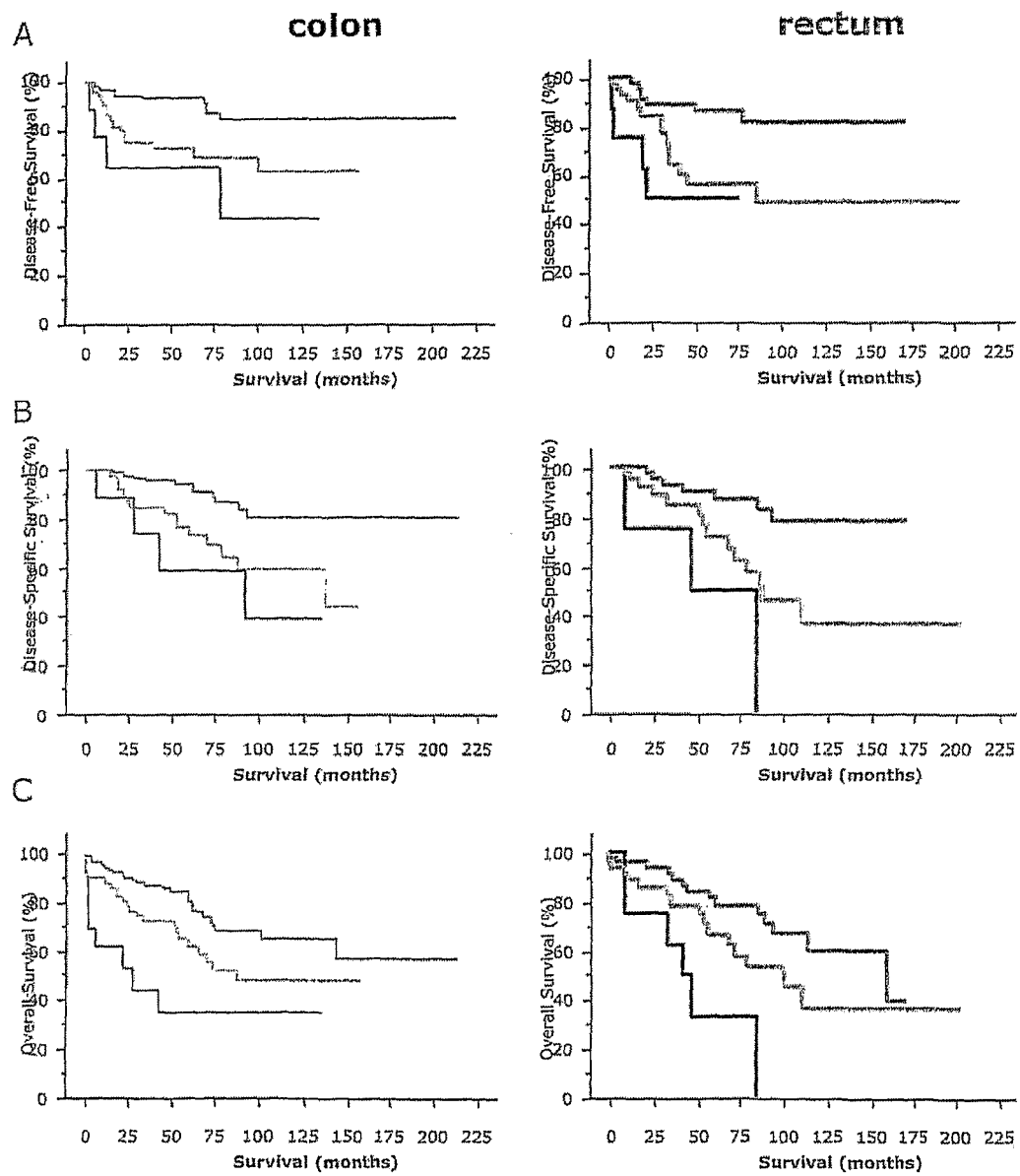

FIG. 12 Kaplan-Meier curves illustrating the duration of disease-free survival (A), disease-specific survival (B), and overall survival (C) according to the organization of CD45RO+ cells within the tumor regions (CT and IM) are represented. Presence of high densities of CD45RO+ cells in both tumor regions (CD8-CT/IM-hi, red), of heterogeneous densities of CD45RO+ cells in both tumor regions (CD45RO-CT/IM-het, green), of low densities of CD45RO+ cells in both tumor regions (CD45RO-CT/IM-lo, black), in patients with stage I/II colon cancer (left) and rectum cancer (right) (log-rank statistical test, P<0.001 for all comparisons).

Figure 13:
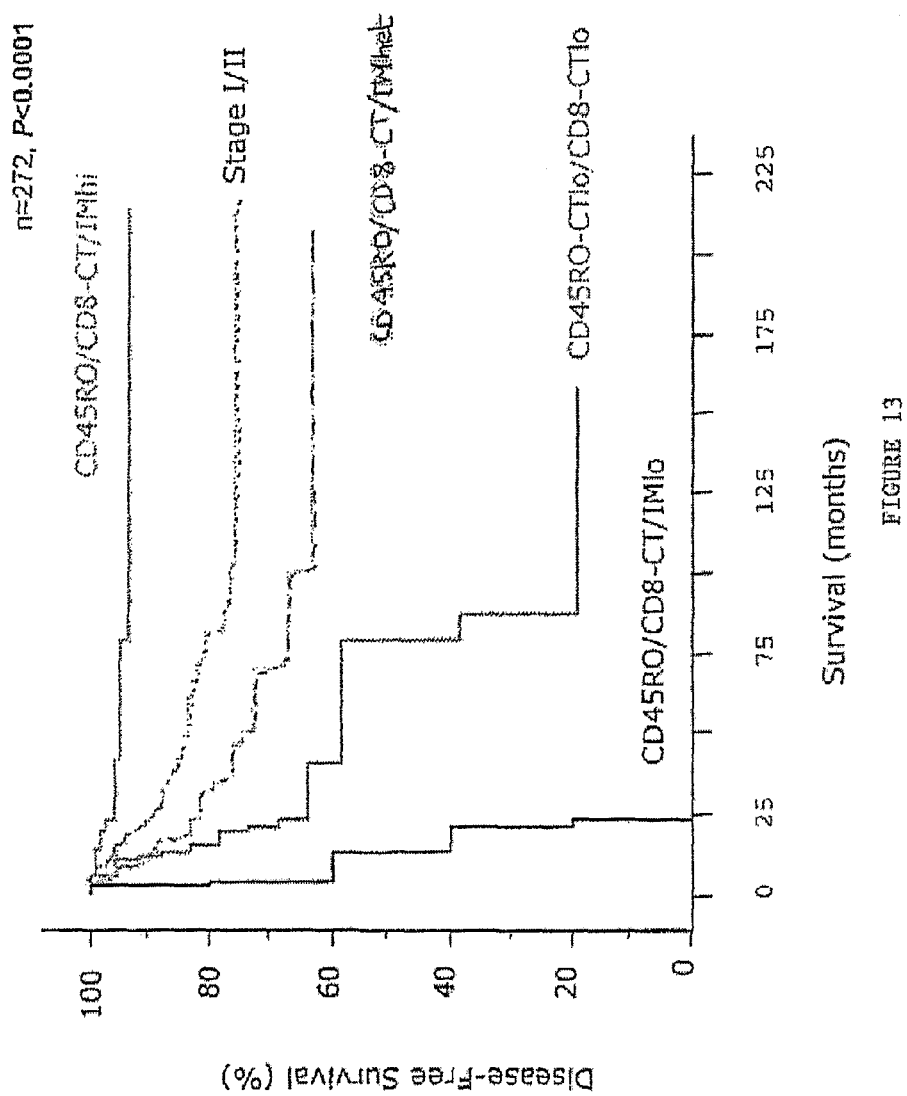

FIG. 13 Kaplan-Meier curves illustrating the duration of disease-free survival according to the organization of CD45RO+ and CD8+ cells within the tumor regions (CT and IM) are represented. Presence of high densities of CD45RO+ and CD8+ cells in both tumor regions (CD45RO/CD8-CT/IM-hi, red), of heterogeneous densities of CD45RO+ and CD8+ cells in both tumor regions (CD45RO/CD8-CT/IM-het, green), of low densities of CD45RO+ and CD8+ cells in CT region (CD45RO-CT-lo/CD8-CT-lo, blue), of low densities of CD45RO+ and CD8+ cells in both tumor regions (CD45RO/CD8-CT/IM-lo, black), in 272 patients with stage I/II colorectal cancer (log-rank statistical test, P<0.001 for all comparisons). The all cohort of patients with stage I/II colorectal cancer is represented (black dotted line).

Thus, >95% CD45RO/CD8-CT/IM-hi patients Were disease-free after 18 years, whereas 0% CD45RO/CD8-CT/IM-lo patients were disease-free after only 2 years.

Figure 14:
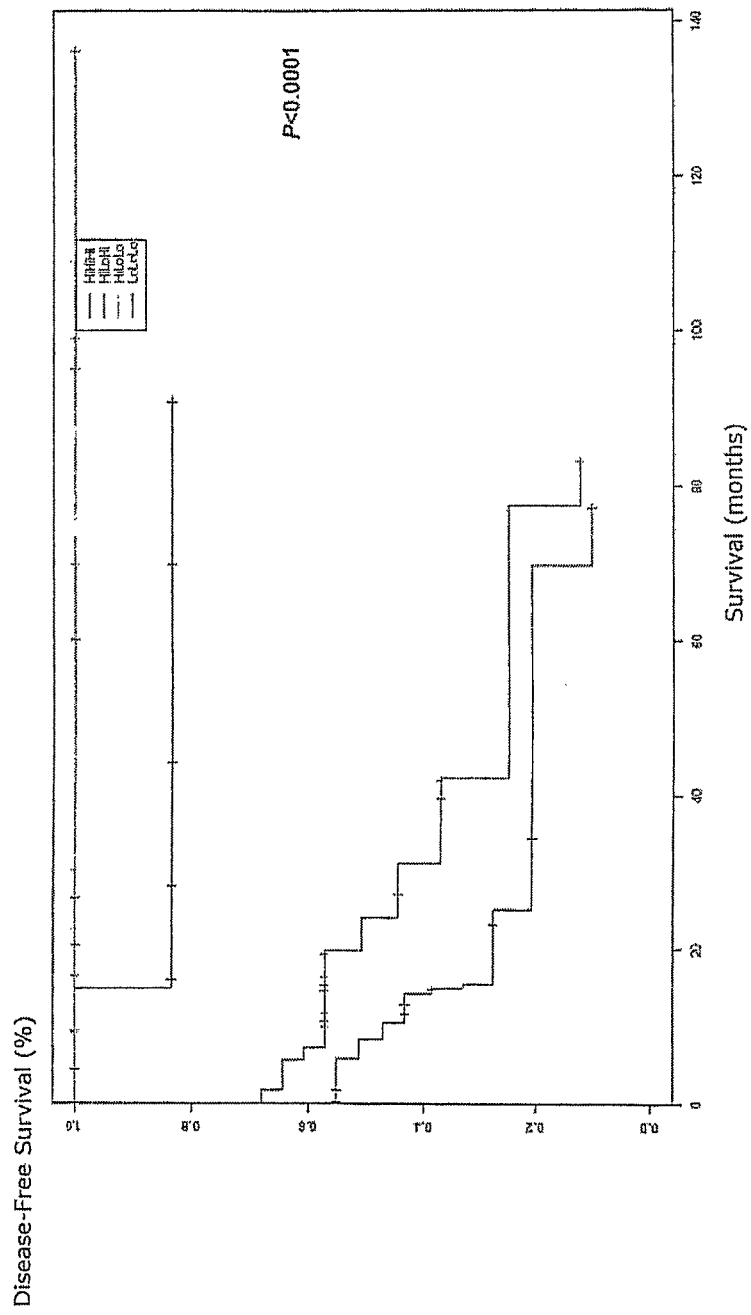

FIG. 14: Kaplan-Meier curves illustrating the duration of disease-free survival according to the gene expression level of 6 markers (PDCD1LGI$_1$, VEGF, TNFRSF6B, IRF1, IL18RA, SELL). Four combinations are represented. (log-rank statistical test, P<0.001 for all comparisons).

DETAILED DESCRIPTION OF THE INVENTION

The present invention provides a novel method for the prognosis of the outcome of a cancer in a patient, which novel method is based on the detection and/or the quantification, at the tumor site, of one or more biological markers indicative of the presence of, or alternatively of the level of, the adaptive immune response of said patient against said cancer.

It has now been surprisingly shown according to the invention that a precise determination of the in situ adaptive immune response to malignant cancers, and especially to colorectal cancers, can be used as the sole parameter for predicting the subsequent clinical outcome of cancer-bearing patients, regardless of the extent of local tumor invasion and spread to regional lymph nodes.

This statistically highly significant correlation between (i) the level of the adaptive immune response from the patient at the tumor site and (ii) the outcome of the disease is all the more surprising that, according to the prior art knowledge, the presence of infiltrating immune cells in mammal cancers accounted for highly variable outcomes, ranging from deleterious inflammatory processes to beneficial adaptive immune responses.

Further, the said highly significant correlation that is surprisingly found according to the invention now allows determination of the prognosis of the outcome of a cancer in a patient without further needing clinicopatholigal data that are provided by the conventional clinicopathological cancer staging methods known in the art, like Duke's or Gruji's methods.

As it will be detailed further, when determining statistical to correlation between (i) the presence of, or the level of, one or more biological markers of the adaptive immune response, as disclosed in the specification and (ii) the actual outcome of cancer in patients, encompassing Disease-free survival (DFS) and Overall survival (OS), P values of more than $10^{-8}$ have been obtained according to the invention, to be compared to the P values of $5 \times 10^{-2}$ to $1 \times 10^{-3}$ that were disclosed in various prior art works like, illustratively, those of Zhang et al. (2003, Supra), Diederischen et al. (2003, Supra) or Oshikiri et al. (2003, Supra).

The applicant has found that there is a highly significant relationship (e.g. low P values) between (i) the type, density, and location of immune cells within tumors and (ii) the clinical outcome of the patients, encompassing DFS and OS. This highly significant correlation has been found when using, for assaying biological markers of the adaptive immune response, either (i) immunochemistry assays or (ii) gene expression analysis.

By analysis of biological markers of the adaptive immune response by gene expression analysis in the whole tumor tissue sample, a high number of significant combinations of markers were found, including numerous significant combinations of at least two markers, with P values of about $10^{-4}$, or lower.

Importantly, it has been identified herein a dominant cluster of co-modulated genes for $T_{H1}$ adaptive immunity, which cluster includes TBX1 (T-box transcription factor 21), IRF1 (interferon regulatory factor 1), IFNG (gamma-Interferon), CD3Z (CD3ζ), CD8, GLNY (granulysin) and GZMB (granzyme B). Further, an inverse correlation has been found between expression of these genes and tumor recurrence.

Another highly significant cluster of genes according to the invention includes PDCD1LG1, VEGF, TNFRSF6B, IRF1, IL8RA and SELL.

By analysis of biological markers of the adaptive immune response by immunohistochemical analysis, either (i) in the center of the tumor (CT), (ii) in the cellular environment surrounding the tumor, which may also be termed the "invasive margin" (IM) or (iii) in both CT and IM, a number of significant combinations of markers were also found. Highest statistical correlation values were found when the biological markers were quantified both in the center of the tumor (CT) and in the invasive margin (IM).

Firstly, it has been found according to the invention that there is a high correlation between a high density of T cells at the tumor site and a favorable outcome of the disease. Particularly, IR has been shown that a positive outcome of the cancer is highly correlated with the quantification of a high density of CD3+ cells, CD8+ cells, CD45RO+ cells or Granzyme-B+ cells at the site of the tumor, either in the central part of the tumor or in the invasive margin thereof.

Secondly, it has been found that the determination of the presence of high densities of CD3+ cells, CD8+ cells, CD45RO+ cells or Granzyme-B+ cells at the site of the tumor is highly correlated with reduced cancer recurrence and/or delayed cancer recurrence and/or a lack of cancer recurrence.

Thirdly, it has been found that the determination of the presence of high densities of CD3+ cells, CD8+ cells, CD45RO+ cells or Granzyme-B+ cells at the site of the tumor is highly correlated with reduced concomitant distant metastasis, or a lack of concomitant distant metastasis (M-stages)., Fourthly, it has been found that the determination of the presence of high densities of CD3+ cells, CD8+ cells, CD45RO+ cells or GranzymeB+ cells at the site of the tumor is highly correlated with reduced early metastasis, or a lack of early metastasis (VE or LI or PI).

Fifthly, it has been found that the determination of the presence of high densities of CD3+ cells, CD8+ cells, CD45RO+ cells or Granzyme-B+ cells at the site of the tumor is highly correlated with a reduced invasion of the regional lymph nodes with tumor cells (N-stages).

Sixthly, it has been found that the determination of the presence of high densities of CD3+ cells, CD8+ cells, CD45RO+ cells or Granzyme-B+ cells at the site of the tumor is highly correlated with a reduced invasion through the intestinal wall (T-stages).

More generally, it has been found that the absence of early dissemination of tumor manifested by tumor emboli in lymphovascular and perineural structures is markedly associated with the presence of a strong in situ immune response, said strong immune response being illustrated, notably, by the high immune cell densities found at the tumor site, as well as by the high expression level of various genes associated with immunity at the tumor site.

Further, it has been found according to the invention that the detection of a strong adaptive immune response at two distinct regions of the tumor, the center of the tumor (CT) pluS the invasive margin of the tumor (IM), was highly correlated with a long disease-free survival time and overall survival time of the patients, and significantly more informative for prognosis of patient of progression of cancer.

Importantly, It has been found herein a high correlation between (i) the cell density of a specific type of cells form the immune system, as assayed in an immunohistochemical assay using a single biological marker, and (ii) DFS or OS, with P values of at least as low as $10^{-7}$, when the said biological marker is assayed both in the center of the tumor (CT) and in the invasive margin (IM).

Generally; it has been found according to the invention that the type, the density, and the location of immune cells in cancer patients, as assayed through the presence of, or the level of, biological markers of the adaptive immune response, has a prognostic value that is superior and independent of those of conventional clinicopathological cancer staging methods, including the Duke's and the UICC-TNM classifications.

Even more specifically, the present invention now provides prognostic methods and technical means for predicting the outcome of a cancer in a patient, particularly for cancers at an early stage of the disease, that have proved to be far more accurate than the conventional clinicopathological cancer staging methods, and further especially for cancers initially classified as Stage I/III according to Duke's classification.

Thus, it has been found according to the invention that the detection of a strong adaptive immune response at the tumor site was highly correlated with a long disease-free survival time (DFS) and overall survival time (OS) of the patients.

Thus, a first object of the present invention consists of an in vitro method for the prognosis of progression of a cancer in a patient, which method comprises the following steps:

a) quantifying, in a tumor tissue sample from said patient, at least one biological marker indicative of the status of the adaptive immune response of said patient against cancer; and b) comparing the value obtained at step a) for said at least one biological marker with a predetermined reference value for the same biological marker; which predetermined reference value is correlated with a specific prognosis of progression of said cancer.

Unexpectedly, it has been found according to the invention that a strong coordinated adaptive immune response correlated with an equally favorable cancer prognosis.

Still unexpectedly, it has been found that said correlation found according to the invention was independent of the tumor invasion through the intestinal wall and extension to the local lymph-nodes (Duke's classification A, B, C).

Conversely, it has been surprisingly found that a weak in situ adaptive immune response correlated with a very poor prognosis, even in patients with minimal tumor invasion (Duke's classification A).

Thus, the criteria used according to the cancer prognosis method of he invention, namely the status of the adaptive immune response of the cancer patient, appear not only different from those of the T, N, M and Duke's classification, but are also more precise in predicting disease (disease-free interval and survival time).

Thus, it has been found for the first time according to the invention that the measure of the level of the adaptive immune response of a cancer-bearing patient can be used as the sole measure for predicting the outcome of the cancer disease, without any requirement of further data, and particularly without any requirement for clinicopathological data provided by conventional cancer staging methods.

Indeed, although various prior art works had pointed out the possible relevance of marker(s) of the adaptive immune response for cancer prognosis, these prior works contained only data that might be used as a confirmation or as an additional information to the prognosis data furnished by the conventional cancer staging methods. Thus, no prior art works disclosed nor suggested any reliable or reproducible in vitro cancer prognosis method that would be based exclusively on the measurement of one or more biological markers indicative of the adaptive immune response of the cancer-bearing patients.

It has also been found that the detection of a strong adaptive immune response at the tumor site was a reliable marker for a plurality of cancers, like colon cancers as well as rectum cancers.

Performing the cancer prognosis method of the invention may also indicate, with more precision than the prior art methods, those patients at high-risk of tumor recurrence who may benefit from adjuvant therapy, including immunotherapy.

As intended herein, the expression "prognosis of progression of a cancer" encompasses the prognosis, in a patient wherein the occurrence of a cancer has already been diagnosed, of various events, including:

(i) the chances of occurrence of metastasis;
(ii) the chances of occurrence of loco-regional recurrence of cancer, including colorectal cancer; and
(iii) the chances of occurrence of a long disease-free (DFS) and/or long overall survival (OS) times; i.e. a DFS time or an OFS time of 5 years or more following testing with the in vitro prognosis method according to the invention.

As intended herein, a "tumor tissue sample" encompasses (i) a global primary tumor (as a whole), (ii) a tissue sample from the center of the tumor, (iii) a tissue sample from the tissue directly surrounding the tumor which tissue may be more specifically named the "invasive margin" of the tumor, (iv) lymphoid islets in close proximity with the tumor, (v) the lymph nodes located at the closest proximity of the tumor, (vi) a tumor tissue sample collected prior surgery (for follow-up of patients after treatment for example), and (vii) a distant metastasis.

Preferably, when step a) consists of the expression analysis of one or more genes, i.e. one or more pertinent biological markers, then the quantification of the expression of the said one or more genes is performed from the whole tumor tissue sample.

Preferably, when step a) consists of the assessment of specific immune cell densities, by immunohistochemical assays for one or more cell-expressed biological makers, then the quantification of the of the said one or more biological markers is performed separately in at least two distinct tumor tissue samples, among the tumor tissue samples numbered (i) to (vi) above. Most preferably, according to this embodiment, the quantification of the said one or more biological markers is performed separately in both (i) in the center of the tumor (CT) and (ii) in the invasive margin (IM).

A tumor tissue sample, irrespective of whether it is derived from the center of the tumor, from the invasive margin of the tumor, or from the closest lymph nodes, encompasses pieces or slices of tissue that have been removed from the tumor center of from the invasive margin surrounding the tumor, including following a surgical tumor resection or following the collection of a tissue sample for biopsy, for further quantification of one or several biological markers, notably through histology or immunohistochemistry methods, through flow cytometry methods and through methods of gene or protein expression analysis, including genomic and proteomic analysis. It will be appreciated that is tumor tissue samples may be used in the cancer prognosis method of the present invention. In these embodiments, the level of expression of the biological marker can be assessed by assessing the amount (e.g. absolute amount or concentration) of the biological marker in a tumor tissue sample, e.g., tumor tissue smear obtained from a patient. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the biological marker in the sample. Likewise, tumor tissue smears may also be subjected to post-collection preparative and storage techniques, e.g., fixation.

As intended herein, the "adaptive immune response" encompasses the presence or the activity, including the activation level, of cells from the immune system of the host cancer patient locally at the tumor site.

As intended herein, the expression "the adaptive immune response of said patient against said tumor" encompasses any adaptive immune response of said patient through direct (TCR-dependent) or indirect (TCR-independent), or both, action towards said cancer.

The adaptive immune response means the specific immune response of the host cancer patient against the tumor and encompasses the presence of, the number of, or alternatively the activity of, cells involved in the specific immune response of the host which includes:

As used herein, the T lymphocytes, encompass T helper to lymphocytes, including Th1 and Th2 T helper lymphocytes cell subsets.

As used herein, the T lymphocytes also encompass T cytototoxic lymphocytes.

Adaptative Immunity

In comparison to innate immunity, acquired (adaptive) immunity develops when the body is exposed to various antigens and builds a defense that is specific to that antigen.

The adaptive immune response is antigen-specific and may take days or longer to develop. Cell types with critical roles in adaptive immunity are antigen-presenting cells including macrophages and dendritic cells. Antigen-dependent stimulation of T cell subtypes, B cell activation and antibody production, and the activation of macrophages and NK cells all play important roles in adaptive immunity. The adaptive immune response also includes the development of immunological memory, a process that continues to develop throughout life and enhances future responses to a given antigen.

Lymphocytes, a special type of white blood cell, contain subgroups, B and T lymphocytes, that are key players in acquired immune responses. B lymphocytes (also called B cells) produce antibodies. Antibodies attach to a specific antigen and make it easier for the phagocytes to destroy the antigen. T lymphocytes (T cells) attack antigens directly, and provide control of the immune response. B cells and T cells develop that are specific for ONE antigen type. When you are exposed to a different antigen, different B cells and T cells are formed.

As lymphocytes develop, they normally learn to recognize the body's own tissues (self) as distinctive from tissues and particles not normally found in your body (non-self). Once B cells and T cells are formed, a few of those cells will multiply and provide "memory" for the immune system, This allows the immune system to respond faster and more efficiently the next time you are exposed to the same antigen, and in many cases will prevent you from getting sick. For example, adaptive immunity accounts for an individual who has had chickenpox for being so-called 'immune' to getting chickenpox again Adaptive Immune System The adaptive immune system, also called the acquired immune system, explains the interesting fact that when most mammals survive an initial infection by a pathogen, they are generally immune to further illness caused by that same pathogen. This fact is exploited by modern medicine through the use of vaccines. The adaptive immune system is based on immune cells called leukocytes (or white blood cells) that are produced by stem cells in the bone marrow. The immune system can be divided into two parts. Many species, including mammals, have the following type:

The humoral immune system, which acts against bacteria and viruses in the body liquids (such as blood). Its primary means of action are immunoglobulins, also called antibodies, which are produced by B cells (B means they develop in the bone marrow).

The cellular immune system, which takes care of other cells that are infected by viruses. This is done by T cells, also called T lymphocytes (T means they develop in the thymus). There are two major types of T cells:

Cytotoxic T cells (TC cells) recognize infected cells by using T-cell receptors to probe the surface of other cells. If they recognize an infected cell, they release granzymes to signal that cell to become apoptotic ("commit suicide"), thus killing that cell and any viruses it is in the process of creating.

Helper T cells (TH cells) interact with macrophages (which ingest dangerous material), and also produce cytokines (interleukins) that induce the proliferation of B and T cells.

In addition, there are Regulatory T cells (Treg cells) which are important in regulating cell-mediated immunity.

Cytotoxic T cells: a cytotoxic (or TC) T cell is a T cell (a type of white blood cell) which has on its surface antigen receptors that can bind to fragments of antigens displayed by the Class I MHC molecules of virus infected somatic cells and tumor cells. Once activated by a MHC-antigen complex, TC cells release the protein perforin, which forms pores in the target cell's plasma membrane; this causes ions and water to flow into the target cell, making it expand and eventually lyse. TC also release granzyme, a serine protease, that can enter target cells via the perforin-formed pore and induce apoptosis (cell death). Most TC cells have present on the cell surface the protein CD8, which is attracted to portions of the Class I MHC molecule. This affinity keeps the TC cell and the target cell bound closely together during antigen-specific activation. TO cells with CD8 surface protein are called CD8+ T cells.

Helper (or TH) T cells: a helper (or TH) T cell is a T cell (a type of white blood cell) which has on its surface antigen receptors that can bind to fragments of antigens displayed by the Class II MHC molecules-found on professional antigen-presenting cells (APCs). Once bound to an antigen, the TH cell proliferates and differentiates into activated TH cells and memory TH cells. Activated TH cells secrete cytokines, proteins or peptides that stimulate other lymphocytes; the most common is interleukin-2 (IL-2), which is a potent T cell growth factor. Activated, proliferating TH cells can differentiate into two major subtypes of cells, Th1 and Th2 cells. These subtypes are defined on the basis of specific cytokines produced. Th1 cells produce interferon-gamma and interleukin 12, while Th2 cells produce interleukin-4, interleukin-5 and interleukin-13, Memory TH cells are specific to the antigen they first encountered and can be called upon during the secondary immune response. Most TH cells have present on the cell surface the protein CD4, which is attracted to portions of the Class II MHC molecule. This affinity keeps the TH cell and the target cell bound closely together during antigen-specific activation. TH cells with CD4 surface protein are called CD4+ T cells. The decrease in number of CD4+ T cells is the primary mechanism by which HIV causes AIDS.

Other Definitions of Relevant Terms

As used herein the expression "tumor site" means the tumor tissue itself as well as the tissue which is in close contact with the tumor tissue, including the invasive margin of the tumor and the regional lymph nodes that are the most close to the tumor tissue or to the invasive margin of the tumor.

As intended herein, the "status" of the adaptive immune response encompasses (i) the existence of a specific immune response against cancer at the tumor site as well as (II) the level of said specific immune response.

As intended herein, a "biological marker" consists of any detectable, measurable or quantifiable, parameter that is indicative of the status of the adaptive immune response of the cancer patient against the tumor. A marker becomes a "biological marker" for the purpose of carrying out the cancer prognosis method of the invention when a good statistical correlation is found between (i) an increase or a decrease of the quantification value for said marker and (ii) the cancer progression actually observed within patients. For calculating correlation values for each marker tested and thus determining the statistical relevance of said marker as a "biological marker" according to the invention, any one of the statistical method known by the one skilled in the art may be used. Illustratively, statistical methods using Kaplan-Meier curves and/or univariate analysis using the log-rank-test and/or a Cox proportional-hazards model may be used, as it is shown in the examples herein. Any marker for which a P value of less than 0.05, and even preferably less than $10^{-3}$, $10^{-4}$, $10^{-5}$, $10^{-6}$ or $10^{-7}$ (according to univariate and multivariate analysis (for example, log-rank test and Cox test, respectively) is determined consists of a "biological marker" useable in the cancer prognosis method of the invention.

Biological markers include the presence of, or the number or density of, cells from the immune system at the tumor site.

Biological markers also include the presence of, or the amount of proteins specifically produced by cells from the immune system at the tumor site.

Biological markers also include the presence of, or the amount of, any biological material that is indicative of the expression level of genes related to the raising of a specific immune response of the host, at the tumor site. Thus, biological markers include the presence of, or the amount of, messenger RNA (mRNA) transcribed from genomic DNA encoding proteins which are specifically produced by cells from the immune system, at the tumor site.

Biological markers thus include surface antigens that are specifically expressed by cells from the immune system, including by B lymphocytes, T lymphocytes, monocytes/macrophages dendritic cells, NK cells, NKT cells, and NK-DC cells., that are recruited within the tumor tissue or at its close proximity, including within the invasive margin of the tumor and in the closest lymph nodes, or alternatively mRNA encoding for said surface antigens.

Illustratively, surface antigens of interest used as biological markers include CD3, CD4, CD8 and CD45RO, that are expressed by T cells or T cell subsets.

For example, if the expression of the CD3 antigen, or the expression of the mRNA thereof, is used as a biological marker, the quantification of this biological marker, at step a) of the method according to the invention, is indicative of the level of the adaptive immune response of the patient involving all T lymphocytes and NKT cells.

For instance, if the expression of the CD8 antigen, or the expression of the mRNA thereof, is used as a biological marker, the quantification of this biological marker, at step, a) of the method according to the invention, is indicative of the level of the adaptive immune response of the patient involving cytotoxic T lymphocytes.

For example, if the expression of the CD45RO antigen, or the expression of the mRNA thereof, is used as a biological marker, the quantification of this biological marker, at step a) of the method according to the invention, is indicative of the level of the adaptive immune response of the patient involving memory T lymphocytes or memory effector T lymphocytes.

Yet illustratively, proteins used as biological markers also include cytolytic proteins specifically produced by cells from the immune system, like perforin, granulysin and also granzyme-B.

Description of the In Vitro Method for Cancer Prognosis

Step a) of the Method

At the end of step a) of the method according to the invention, a quantification value is obtained for each of the at least one biological marker that is used.

As it has been previously specified, specific embodiments of step a) include:

(I) quantifying one or more biological markers by immunochemical methods, which encompass quantification of one or more protein markers of interest by in situ immunohistochemical methods on a tumor tissue sample, for example using antibodies directed specifically against each of the said one or more protein markers. In certain embodiments, the resulting quantification values consist of the density of cells expressing each of the protein markers in the tumor tissue sample under analysis.

(ii) quantifying one or more biological markers by gene expression analysis, which encompasses quantification of one or more marker mRNAs of interest, for example by performing a Real-Time PCR Taqman PCR analysis.

Thus, in certain embodiments of the method, step a) consists of quantifying, in a tumor tissue sample, the cells expressing a specific biological marker of the adaptive immune response. Generally a combination of at least two biological markers is assayed. In these embodiments of step a) of the method, the value obtained at the end of step a) consists of the number or the density of cells of the immune system, or cell subsets thereof, that are contained in the said tumor tissue sample and that express one specific biological marker, for example among the combination of biological markers. In these embodiments, what is obtained at the end of step a) consists of the cell density values found for each biological marker included in the combination of markers. As used herein, the density of cells of interest may be expressed as the number of these cells of interest that are counted per one unit of surface area of tissue sample, e.g. as the number of these cells of interest that are counted per $cm^2$ or $mm^2$ of surface area of tissue sample. As used herein, the density of cells of interest may also be expressed as the number of these cells of interest per one volume unit of sample, e.g. as the number of cells of interest per $cm^3$ of sample. As used herein, the density of cells of Interest may also consist of the percentage of a specific cell subset (e.g. CD3+ T cells) per total cells or total cell subpopulation (set at 100%). For example in an embodiment of the method, cells are firstly collected by mechanical dispersion from the tumor tissue sample and cells of interest are then counted by flow cytometry, optionally after labeling, for instance by labeled surface antigen-specific antibodies, before determining cell density. The inventors believe that the high statistical relevance that they have, found between (i) the quantification values of the biological markers of interest, and (ii) the outcome of the cancer disease, when assessed the said quantification values are assessed by immunohistochemical methods may be explained at least by:

- a highly precise quantification method for each marker, like the numbering of marker-expressing cells per surface area of a tumor tissue slice, as performed from a plurality of distinct surface areas of the said tumor tissue slice; and
- a combined separate quantification of the said marker in more than one kind of tissue sample, e.g. a combined quantification of the said biological marker both (i) in the center of the turner (CT) and (ii) in the invasive margin (IM), it being understood that the statistical relevance is then calculated, e.g. by multivariate analysis, starting from the combination of the quantification values that are measured.

In certain other embodiments of the method, step a) consists of quantifying, in a tumor tissue sample, the expression level of one or more marker genes of the adaptive immune response (e.g. the amount of the corresponding specific mRNAs). Generally, the assessment of the expression level for a combination of at least two marker genes is performed. In these embodiments of step a) of the method, what is obtained at the end of step a) consists of the expression level values found for each marker protein(s) specifically produced by cells from the immune system, that is included in the combination of markers.

Said expression level may also be expressed as any arbitrary unit that reflects the amount of mRNA encoding said protein of interest that has been detected in the tissue sample, such as intensity of a radioactive or of a fluorescence signal emitted by the cDNA material generated by PCR analysis of the mRNA content of the tissue sample, including by Real-time PCR analysis of the mRNA content of the tissue sample.

Alternatively, the said expression level may be expressed as any arbitrary unit that reflects the amount of the protein of interest that has been detected in the tissue sample, such as intensity of a radioactive or of a fluorescence signal emitted by a labeled antibody specifically bound to the protein of interest. Alternatively, the value obtained at the end of step a) may consist of a concentration of protein(s) of interest that could be measured by various protein detection methods well known in the art, such as. ELISA, SELDI-TOF, FACS or Western blotting.

In certain embodiments of step a) of the cancer prognosis method according to the invention, the biological marker(s) is (are) quantified separately in one, or more than one, tumor tissue sample from the cancer patient, selected from the group consisting of (i) a global primary tumor (as a whole), (ii) a tissue sample from the center of the tumor, (iii) a tissue sample from the tissue directly surrounding the tumor which tissue may be more specifically named the "invasive margin" of the tumor (iv) the lymph nodes located at the closest proximity of the tumor, (v) a tumor biopsie perform prior surgery (for follow-up of patients after treatment for example), and (vi) a distant metastasis. In these embodiments, quantification value that is obtained, at the end of step a), for each of the tumor: tissue samples (i), (ii) or (iii), is compared, at step b) of the method, with the corresponding reference values previously determined for each of the tumor tissue samples (i) to (vi), respectively. Obtaining, at step a) of the method, more than one quantification value for each biological marker that is used allows a more accurate final cancer prognosis than when only one quantification value per biological marker is determined.

In other embodiments of the cancer prognosis method according to the invention, quantification values for more than one biological marker are obtained, at step a) of the method. In these embodiments, step b) is carried out by comparing, for each biological marker used, (i) the quantification value obtained at step a) for this biological marker with (ii) the predetermined reference value for the same biological marker.

In further embodiments of the cancer prognosis method according to the invention, step a) is performed by obtaining quantification values for more than one tumor tissue sample for a single biological marker and step a) is performed by obtaining quantification values for more than one biological markers, which quantification values are then compared, at step b), with the corresponding predetermined reference values.

In preferred embodiments of the in vitro prognosis method of the invention, step a) is selected from the group consisting of:
a1) quantifying the said at least one biological marker in a tumor tissue section by immunodetection, separately both (i) in the center of the tumor (CT) and (ii) in the invasive margin (IM); and
a2) quantifying the said at least one biological marker in the whole tumor tissue sample by gene expression analysis.

According to a first specific embodiment of the in vitro prognosis method of the invention, step a1) is performed by quantifying at least two distinct biological markers, separately both (i) in the center of the tumor (CT) and (ii) in the invasive margin (IM).

When, in the in vitro method of the invention, step a) consists of step a1), then step b) is performed by comparing (i) each quantification value obtained for the same biological marker, respectively in CT and IM with (ii) the corresponding reference values, respectively for CT and IM.

According to a second specific embodiment of the in vitro prognosis methods of the invention, step a2) is performed by quantifying at least five, distinct biological markers in the whole tissue sample.

When, in the in vitro method of the invention, step a) consists of step a2), then step b) is performed by comparing (i) each quantification value obtained for each biological marker of the said combination of at least five distinct biological markers, Step b) of the Method At step b) of the method, for each biological marker used, the value which is obtained at the end of step a) is compared with a reference value for the same biological marker, and when required with reference values for the center of the tumor (CT) and the invasive margin (IM), for the said same biological marker. Said reference value for the same biological marker is thus predetermined and is already known to be indicative of a reference value that is pertinent for discriminating between a low level and a high level of the adaptive immune response of a patient against cancer, for the said biological marker. Said predetermined reference value for said biological marker is correlated with a good cancer prognosis, or conversely is correlated with a bad cancer prognosis.

First Illustrative Embodiment for Predetermining a Reference Value

Each reference value for each biological marker may be predetermined by carrying out a method comprising the steps of:
  a) providing at least one collection of tumor tissue samples selected from the group consisting of:
    i) a collection of tumor tissue samples from cancer patients classified as, Tis, or T1, or T2, or T3 or T4 and N0, or N1, or N2, or N3 and M0 or M1, and with no early metastasis (VE or LI or PI) or with early metastasis, having undergone anti-cancer treatment, and subsequently having no cancer relapse or no cancer recurrence after the anti-cancer treatment;
    ii) a collection of tumor tissue samples from cancer patients classified as Tis, or T1, or T2, or T3 or T4 and N0, or N1, or N2, or N3 and M0 or M1, and With no early metastasis (VE or LI or PI) or with early metastasis, having undergone anti-cancer treatment, and subsequently having cancer relapses or recurrences after the anti-cancer treatment.
  b) quantifying, for each tumor tissue sample comprised in a collection of tumor tissue samples provided at step a), the said biological marker, whereby a collection of quantification values for the said biological marker and for the said collection of tumor tissue samples is obtained;
  c) calculating, from the said collection of quantification values obtained at the end of step b), the mean quantification value for the said biological marker, whereby a predetermined reference value for said biological marker that is correlated with a specific cancer prognosis is obtained.

The "anti-cancer treatment" that is referred to in the definition of step a) above relate to any type of cancer therapy undergone by the cancer patients previously to collecting the tumor tissue samples, including radiotherapy, chemotherapy and surgery, e.g. surgical resection of the tumor.

According to the method for obtaining predetermined reference values above, more than one predetermined reference value may be obtained for a single biological marker. For example, for a single biological marker, the method above allows the determination of at least four predetermined reference values for the same biological marker, respectively one predetermined reference value calculated from the mean quantification value obtained when starting, at step a), with each of the collections (i) and (ii) of tumor tissue samples that are described above.

Second Illustrative Embodiment for Predetermining a Reference Value

Reference values used for comparison at step b) of the method may also consist of "cut-off" values that may be determined as described hereunder.

Each reference ("cut-off") value for each biological marker may be predetermined by carrying out a method comprising the steps of:
  a) selecting a biological marker for which a reference value is to be determined;
  b) providing a collection of tumor tissue samples from cancer patients;
  c) providing, for each tumor sample provided at step b), information relating to the actual clinical outcome for the corresponding cancer patient;
  d) providing a serial of arbitrary quantification values for the said biological marker selected at step a);
  e) quantifying the said biological marker in each tumor tissue sample contained in the collection provided at step b);
  f) classifying the said tumor samples in two groups for one specific arbitrary quantification value provided at step c), respectively:
    (i) a first group comprising tumor samples that exhibit a quantification value for the said marker that is lower than the said arbitrary quantification value contained in the said serial of quantification values;
    (ii) a second group comprising tumor samples that exhibit a quantification value for the said marker that is higher than the said arbitrary quantification value contained in the said serial of quantification values;
  whereby two groups of tumor samples are obtained for the said specific quantification value, wherein the tumors samples of each group are separately enumerated;
  g) calculating the statistical significance between (i) the quantification value for the said biological marker obtained at step e) and (ii) the actual clinical outcome of the patients from which tumor samples contained in the first and second groups defined at step f) derive;
  h) reiterating steps f) and g) until every arbitrary quantification value provided, at step d) is tested;
  i) setting the said reference value ("cut-off" value) as consisting of the arbitrary quantification value for which the highest statistical significance (most significant) has been calculated at step g).

The method above consists of setting a "cut-off" value at the median of the data sets and is fully disclosed in the examples herein.

As it is disclosed above, the said method allows the setting of a single "cut-off" value permitting discrimination between bad and good outcome prognosis. Practically, as it is disclosed in the examples herein, high statistical significance values (e.g. low P values) are generally obtained for a range of successive arbitrary quantification values, and not only for a single arbitrary quantification value. Thus, in one alternative embodiment of the method of determining "cut-off" values above, a minimal statistical significance value (minimal threshold of significance, e.g. maximal threshold P value) is arbitrarily set and the range of arbitrary quantification values for which the statistical significance value calculated at step g) is higher (more significant, e.g. lower P value) are retained, whereby a range of quantification values is provided. The said range of quantification values consist of a "cut-off" value according to the invention. According to this specific embodiment of a "cut-off" value, bad or good clinical outcome prognosis can be determined by comparing, at step b) of the prognosis method of the invention, the value obtained at step a) with the range of values delimiting the said "cut-off" value, for one specific biological marker. In certain embodiments, a cut-off value consisting of a range of quantification values for the considered biological marker, consists of a range of values centered on the quantification value for which the highest statistical significance value is found (e.g. generally the minimum P value which is found).

In certain preferred embodiments of the method for predetermining a cut-off value that is described above, the said biological marker consists of the density of cells expressing a specific protein marker in the tumor sample. Additionally, for a single protein marker, cut-off values for at least two distinct biological markers may be determined, respectively (i) a first cut-off value determined for a first biological marker consisting of the density of cells expressing the said protein marker at the center of to tumor (CT) and (ii) a second cut-off value determined for a second biological marker consisting of the density of cells expressing the said protein marker at the invasive margin (IM).

In certain preferred embodiments of step c) of the method for determining cut-off values above, the said information relating to the actual clinical outcome of the patients are selected from the group consisting of (i) the duration of the disease-free survival (DFS) and (ii) the overall survival (OS).

Indeed, for performing the cancer prognosis method according to the invention, the availability of a predetermined reference value for more than one biological marker is preferred. Thus, generally, at least one predetermined reference value is determined for a plurality of biological markers indicative of the status of the adaptive immune response against cancer that are encompassed herein, by simply reiterating any one of the methods for obtaining predetermined reference values that are described above, for a plurality of biological markers.

For instance, in certain embodiments wherein the biological marker consists, of a surface antigen expressed by cells from the immune system, like the CD3 antigen, and wherein at step a) of the cancer prognosis method a flow cytometry analysis of the CD3+ cell density at the tumor site is carried out, the predetermined reference value may consist of the cell density value, including percentage of specific cells (e.g. CD3+) per total cells or total cell subpopulation (set at 100%), that correlates with bad cancer prognosis, e.g. relapses or recurrences, short survival time, etc., or in contrast may consist of the cell density value that correlates with good cancer prognosis, e.g. no early metastasis, no metastasis at all or long disease-free survival time.

In certain embodiments, the reference predetermined value consists of a "cut-off" value, as already disclosed above, which "cut-off" value consists of a median quantification value for the biological marker of interest that discriminates between bad cancer prognosis and good cancer prognosis. Illustratively, for human colorectal cancer, it has been found that, when using immunohistochemistry analysis of CD3+ cells at the tumor site as the biological marker, the predetermined cut-off reference value may be of about 300 CD3+ cells/mm$^2$ for a tumor tissue sample collected from the center of the tumor, and that the predetermined cut-off reference value may be of about 600 CD3+ cells/mm$^2$ for a tumor tissue sample collected from the invasion margin. In other embodiments wherein the cut-off value consists of a range of values delimiting a low and a high CD3+ quantification values, the said cut-off value optimally ranges from 50 CD3+ cells/mm$^2$ to 1000 CD3+ cells/mm$^2$ for a quantification in the center of the tumor (CT) and from 80 CD3+ cells/mm$^2$ to 1300 CD3+ cells/mm$^2$ for a quantification in the invasive margin (IM).

The optimal cut-off values based on log-rank tests, for CD3, CD8, CD45RO, GZMB cell densities were 370, 80, 80, 30 cells/mm$^2$ in the center of the tumour, respectively, and 640, 300, 190, 60 cells/mm$^2$ in the invasive margin, respectively, as shown in the examples herein.

According to the embodiments above, a bad cancer prognosis is obtained if the quantification value generated for the CD3+ biological marker is less than the predetermined cut-off reference value, when the comparison is carried out at step b) of the method. Conversely, a good cancer prognosis is obtained if the quantification value generated for the CD3+ biological marker is more than the predetermined cut-off reference value, when the comparison is carried out at step b) of the method Third Illustrative Embodiment for Predetermining a Reference Value Also illustratively, in embodiments wherein the biological marker consists of the expression level of a gene related to the immune response of the human body, the predetermined reference value may consist of the gene expression value that correlates with bad cancer prognosis, e.g. relapses or recurrences, short survival time, etc., or in contrast may consist of the gene expression value that correlates with good cancer prognosis, e.g. no metastasis at all or long disease-free survival time. The gene expression value may be expressed as any arbitrary unit. For instance, the gene expression value may be expressed as the difference (deltaCT) between (i) the amount of the biological marker-specific mRNA and (ii) the amount of an unrelated mRNA, found in the tumor tissue sample, such as for example the ribosomal 18S mRNA. Illustratively, for human colorectal cancer, the difference between (i) the amount of the biological marker-specific mRNA and (ii) the amount of an unrelated mRNA may be arbitrarily assigned to consist of the deltaCT and of the mean of all values from the reference group (e.g. for patients undergoing early steps of metastasis processes (VELIPI) and relapses, set to "100%"), In these embodiments, the quantification value generated for a particular gene-specific mRNA, at step a) of the method, is more than 100%, then a better cancer prognosis than with the predetermined reference value is obtained. For instance, this is shown in the examples herein, when using notably CD8α-specific mRNA, GZM-B-specific mRNA and GLNY-specific mRNA.

Comparison(s) Performed at Step b)

As already specified, and as it is shown in the examples herein, step b) of the in vitro prognosis method of the invention consists of comparing, for each biological marker tested, respectively:

(i) the quantification value found at step a) for the said biological marker; and
(ii) the corresponding reference value that is already predetermined for the said biological marker.

When two or more biological markers are quantified at step a), then step b) consists of two or more comparison steps of the kind defined above.

Also, when one specific biological marker is quantified at step a) in various tumor locations, and especially separately both in the center of the tumor (CT) and in the invasive margin (IM), then step b) comprises for the said specific biological marker the same number of comparison steps than the number of tumor locations wherein the said specific biological marker is quantified. Especially for situations wherein a specific biological marker is quantified separately both in CT and IM at step a), then step b) comprises, for the said specific biological marker, two comparison steps, respectively:
  (i) a first comparison step between the quantification value obtained at step a) for the said biological marker in CT, with the predetermined reference value in CT for the said biological marker; and
  (ii) a second comparison step between the quantification value obtained at step a) for the said biological marker in IM, with the predetermines reference value in IM for the said biological marker.

Thus, step b) comprises the same number of single comparison steps than the number of quantification values that are obtained at step a).

The said comparison step b), irrespective of whether step a) consists of step a1) (immunological methods) or step a2) (gene expression analysis) as defined above, preferably also comprises the calculation of a statistical relevance of the plurality of marker quantification values measured at step a), after their comparison With the corresponding reference values, e.g. using a P Log Rank test, as disclosed in the examples herein.

More simply, the said comparison step b) may include a classification of the quantification values measured at step a), for each biological marker, and optionally also for each kind of tumor tissue tested, in two groups, respectively: (i) a first group termed "Hi" when the quantification value for the said biological marker, optionally in the said kind of tumor tissue, is higher than the predetermined corresponding reference value and (ii) a second group termed "Lo" when the quantification value for the said biological marker, optionally in the said kind of tumor tissue, is lower than the predetermined corresponding reference value. It flows that if the result of the comparison step b) consists of exclusively "Hi" values for each marker tested, then a favourable outcome prognosis for the said cancer is determined. Conversely, if the result of the comparison step b) consists of exclusively "Lo" values for each marker tested, then a poor outcome prognosis for the said cancer is determined. Intermediate conclusions are determined for "heterogeneous" patients, wherein, in the comparison step b), "Hi" quantification values are found for one or more of the biological markers tested and "Lo" quantification values are found for the remaining markers of the combination of biological markers tested as it is disclosed in the examples herein.

The inventors believe that a further reason for explaining the high statistical relevance of the in vitro prognosis method according to the invention, for predicting cancer outcome, consists of the size of the patients cohorts that have been tested, which provide highly accurate reference values, e.g. highly accurate "cut-off" values, allowing a reproducible and accurate discrimination between patients with good prognosis and patients with bad prognosis.

Thus, in a most preferred embodiment of the in vitro method according to the invention, the predetermined reference value for each specific biological marker, and optionally the tumor tissue type, that is used at the comparison step b) is calculated on the basis of quantification values for the said marker, and optionally the said marker in the said tumor tissue type, that are previously measured in tumor tissue samples originating from a large population of cancer-bearing individuals.

The accuracy of a specific predetermined reference value increases with the number of tissue samples that are used for obtaining quantification values for a specific biological marker and thus for calculating a mean value (the predetermined reference value) which is associated with a specific cancer outcome. Thus, another explanation for the high accuracy of the in vitro prognosis method according to the invention also resides in the high relevancy of the predetermined reference values, to which are compared the quantification values, at step b) of the method. Most preferably in view of obtaining highly relevant predetermined reference values for each biological marker of interest, the said predetermined reference values consist of the mean value of a plurality of quantification values of the said marker measured on tissue samples originating from the same plurality number of cancer-bearing patients which underwent a specific clinical outcome.

Most preferably, for assessing accurate predetermined reference values, the said reference values are predetermined from at least 50 quantification values, for a specific biological marker, thus using tissue samples originating from at least 50 cancer-bearing patients that have underwent a specific bad or good clinical outcome, e.g. DFS or OFS of more than 5 years following diagnosis. In preferred embodiments, a predetermined reference value is obtained from at least, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 or more quantification values for a specific biological marker.

Illustratively, predetermined reference values disclosed in the examples herein have been obtained from tissue samples originating from a cohort of about 500 cancer-bearing patients The possibility according to the invention to test large cohorts of patients, i.e. a large number of tissue samples, was provided notably by the use of the tissue microarray technique that is detailed further in the present specification.

Specific embodiments of the methods used for performing step b) are fully detailed in the examples herein.

Optional Step c) of the Method

The in vitro cancer prognosis method of the invention may further comprise a step c) wherein the prognosis result per se is provided.

Thus, the cancer, prognosis method of the invention may comprise a further step c) wherein, depending of the biological marker(s) that are used, either:
  (i) a good prognosis of patient for cancer progression is determined, with no cancer relapse or with no cancer recurrence, when the quantification value(s) obtained at step a) for a specific biological marker, or a specific combination of biological markers, is higher than, or lower than, respectively, the corresponding predetermined reference value(s); or
  (ii) a bad prognosis of patient for cancer progression is determined, with cancer relapse or with cancer recurrence, when the quantification value(s) obtained at step a) for a specific biological marker, or a specific combination of biological markers, is higher than, or lower than, the said corresponding predetermined reference value(s);

Alternatively, the cancer prognosis method of the invention may comprise a further step c) wherein, depending of the biological marker(s) used, either:
  (i) a good prognosis of patient for cancer progression is determined, with high disease-free survival (DFS) value or high overall survival (OS) value, when the quantification value(s) obtained at step a) for a specific biological marker, or a specific combination of biological markers, is higher than, or lower than, the corresponding predetermined reference value(s); or (ii) a bad prognosis of patient for cancer progression is determined, with low disease-free survival (DFS) value or low overall survival (OS) value, when the quantification value(s) obtained at step a) for a specific biological marker, or a specific combination of biological markers, is lower than, or higher than, respectively, the said corresponding predetermined reference value(s);

Usually, for most of the biological markers used herein, the quantification value increases with an increase of the adaptive immune response against cancer. For instance, when the biological marker that is quantified at step a) consists of a protein or a gene specifically expressed by cells of the immune system, the quantification value of said marker increases with the level of the adaptive immune response against cancer of the patient tested. Thus, when performing step b) of the cancer prognosis method of the invention, a good prognosis is determined when the quantification value for a specific biological marker that is obtained at step a) is higher than the corresponding predetermined reference value, notably in embodiments wherein the predetermined reference value consists of a cut-off value. Conversely, a bad prognosis is determined when the quantification value obtained at step a) for a specific biological marker is lower than the corresponding predetermined reference value, notably in embodiments wherein the predetermined reference value consists of a cut-off value.

Specific embodiments of the methods used for performing step c) are fully detailed in the examples herein.

Combinations of biological Markers

When performing the cancer prognosis method of the invention with more than one biological marker, the number of distinct biological markers that are quantified at step a) are usually of less than 100 distinct markers, and in most embodiments of less than 50 distinct markers.

Advantageously, when high throughput screening of samples is sought, the cancer prognosis method of the invention is performed by using up to 20 distinct biological markers.

The higher number of distinct biological markers are quantified at step a) of the method, the more accurate the final cancer prognosis will be.

The number of distinct biological markers that is necessary for obtaining an accurate and reliable cancer prognosis, using the in vitro prognosis method of the invention, may vary notably according to the type of technique for quantification which is performed at step a).

Illustratively, high statistical significance was found with a combination of a small number of biological markers, when step a) is performed by in situ immunohistochemical detection of protein markers of interest, provided that separate quantification of the said markers are performed both in the center of the tumor (CT) and in the invasive margin (IM). Illustratively, high statistical significance was obtained with a combination of two to ten biological markers, as disclosed in the examples herein. Without wishing to be bound by any particular theory, the inventors believe that highly statistical relevance (P value lower than $10^{-3}$) for cancer prognosis is reached when step a) is performed by using an immunohistochemical method for biological marker quantification, and by using a combination of three distinct biological markers, or more.

Further illustratively, high statistical significance was also found with a small number of biological markers, when step a) is performed by gene expression analysis of gene markers of interest, although the gene expression analysis technique is performed on the whole tumor sample. Illustrative embodiments of various highly significant combination of two gene markers are provided notably in Table 4. Without wishing to be bound by any particular theory, the inventors believe that highly statistical relevance (P value lower than $10^{-3}$) is reached when step a) is performed by using a gene expression analysis for biological marker quantification, and by using a combination of ten distinct biological markers, and more preferably a combination of fifteen distinct biological markers, most preferably twenty distinct biological markers, or more.

As it is shown in the examples herein, a reliable cancer prognosis may be obtained when quantifying a single biological marker at step a) of is the method, as it is illustrated, for example, with quantification of CD3+, CD8+, CD45RO, GZM-B, GLNY, TBX21, IRF1, IFNG, CXCL9 and CXCL10 biological markers.

Thus, in preferred embodiments of the cancer prognosis method according to the invention, the tumor tissue sample that is referred to in step a) is selected from the group consisting of (i) a global primary tumor (as a whole), (ii) a tissue sample from the center of the tumor, (iii) a tissue sample from the tissue directly surrounding the tumor which tissue may be more specifically named the "invasive margin" of the tumor, (iv) the lymph nodes located at the closest proximity of the tumor, (v) a tumor biopsie perform prior surgery (for follow-up of patients after treatment for example), and (vi) a distant metastasis.

Most preferably, when the in vitro prognosis method of the invention is performed with biological markers consisting of the densities of cells expressing specific proteins, then step a) is performed through immunohistochemical techniques and cell densities are measured (i) in the center of the tumor (CT), (ii) in the invasive margin (IM) or (iii) separately both in the CT and in the IM.

Most preferably, when the in vitro prognosis method of the invention is performed with biological markers consisting of the expression level of genes of interest, then step a) is performed through gene expression analysis methods, like real-time Taqman PCR analysis, starting from the whole tumor tissue that was initially collected from the cancer patient, e.g. tumor tissue originating from a tumor resection during a surgical operation.

Preferably, the at least one biological marker indicative of the status of the adaptive immune response of said patient against cancer, that is quantified at step a), consists of at least one biological marker expressed by a cell from the immune system selected from the group consisting of B lymphocytes, T lymphocytes, monocytes/macrophages, dendritic cells, NK cells, NKT cells, and NK-DC cells.

Preferably, said at least one biological marker, that is quantified at step a), is selected from the group consisting of:

(i) the number or the density of cells from the immune system contained in the tumor tissue sample and that express the said biological marker, generally a protein marker; and (ii) the expression level of a nucleic acid of interest in the tumor tissue sample, generally the amount of mRNA encoded by a specific gene marker.

In certain embodiments of the method, said at least one biological marker consists of the density of T lymphocytes present at the tumor site.

In certain other embodiments, said at least one biological marker consists of the quantification value of a protein expressed by cells from the immune system present at the tumor site.

In further embodiments of the method, said at least one biological marker consists of the quantification value of the expression of gene specifically expressed by cells from the immune system present at the tumor site.

A list of the preferred biological markers that, may be used for carrying out the cancer prognosis method of the invention are listed in Tables 2, 4, 8, 9 and 10. Tables 2, _9 and 10 contain, for each biological marker that is listed, the accession number to its nucleic acid and amino acid sequences, as available in the GenBank International database.

Although the cancer prognosis method according to the invention has been tested for colorectal cancer, said method may be applied for a wide variety of cancers. Without wishing to be bound by any particular theory, the inventors believe that the cancer prognosis method of the invention may be successfully carried out for prognosing the progression of any cancer that develops from a central tumor to which cells from the immune system have access.

Thus, the cancer prognosis method according to the invention is potentially useful for determining the prognosis of patients for progression of a cancer selected from the group consisting of adrenal cortical cancer, anal cancer, bile duct cancer (e.g. periphilar cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating, lobular carcinoma, lobular carcinoma in, situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinroma, clear cell), esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma).

In yet further embodiments of the method, said at least one biological marker is selected from the group consisting of the following biological markers:

(i) Various Biological Markers

ICAM-2/CD102, 4-1BB/TNFRSF9, IFN-gamma R1, IFN-gamma R2, B7-1/CD80, IL-1 RI, IL-2 R alpha, BLAME/SLAMF8, IL-2 R beta, CCR3, CCR4, CCR5, CCR6, CCR7, CCR8, IL-7 R alpha, CCR9, CXCR1/IL-8 RA, CD2, CD3epsilon, CD3zeta, CD3gamma, CD4, CD4+/45RA-, IL-12 R beta 1, CD4+/45R0-, IL-12 R beta 2, CD4+/CD62L-ICD44, CD4+/CD62L+/CD441L-17, CD5, Integrin alpha 4/CD49d, CD6, Integrin alpha E/CD103, CD8, Integrin alpha M/CD11b, CD8+/45RA-, Integrin alpha X/CD11c, CD8+/45RO-, Integrin beta 21CD18, CD27/TNFRSF7, LAG-3, CD28, LAIR1, CD30/TNFRSF8, LAIR2, CD31/PECAM-1, CD40 Ligand/TNFSF5, NCAM-L1, CD43, NTB-A/SLAMF6, CD45, CD83, CD84/SLAMF5, RANK/TNFRSF11A, L-Selectin, CD229/SLAMF3, SIRP beta 1, CD69, SLAM, Common gamma Chain/IL-2 R gamma, CRACC/SLAMF7, CX3CRI, CXCR3, CXCR4, CXCR6, TNF RI/TNFRSF1A, TNF RII/TNFRSF1B, Fas/TNFRSF6, Fas Ligand/TNFSF6, TSLP, TSLP R, ICAM-11CD54, IL-2, IFN-gamma, IL4, IL-5, IL-10, IL-13, (ii) Biological Markers of Th 1/Th2 Cells:

II-2R Common beta Chain, Common gamma Chain/IL-2 R gamma, IFN-gamma, IFN-gamma R1, IL-12, IFN-gamma R2, IL-12 R beta 1, IL-2, IL-12 R beta 2, IL-2 R alpha, IL-2 R beta, IL-24, TNF RI/TNFRSF1A, TNF RII/TNFRSF1B, IL-4 R, TNF-beta/TNFSF1B, (iii) Biological Markers of the Interferon Family:

IFN alpha, IFN beta, IFN-alpha/beta R1, IFN-alpha/beta R2, IFN-gamma R1, IFN-gamma R2, IFN-alpha A, IFN-alpha/beta R2, IFN-alpha B2, IFN-beta, IFN-alpha C, IFN-gamma, IFN-alpha D, IFN-alpha G, IFN-omega, IFN-alpha H2, (iv) Biological Markers of the Common Gamma Chain Receptor Family:

Common gamma Chain/IL-2 R gamma, IL-7 R alpha, IL-2, IL-9, IL-2 R alpha, IL-9 R, IL-2 R beta, IL-15, IL-15 R alpha, IL-21, IL-7, IL-21 R, IL-31, (v) Biological Markers of the CX3C Chemokines & Receptors:

CX3C Chemokine Ligands, CX3CL1/Fractalkine,
CX3C Chemokine receptors, CX3CR1, (vi) Biological Markers of CXC Chemokines & Receptors, CXC Chemokine Ligands, CXCL13/BLC/BCA-1, CXCL11/I-TAC, CXCL14/BRAK, CXCL8/IL-8, CINC-1, CXCL10/IP-10/CRG-2, CINC-2, CINC-3, CXCL16, CXCL15/Lungkine, CXCL5/ENA, CXCL9/MIG, CXCL6/GCP-2, CXCL7/NAP-2, GRO, CXCL4/PF4, CXCL1/GRO alpha, CXCL12/SDF-1, CXCL2/GRO beta, Thymus Chemokine-1, CXCL3/GRO gamma, CXC Chemokine Receptors, CXCR6, CXCR3, CXCR1/IL-8 RA, CXCR4, CXCR2/IL-8 RB, CXCR5, (vii) Biological Markers of CC Chemokines & Receptors, CC Chemokine Ligands, CCL21/6Ckine, CCL12/MCP-5, CCL61C10, CCL22/MDC, CCL28, CCL3L1/MIP-1 alpha Isoform LD78 beta, CCL27/CTACK, CCL3/MIP-1 alpha, CCL24/Eotaxin-2, CCL4/MIP-1 beta, CCL26/Eotaxin-3, CCL15/MIP-1 delta, CCL11/Eotaxin, CCL9/10/MIP-1 gamma, CCL14a/HCC-1, MIP-2, CCL14b/HCC-3, CCL19/MIP-3 beta, CCL16/HCC4, CCL20/MIP-3 alpha, CCL1/I-309/TCA-3, CCL23/MPIF-1, MCK-2, CCL18/PARC, CCL2/MCP-1, CCL5/RANTES, CCL8/MCP-2, CCL17/TARC, CCL7/MCP-3/MARC, CCL25/TECK, CCL13/MCP-4CC Chemokine Receptors, CCR1, CCR7, CCR2, CCR8, CCR3, CCR9, CCR4, D6, CCR5, HCR/CRAM-A/B, CCR6

(viii) Biological Markers of CC Chemokine Inhibitors

CCI, CC Viral Chemokine Homologs, MCV-type II, MIP-II, MIP-I, MIP-III (ix) Biological Markers of C Chemokines & Receptors The C (gamma) subfamily lacks the first and third cysteine residues. Lymphotactin (also known as SCM-1 alpha) and SCM-1 beta are currently the only two family members. Both have chemotactic activity for lymphocytes and NK cells.

C Chemokine Ligands, XCL1/Lymphotactin
C Chemokine Receptors, XCRI (x) Biological Markers of other Interleukins
IL-12, IL-12 R beta 1, IL-12 R beta 2, IL-27, IL-15, IL-31

In the present specification, the name of each of the various biological markers of interest refers to the internationally recognised name of the corresponding gene, as found in internationally recognised gene sequences and protein sequences databases, including in the database from the HUGO Gene Nomenclature Committee, that is available notably at the following Internet address:

http://www.gene.ucl.ac.uk/nomenclature/index.html

In the present specification, the name of each of the various biological markers of interest may also refer to the internationally recognised name of the corresponding gene, as found in the internationally recognised gene sequences and protein sequences database Genbank.

Through these internationally recognised sequence databases, the nucleic acid and the amino acid sequences corresponding to each of the biological marker of interest described herein may be retrieved by the one skilled in the art.

In yet further embodiments of the method, as already mentioned above, quantification values for a combination of biological markers are obtained at step a) of the cancer prognosis method of the invention.

Thus, the cancer prognosis method of the invention may be performed with a combination of biological markers. The number of biological markers used is only limited by the number of distinct biological markers of interest that are practically available at the time of carrying out the method. However, a too much high number of biological markers will significantly increase the duration of the method without simultaneously significantly improving the final prognosis determination.

Usually, in the embodiments wherein the cancer prognosis method of the invention is performed with a combination of biological markers, not more than 50 distinct biological markers are quantified at step a). In most embodiments, a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50 distinct biological markers are quantified, However, as already mentioned previously in the present specification, the number of combined markers that are required for reaching a high statistical relevance (e.g. P lower than $10^{-3}$), will be depending from the kind of technique for quantifying the said combination of biological markers, at step a) of the in vitro prognosis method.

In certain embodiments of the in vitro prognosis method of the invention, wherein step a) is performed by quantifying biological markers with immunohistochemical techniques, then the use of a combination of a low number of markers may be sufficiently informative, specifically if the biological markers are separately quantified both in the center of the tumor (CT) and in the invasive margin (IM).

In certain other embodiments of the in vitro prognosis method of the invention, wherein step a) is performed by quantifying biological markers with gene expression analysis techniques, then the use of a combination of a higher number of markers is generally required, for example at least about 10 distinct biological markers.

In still further embodiments of the method, the said at least one biological marker is selected from the group consisting of CD3, CD8, GZMB, CD45RO, GLNY, TBX21, IRF1, IFNG, CXCL9, CXCL10, CD4, CXCR3, CXCR6, IL-18, IL-18Rbeta, Fractalkine, IL-23, IL-31, IL-15, IL-7, MIG, Perforin, TCRαβ, TCRγδ, LAT, ZAP70, CD5 and CD2. These biological markers are preferably quantified, at step a) of the in vitro prognosis method of the invention, by immunochemical methods, including in situ immunohistochemical methods. The quantification values may be expressed as the mean density of cells expressing a marker protein of interest contained per surface area of a tissue section from the tumor tissue sample.

Illustratively, a combination of 2, 3, 4, 5, 6, 7, 8, 9, 10, 11, 12, 13, 14, 15, 16, 17, 18, 19, 20, 21, 22, 23, 24, 25, 26, 27, or 28 distinct biological markers are quantified at step a), which biological markers are selected from the group consisting of CD3, CD8, GZMB, CD45RO, GLNY, TBX21, IRF1, IFNG, CXCL9, CXCL10, CD4, CXCR3, CXCR6, IL-18, IL-18Rbeta, Fractalkine, IL-23, IL-31, IL-15, IL-7, MIG, Perforin, TCRαβ, TCRγδ, LAT, ZAP70, CD5 and CD2 Quantification of this group of biological markers is preferably performed, at step a) of the in vitro prognosis method of the invention, with immunohistochemical techniques.

Yet illustratively, a combination of 2 or more distinct biological markers which may be quantified at step a) of the in vitro prognosis method of the invention may be selected 2 or more biological markers that are selected from the group consisting of CCR5, CR7, CD103, CD119, CD120a, CD120b, CD122, CD127, CD134, CD14, CD152, CD154, CD178, CD183, CD184, CD19, CD1a, CD210, CD25, CD26, CD27, CD28, CD3, CD32, CD4, CD44, CD45, CD45Ra, CD45Ro, CD47, CD49d, CD5, CD54, CD56, CD62L, CD69, CD7, CD8, CD80, CD83, CD86, CD95, CD97, CD98, CXCR6, GITR, HLA-DR, ICOS, IFNγRII, IL-18Rα, KIR-NKAT2, PD1, TCRαβ and TGFRII. Quantification of this group of biological markers is preferably performed, at step a) of the in vitro prognosis method of the invention, with immunohistochemical techniques. A list of antibodies directed specifically against each of these marker proteins is contained in Table 3 herein.

Still further, combinations of at least two biological markers encompass combinations of two or more distinct biological markers selected from the group of biological comprising the following biological markers: T-box transcription factor 21 (T-bet), interferon regulatory factor 1 (IRF-1), IFNγ, CD3ζ, CD8, granulysin (GLNY) and granzyme B (GZMB). Quantification of this group of biological markers is preferably performed, at step a) of the in vitro prognosis method of the invention, with immunohistochemical techniques.

Illustratively, the combination of two biological markers may be selected from the group consisting of CD8A-TBX21, CD3Z-CD8A, CD3Z-TBX21, B7H3-TGFB1, IFNG-TBX21, CD4-CD8A, CD8A, IFNG, CD4-TBX21, CD3Z-CD4, CD4-TGFB1, CD8A-GLNY, IFNG-IRF1, GLNY-IFNG, IRF1-TBX21, IL8-PTGS2, GLNY-TBX21, CD3Z-GLNY, CD3Z-IFNG, GZMB-IFNG, GLNY-IRF1, IL10-TGFB1, CD8A-IL10, CD4-IL10, CD8A-GZMB, GZMB-TBX21, GD3Z-GZMB, CD4-tRFI, GNLY-GZMB, B7H3-IL10, CD4-GZMB, GZMB-IRF1, IL10-TBX21, CD4-IFNG, B7H3-CD4, CD8A-TGFB1, CD3Z-IL10 and CD4-GNLY. Quantification of this group of biological markers is preferably performed, at step a) of the in vitro prognosis method of the invention, with gene expression analysis techniques.

Other combinations of two biological markers that may be used, optionally with one or more distinct biological markers, are listed in Table 4 herein. Quantification of this group of biological markers is preferably performed, at step a) of the in vitro prognosis method of the invention, with gene expression analysis methods.

Further combinations of at least two markers that may be used, optionally with one or more distinct biological markers, are listed in Table 8 herein. Quantification of this group of biological markers is preferably performed, at step a) of the in vitro prognosis method of the invention, with gene expression analysis methods.

Still further, combinations of at least two biological markers encompass combinations of two or more distinct biological markers selected from the group of biological markers that are listed in Table 9 herein, comprising the following biological markers: 18s, ACE, ACTB, AGTR1, AGTR2, APC, APOA1, ARF1, AXIN1, BAX, BCL2, BCL2L1, CXCR5, BMP2, BRCA1, BTLA, C3, CASP3, CASp9, CCL1, CCL11, CCL13, CCL16, CCL17, CCL18, CCL19, CCL2, CCL20, CCL21, CCL22, CCL23, CCL24, CCL25, CCL26, CCL27, CCL28, CCL3, CCL5, CCL7, CCL8, CCNB1, CCND1, CCNE1, CCR1, CCR10, CCR2, CCR3, CCR4, CCR5, CCR6, CCR7, CCR8, CCR9, CCRL2, CD154, CD19, CD1a, CD2, CD226, CD244, PDCD1LG1, CD28, CD34, CD36, CD38, CD3E, CD3G, CD3Z, CD4, CD40LG, CD5, CD54, CD6, CD68, CD69, CLIP, CD80, CD83, SLAMF5, CD86, CD8A, CDH1, CDH7, CDK2, CDK4, CDKN1A, CDKN1B, CDKN2A, CDKN2B, CEACAM1, COL4A5, CREBBP, CRLF2, CSF1, CSF2, CSF3, CTLA4, CTNN81, CTSC, CX3CL1, CX3CRI, CXCL1, CXCL10, CXCL11, CXCL12, CXCL13, CXCL14, CXCL16, CXCL2, CXCL3, CXCL5, CXCL6, CXCL9, CXCR3, CXCR4, CXCR6, CYP1A2, CYP7A1, DCC, DCN, DEFA6, DICER1, DKK1, Dok-1, Dok-2, DOK6, DVL1, E2F4, EBI3, ECE1, ECGF1, EDN1, EGF, EGFR, EIF4E, CD105, ENPEP, ERBB2, EREG, FCGR3A, CGR3B, FN1, FOXP3, FYN, FZD1, GAPD, GLI2, GNLY, GOLPH4, GRB2, GSK3B, GSTP1, GUSB, GZMA, GZMB, GZMH, GZMK, HLA-B, HLA-C, HLA-, MA, HLA-DMB, HLA-DOA, HLA-DOB, HLA-DPA1, HLA-DQA2, HLA-DRA, HLX1, HMOX1, HRAS, HSPB3, HUWE1, ICAM1, ICAM-2, ICOS, ID1, ifna1, ifna17, ifna2, ifna5, ifna6, ifna8, IFNAR1, IFNAR2, IFNG, IFNGR1, IFNGR2, IGF1, IHH, IKBKB, IL10, IL12A, IL12B, IL12RB1, IL12RB2, IL13, IL13RA2, IL15, IL15RA, IL17, IL17R, IL17RB, IL18, IL1A, IL1B, IL1RI, IL2, IL21, IL21R, IL23A, IL23R, IL24, IL27, IL2RA, IL2RB, IL2RG, IL3, IL31RA, IL4, IL4RA, IL5, IL6, IL7, IL7RA, IL8, CXCR1, CXCR2, IL9, IL9R, IRF1, ISGF3G, ITGA4, ITGA7, integrin, alpha E (antigen CD103, human mucosal lymphocyte, antigen 1; alpha polypeptide), Gene hCG33203, ITGB3, JAK2, JAK3, KLRB1, KLRC4, KLRF1, KLRG1, KRAS, LAG3, LAIR2, LEF1, LGALS9, LILRB3, LRP2, LTA, SLAMF3, MADCAM1, MADH3, MADH7, MAF, MAP2K1, MDM2, MICA, MICB, MKI67, MMP12, MMP9, MTA1, MTSS1, MYC, MYD88, MYH6, NCAM1, NFATC1, NKG7, NLK, NOS2A, P2X7, PDCD1, PECAM-, CXCL4, PGK1, PIAS1, PIAS2, PIAS3, PIAS4, PLAT, PML, PP1A, CXCL7, PPP2CA, PRF1, PROM1, PSMB5, PTCH, PTGS2, PTP4A3, PTPN6, PTPRC, RAB23, RAC/RHO, RAC2, RAF, RB1, RBL1, REN, Drosha, SELE, SELL, SELP, SERPINE1, SFRP1, SIRP beta 1, SKI, SLAMF1, SLAMF6, SLAMF7, SLAMF8, SMAD2, SMAD4, SMO, SMOH, SMURF1, SOCS1, SOCS2, SOCS3, SOCS4, SOCS5, SOCS6, SOCS7, SOD1, SOD2, SOD3, SOS1, SOX17, CD43, ST14, STAM, STAT1, STAT2, STAT3, STAT4, STAT5A, STAT5B, STAT6, STK36, TAP1, TAP2, TBX21, TCF7, TERT, TFRC, TGFA, TGFB1, TGFBR1, TGFBR2, TIMP3, TLR1, TLRO1, TLR2, TLR3, TLR4, TLR5, TLR6, TLR7, TLR8, TLR9, TNF, TNFRSF10A, TNFRSF11A, TNFRSF18, TNFRSF1A, TNFRSF1B, OX-40, TNFRSF5, TNFRSF6, TNFRSF7, TNFRSF8, TNFRSF9, TNFSF10, TNFSF6, TOB1, TP53, TSLP, VCAM1, VEGF, WIF1, WNT1, WNT4, XCL1, XCR1, ZAP70 and ZIC2 Quantification of this group of biological markers is preferably performed, at step a) of the in vitro prognosis method of the invention, with gene expression analysis methods.

Yet further preferred combinations of at least two biological markers encompass combinations of two or more distinct biological markers selected from the group comprising the following biological markers: TNFRSF6B, CEACAM1, PDCD1LG1, CD8A, PTGS2, BIRC5, SELL, INDO, IRAK4, TNF, TNFRSF10A, MMP7, LILRB3, CD3Z, TNFRSF8, GAPD, CXCL10, EBAG9, IL8, STAT1, CXCR3, TGFB1, ICOS, CXCL9, CD97, IL18RAP, CXCR6, ART1, IRF1, B7H3, ACE, IL18R1, TBX21, IL18, PDCD1, IFNG, GNLY, GATA3, VEGF, GZMB, LAT, CD4, IRTA2, IL10, TNFSF4, THSD1 and PDCDILG2. Quantification of this group of biological markers is preferably performed, at step a) of the in vitro prognosis method of the invention, with gene expression analysis methods.

Any combination of at least two biological markers selected from the group of biological markers that are described in the present specification are herein encompassed by the invention.

In certain embodiments of the method, a combination of two biological markers is used at step a), that may be also termed herein a "set" of biological markers.

A specific set of biological markers, that may be quantified through gene expression analysis techniques, consists of the set consisting of the following biological markers: PDCDILG1, VEGF, TNFRSF6B, IRF1, IL8RA and SELL. The said set of biological markers is of a high statistical relevance, as disclosed in the examples herein.

General Methods for Quantifying Biological Markers

Any one of the methods known by the one skilled in the art for quantifying cellular types, a protein-type or an nucleic acid-type biological marker encompassed herein may be used for performing the cancer prognosis method of the invention. Thus any one of the standard and non-standard (emerging) techniques well known in the art for detecting and quantifying a protein or a nucleic acid in a sample can readily be applied.

Such techniques include detection and quantification of nucleic acid-type biological markers with nucleic probes or primers.

Such techniques also include detection and quantification of protein-type biological markers with any type of ligand molecule that specifically binds thereto, including nucleic acids (e.g. nucleic acids selected for binding through the well known Selex method), and antibodies including antibody fragments. In certain embodiments wherein the biological marker of interest consists of an enzyme, these detection and quantification methods may also include detection and quantification of the corresponding enzyme activity.

Noticeably, antibodies are presently already available for most, if not all, the biological markers described in the present specification, including those biological markers that are listed in Table 2.

Further, in situations wherein no antibody is yet available for a given biological marker, or in situations wherein the production of further antibodies to a given biological marker is sought, then antibodies to said given biological markers may be easily obtained with the conventional techniques, including generation of antibody-producing hybridomas. In this method, a protein or peptide comprising the entirety or a segment of a biological marker protein is synthesized or isolated (e.g. by purification from a cell in which it is expressed or by transcription and translation of a nucleic acid encoding the protein or peptide in vivo or in vitro using known methods), A vertebrate, preferably a mammal such as a mouse, rat, rabbit, or sheep, is immunized using the protein or peptide. The vertebrate may optionally (and preferably) be immunized at least one additional time with the protein or peptide, so that the vertebrate exhibits a robust immune response to the protein or peptide. Splenocytes are isolated from the immunized vertebrate and fused with an immortalized cell line to form hybridomas, using any of a variety of methods well known in the art. Hybridomas formed in this manner are then screened using standard methods to identify one or more hybridomas which produce an antibody which specifically binds with the biological marker protein or a fragment thereof. The invention also encompasses hybridomas made by this method and antibodies made using such hybridomas. Polyclonal antibodies may be used as well.

Expression of a biological marker of the invention may be assessed by any of a wide variety of well known methods for detecting expression of a transcribed nucleic acid or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In one preferred embodiment, expression of a marker is assessed using an antibody (e.g. a radio-labeled, chromophore-labeled, fluorophore-labeled, polymer-backbone-antibody, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a marker protein or fragment thereof, including a marker protein which has undergone all or a portion of its normal post-translational modification.

In another preferred embodiment, expression of a marker is assessed by preparing mRNA/cDNA (i.e. a transcribed polynucleotide) is from cells in a patient tumor tissue sample, and by hybridizing the mRNA/cDNA with a reference polynucleotide which is a complement of a marker nucleic acid, or a fragment thereof. cDNA can, optionally, be amplified using any of a variety of polymerase chain reaction methods prior to hybridization with the reference polynucleotide; preferably, it is not amplified.

In a related embodiment, a mixture of transcribed polynucleotides obtained from the sample is contacted with a substrate having fixed thereto a polynucleotide complementary to or homologous with at least a portion (e.g. at least 7, 10, 15, 20, 25, 30, 40, 50, 100, 500, or more nucleotide residues) of a biological marker nucleic acid. If polynucleotides complementary to or homologous with are differentially detectable on the substrate (e.g. detectable using different chromophores or fluorophores, or fixed to different selected positions), then the levels of expression of a plurality of markers can be assessed simultaneously using a single substrate (e.g. a "gene chip" microarray of polynucleotides fixed at selected positions). When a method of assessing marker expression is used which involves hybridization of one nucleic acid with another, it is preferred that the hybridization be performed under stringent hybridization conditions.

An exemplary method for detecting and/or quantifying a biological marker protein or nucleic acid in a tumor tissue sample sample involves obtaining a tumor tissue sample (e.g. (i) a global primary tumor (as a whole), (ii) a tissue sample from the center of the tumor, (iii) a tissue sample from the tissue directly surrounding the tumor which tissue may be more specifically named the "invasive margin" of the tumor, (iv) the lymph nodes located at the closest proximity of the tumor, (v) a tumor biopsie perform prior surgery (for follow-up of patients after treatment for example), and (vi) a distant metastasis, from a cancer patient. Said method includes further steps of contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a tumor tissue sample in vitro. For example, in vitro techniques for detection of mRNA include Northern hybridizations and in situ hybridizations. In vitro techniques for detection of a biological marker protein include enzyme linked immunosorbent assays (ELISAs), Western blots, immunoprecipitations and immunofluorescence. Furthermore, in vivo techniques for detection of a marker protein include introducing into a subject a labeled antibody directed against the protein or fragment thereof. For example, the antibody can be labeled with a radioactive marker whose presence and location in a subject can be detected by standard imaging techniques.

A general principle of such detection and/or quantification assays involves preparing a sample or reaction mixture that may contain a biological marker, and a probe, under appropriate conditions and for a time sufficient to allow the marker and probe to interact and bind, thus forming a complex that can be removed and/or detected in the reaction mixture.

As used herein, the term "probe" refers to any molecule which is capable of selectively binding to a specifically intended target molecule, for example, a nucleotide transcript or protein encoded by or corresponding to a biological marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

These detection and/or quantification assays of a biological marker can be conducted in a variety of ways.

For example, one method to conduct such an assay would involve anchoring the probe onto a solid phase support, also referred to as a substrate, and detecting target marker/probe complexes anchored on the solid phase at the end of the reaction. In one embodiment of such a method, a sample from a subject, which is to be assayed for quantification of the biological marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. A FRET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, Anal. Chem. 63:2338-2345 and Szabo et al., 1995, Curr. Opin. Struct. Biol. 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to, differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, Trends Biochem Sci. 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, J. Mol. Recognit. Winter 11(1-6):141-8; is Hage, D. S., and Tweed, S. A. J Chromatogr B Biomed Sci Appl 1997 Oct. 10; 699(1-2):499-525). Gel electrophoresis may also be employed to separate complexed assay components from unbound components (see, e.g., Ausubel et al., ed., Current Protocols in Molecular Biology, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. SELDI-TOF technique may also be employed on matrix or beads coupled with active surface, or not, or antibody coated surface, or beads.

Appropriate conditions to the particular assay and components thereof will be well known to one skilled in the art.

In a particular embodiment, the level of marker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from colorectal cancer (see, e.g., Ausubel et al., ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the prognostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA marker in a sample involves the process of nucleic acid amplification, e.g., by rtPCR (the experimental embodiment set forth in Mullis, 1987, U.S. Pat. No. 4,683,202), ligase chain reaction (Barany, 1991, Proc. Natl. Acad. Sci. USA, 88:189-193), self sustained sequence replication (Guatelli et al., 1990, Proc. Natl. Acad. Sci. USA 87:1874-1878), transcriptional amplification system (Kwoh et al., 1989, Proc. Natl. Acad. Sci. USA 86:1173-1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the colorectal cancer prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, ribosomal 18S gene, GAPD gene, or epithelial cell-specific genes. This normalization allows the comparison of the expression level in one sample, e.g., a patient sample, to another sample, e.g., a non-colorectal cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

As already mentioned previously in the present specification, one preferred agent for detecting and/or quantifying a biological marker protein when performing the cancer prognosis method of the invention is an antibody that specifically bind to such a biological marker protein or a fragment thereof, preferably an antibody with a detectable label. Antibodies can be polyclonal, or more preferably, monoclonal. An intact antibody, or a fragment or derivative thereof (e.g., Fab or F(ab').sub.2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

A variety of formats can be employed to determine whether a sample contains a biological marker protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection and/or quantification methods for use in the cancer prognosis method according to the invention.

In one format, antibodies, or antibody fragments or derivatives, can be used in methods such as Western blots, SELDI-TOF (carried out with antibody-beads coupled or matrix) or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from colorectal cancer can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

The most preferred methods for quantifying a biological marker for the purpose of carrying out the cancer prognosis method of the invention are described hereunder.

Quantifying Biological Markers by Tissue Microarray

In certain embodiments, a biological marker, or a set of biological markers, may be quantified with any one of the Tissue Microarray methods known in the art.

Tissue microarrays are produced by a method of re-locating tissue from conventional histologic paraffin blocks such that tissue from multiple patients or blocks can be seen on the same slide. This is done by using a needle to biopsy a standard histologic sections and placing the core into an array on a recipient paraffin block. This technique was originally described by Wan in 1987 (Wan, Fortuna and Furmanski; Journal of Immunological Methods). In certain embodiments of Tissue microarrays, tissue cores are placed in specific spatially fixed positions in a block. The technique is disclosed notably by Kononen et al. (Nature Medicine in 1998).

The tissue array technique involves acquiring small, minimal cylindrical samples from paraffin embedded tissue specimens. These cylinders are then arrayed in a systematic, high-density grid into another paraffin block.

For instance, tumor tissue samples, including under the form of biopsy samples (i) of the center of the tumor, (ii) of the invasion margin or (iii) of the regional lymph nodes, are obtained from an appropriate number of individuals, formalin-fixed, paraffin-embedded tumor tissue blocks. These are transferred to a TMA block. Multiple TMA blocks can be generated at the same time. Each TMA block can be sectioned up to 300 times, with all resulting TMA slides having the same tissues in the same coordinate positions. The individual slides can be used for a variety of molecular analyses, such as H&E staining to ascertain tissue morphology, mRNA in situ hybridization, protein immunohistochemistry, or analysis of DNA for genetic alteration.

Because these cylindrical tumor tissue samples are small (0.4-1 mm diameter×3-4 mm in height), up to a thousand tissues can be arrayed in a single paraffin block while minimizing the damage and tissue requirement. Furthermore, these paraffin blocks can be transversely cut into hundreds of tissue microarray sections, which can then each be used for different genetic analyses.

In addition to the increased speed of analyses, tissue microarrays may also ensure the reproducibility and reliability of the cancer prognosis method according to the invention, because the hundreds of different tissue samples are handled, prepared, and stained in a parallel, virtually identical manner all on the same slide (Kallioniemi, O.; Wagner, U.; Kononen, J. and Sauter, G. Tissue microarray technology for high-throughput molecular profiling of cancer, Human Molecular Genetics (2001), 10, 657-662.).

Typically, representative areas of the tumor are removed from paraffin-embedded tumor tissue blocks, whereby tumor tissue samples are obtained. Then, said tumor tissue samples are transferred to another recipient paraffin block where these samples are spotted. Then, the tissue sample spots that are arrayed in said recipient paraffin block are cut into thin sections, typically 2-5 µm sections, for further analysis.

Typically, for further analysis, one thin section of the array, namely the Tissue Microarray, is firstly incubated with labeled antibodies directed against one biological marker of interest. After washing, the labeled antibodies that are bound to said biological marker of interest are revealed by the appropriate technique, depending of the kind of label is borne by the labeled antibody, e.g. radioactive, fluorescent or enzyme label. Multiple labeling can also be performed simultaneously, especially in embodiments wherein more than one protein-specific antibody is used, for the purpose of quantifying more than one biological marker.

Illustrative embodiments of quantification of biological markers using Tissue Microarrays are disclosed in the examples herein.

Quantifying Biological Markers by Immunohistochemistry on Conventional Tissue Slides (Paraffin-Embedded or Frozen Specimens)

In certain embodiments, a biological marker, or a set of biological markers, may be quantified with any one of the immunohistochemistry methods known in the art.

Analysis can then performed on (i) a global primary tumor (as a whole), (ii) a tissue sample from the center of the tumor, (iii) a tissue sample from the tissue directly surrounding the tumor which tissue may be more specifically named the "invasive margin" of the tumor and (iv) the lymph nodes located at the closest proximity of the tumor, (vi) a distant metastasis Analysis can also, and preferably, be performed in combined tumor regions (defined above).

Typically, for further analysis, one thin section of the tumor, is firstly incubated with labeled antibodies directed against one biological marker of interest. After washing, the labeled antibodies that are bound to said biological marker of interest are revealed by the appropriate technique, depending of the kind of label is borne by the labeled antibody, e.g. radioactive, fluorescent or enzyme label. Multiple labeling can be performed simultaneously.

Quantifying Biological Markers by Flow Cytometry Methods

In certain embodiments, a biological marker, or a set of biological markers, may be quantified with any one of the flow cytometry methods known in the art.

For example, cells contained in the tumor tissue sample being tested are firstly extracted by mechanical dispersion and cell suspensions in liquid medium are prepared.

Then, the thus obtained cells are incubated during the appropriate time period with antibodies specifically directed against the biological marker(s) that is (are) to be quantified.

After washing the cell suspension in order to remove the unbound antibodies, the resulting cells are analyzed by performing flow cytometry, in view of quantifying the percentage of the total number of cells present in the cell suspension that express each of said biological marker(s).

Illustrative embodiments of quantification biological markers using flow cyometry methods are disclosed in the examples herein.

Quantifying Biological Markers by Nucleic Acid Amplification

In certain embodiments, a biological marker, or a set of biological markers, may be quantified with any one of the nucleic acid amplification methods known in the art.

Analysis can then performed on (i) a global primary tumor (as a whole), (ii) a tissue sample from the center of the tumor (CT), (iii) a tissue sample from the tissue directly surrounding the tumor which tissue may be more specifically named the "invasive margin" of the tumor, (iv) the lymph nodes located at the closest proximity of the tumor, and (vi) a distant metastasis Analysis can also, and preferably, be performed in combined tumor regions (defined above) after tumor microdissection.

The polymerase chain reaction (PCR) is a highly sensitive- and powerful method for such biological markers quantification For performing any one of the nucleic acid amplification method that is appropriate for quantifying a biological marker when performing the cancer prognosis method of the invention, a pair of primers that specifically hybridize with the target mRNA or with the target cDNA is required.

A pair of primers that specifically hybridise with the target nucleic acid biological marker of interest may be designed by any one of the numerous methods known in the art.

In certain embodiments, for each of the biological markers of the invention, at least one pair of specific primers, as well as the corresponding detection nucleic acid probe, is already referenced and entirely described in the public "Quantitative PCR primer database", notably at the following Internet address: http://lpgws.nci.nih.gov/cgi-bin/PrimerViewer.

In other embodiments, a specific pair of primers may be designed using the method disclosed in the U.S. Pat. No. 6,892,141 to Nakae et al., the entire disclosure of which is herein incorporated by reference.

Many specific adaptations of the PCR technique are known in the art for both qualitative and quantitative detections. In particular, methods are known to utilize fluorescent dyes for detecting and quantifying amplified PCR products. In situ amplification and detection, also known as homogenous PCR, have also been previously described. See e.g. Higuchi et al., (Kinetics PCR Analysis: Real-time Monitoring of DNA Amplification Reactions, Bio/Technology, Vol 11, pp 1026-1030 (1993)), Ishiguro et al., (Homogeneous quantitative Assay of Hepatitis C Virus RNA by Polymerase Chain Reaction in the Presence of a Fluorescent Intercalater, Anal. Biochemistry 229, pp 20-213 (1995)), and Wittwer et al., (Continuous Fluorescence Monitoring of Rapid cycle DNA Amplification, Biotechniques, vol. 22, pp 130-138 (1997.))

A number of other methods have also been developed to quantify nucleic acids (Southern, E. M., J. Mol. Biol., 98:503-517, 1975; Sharp, P. A., et al., Methods Enzymol. 65:750-768,1980; Thomas, P. S., Proc. Nat. Acad. Sci., 77:5201-5205, 1980). More recently, PCR and RT-PCR methods have been developed which are capable of measuring the amount of a nucleic acid in a sample. One approach, for example, measures PCR product quantity in the log phase of the reaction before the formation of reaction products plateaus (Kellogg, D. E., et al., Anal. Biochem. 189:202-208 (1990); and Pang, S., et al., Nature 343:85-89 (1990)). A gene sequence contained in all samples at relatively constant quantity is typically utilized for sample amplification efficiency normalization. This approach, however, suffers from several drawbacks. The method requires that each sample have equal input amounts of the nucleic acid and that the amplification efficiency between samples be identical until the time of analysis. Furthermore, it is difficult using the conventional methods of PCR quantitation such as gel electrophoresis or plate capture hybridization to determine that all samples are in fact analyzed during the log phase of the reaction as required by the method.

Another method called quantitative competitive (QC)-PCR, as the name implies, relies on the inclusion of an internal control competitor in each reaction (Becker-Andre, M., Meth. Mol. Cell Biol. 2:189-201 (1991); Piatak, M. J., et al., BioTechniques 14:70-81 (1993); and Piatak, M. J., et al., Science 259:1749-1754 (1993)). The efficiency of each reaction is normalized to the internal competitor. A known amount of internal competitor is typically added to each sample. The unknown target PCR product is compared with the known competitor PCR product to obtain relative quantitation. A difficulty with this general approach lies in developing an internal control that amplifies with the same efficiency of the target molecule.

For instance, the nucleic acid amplification method that is used may consist of Real-Time quantitative PCR analysis.

Real-time or quantitative PCR (QPCR) allows quantification of starting amounts of DNA, cDNA, or RNA templates. QPCR is based on the detection of a fluorescent reporter molecule that increases as PCR product accumulates with each cycle of amplification. Fluorescent reporter molecules include dyes that bind double-stranded DNA (i.e. SYBR Green I) or sequence-specific probes (i.e. Molecular Beacons or TaqMan® Probes).

Preferred nucleic acid amplification methods are quantitative PCR amplification methods, including multiplex quantitative PCR method such as the technique disclosed in the published US patent Application no. US 2005/0089862, to Therianos et al., the entire disclosure of which is herein incorporated by reference.

Illustratively, for quantifying biological markers of the invention, tumor tissue samples are snap-frozen shortly after biopsy collection. Then, total RNA from a "tumor tissue sample" (i) a global primary tumor (as a whole), (ii) a tissue sample from the center of the tumor, (iii) a tissue sample from the tissue directly surrounding the tumor which tissue may be more specifically named the "invasive margin" of the tumor, (iv) the lymph nodes located at the closest proximity of the tumor, (v) a tumor biopsie perform prior surgery (for follow-up of patients after treatment for example), and (vi) a distant metastasis, is isolated and quantified. Then, each sample of the extracted and quantified RNA is reverse-transcribed and the resulting cDNA is amplified by PCR, using a pair of specific primers for each biological marker that is quantified. Control pair of primers are simultaneously used as controls, such as pair of primers that specifically hybridise with 18S cDNA and GADPH cDNA, or any other well known "housekeeping" gene.

Illustrative embodiments of quantification biological markers using nucleic acid amplification methods are disclosed in the examples herein.

Cancer Prognosis Kits

The invention includes a kit for assessing the prognosis of a cancer in a patient (e.g. in a sample such as a tumor tissue patient sample). The kit comprises a plurality of reagents, each of which is capable of binding specifically with a biological marker nucleic acid or protein. Suitable reagents for binding with a marker protein include antibodies, antibody derivatives, antibody fragments, and the like. Suitable reagents for binding with a marker nucleic acid (e.g. a genomic DNA, an mRNA, a spliced mRNA, a cDNA, or the like) include complementary nucleic acids. For example, the nucleic acid reagents may include oligonucleotides (labeled or non-labeled) fixed to a substrate, labeled oligonucleotides not bound with a substrate, pairs of PCR primers, molecular beacon probes, and the like.

Thus, a further object of this invention consists of a kit for the prognosis of progression of a cancer in a patient, which kit comprises means for quantifying at least one biological marker indicative of the status of the adaptive immune response of said patient against cancer.

The kit of the invention may optionally comprise additional components useful for performing the methods of the invention. By way of example, the kit may comprise fluids (e.g. SSC buffer) suitable for annealing complementary nucleic acids or for binding an antibody with a protein with which it specifically binds, one or more sample compartments, an instructional material which describes performance of the cancer prognosis method of the invention, and the like.

Kits Comprising Antibodies

In certain embodiments, a kit according to the invention comprises one or a combination or a set of antibodies, each kind of antibodies being directed specifically against one biological marker of the invention.

In one embodiment, said kit comprises a combination or a set of antibodies comprising at least two kind of antibodies, each kind of antibodies being selected from the group consisting of antibodies directed against one of the CD3, CD8, GZMB, CD45RO, GLNY, TBX21, IRF1, IFNG, CXCL9, OXCL10, CD4, CXCR3, CXCR6, IL-18, IL-18Rbeta, Fractalkine, IL-23, IL-31, IL-15, IL-7, MIG, Perforin, TCRαβ, TCRγδ, LAT, ZAP70, CD5, CD2 biological markers.

An antibody kit according to the invention may comprise 2 to 20 kinds of antibodies, each kind of antibodies being directed specifically against one biological marker of the invention. For instance, an antibody kit according to the invention may comprise 2, 3, 4, 5, 6, 7, 8, 9, 10, 11, 12, 13, 14, 15, 16, 17, 18, 19 or 20 kinds of antibodies, each kind of antibodies being directed specifically against one biological marker as defined herein.

Various antibodies directed against biological markers according to the invention encompass antibodies directed against biological markers selected from the group consisting of CD3, CD8, GZMB, CD45RO, GLNY, TBX21, IRF1, IFNG, CXCL9, CXCL10, CD4, CXCR3, CXCR6, IL-18, IL-18Rbeta, Fractalkine, IL-23, IL-31, IL-15, IL-7, MIG, Perforin, TCRαβ, TCRγδ, LAT, ZAP70, CD5 and CD2.

Various antibodies directed against biological markers according to the invention encompass antibodies directed against biological markers selected from the group consisting of CCR5, CR7, CD103, CDC119, CD120a, CD120b, CD122, CD127, CD134, CD14, CD152, CD154, CD178, CD183, CD184, CD19, CD1a, CD210, CD25, CD26, CD27, CD28, CD3, CD32, CD4, CD44, CD45, CD45Ra, CD45Ro, CD47, CD49d, CD5, CD54, C056, CD62L, CD69, CD7, CD8, CD80, CD83, CD86, CD95, CD97, CD98, CXCR6, GITR, HLA-DR, ICOS, IFNγRII, IL-18Rα, KIR-NKAT2, PD1, TCRαβ and TGFRII. Specific embodiments of these antibodies are listed in Table 3 herein.

Biological markers detectable by specific antibodies may also be selected form the group of biological markers consisting of CD3, CD8, GZMB, CD45RO, GLNY, TBX21, IRF1, IFNG, CXCL9, CXCL10, CD4, CXCR3, CXCR6, IL-18, IL-18Rbeta, Fractalkine, IL-23, IL-31, IL-15, IL-7, MIG, Perforin, TCRαβ, TCRγδ, LAT, ZAP70, CD5, CD2.

In certain other embodiments, a kit according to the invention comprises one or a combination or a set of pair of ligands or specific soluble molecules binding with one or more of the biological marker(s), of the invention.

Kits Comprising Nucleic Acid Primers

In certain other embodiments, a kit according to the invention comprises one or a combination or a set of pair of primers, each kind of pair of primers hybridising specifically with one biological marker of the invention.

In one embodiment, said kit comprises a combination or a set of pair of primers comprising at least two kind of pair of primers, each kind of pair of primers being selected from the group consisting of pair of primers hybridising with one of the CD8A-TBX21, CD3Z-CD8A, CD3Z-TBX21, B7H3-TGFB1, IFNG-TBX21, CD4-CD8A, CD8A, IFNG, CD4-TBX21, CD3Z-CD4, CD4-TGFB1, CD8A-GLNY, IFNG-IRF1, GLNY-IFNG, IRF1-TBX21, IL8-PTGS2, GLNY-TBX21, CD3Z-GLNY, CD3Z-IFNG, GZMB-IFNG, GLNY-IRF1, IL10-TGFB1, CD8A-IL10, CD4-IL10, CD8A-GZMB, GZMB-TBX21, CD3Z-GZMB, CD4-IRF1, GNLY-GZMB, B7H3-IL10, CD4-GZMB, GZMB-IRF1, IL10-TBX21, B7H3-IFNG, B7H3-CD4, CD8A-TGFB1, CD3Z-IL10 and CD4-GNLY biological markers.

In another embodiment, said kit comprises a combination or a set of pair of primers comprising at least two kind of pair of primers, each kind of pair of primers being selected from the group consisting of pair of primers hybridising with one of the 18s, ACE, ACTB, AGTR1, AGTR2, APC, APOA1, ARF1, AXIN1, BAX, BCL2, BCL2L1, CXCR5, BMP2, BRCA1, BTLA, C3, CASP3, CASP9, CCL1, CCL11, CCL13, CCL16, CCL17, CCL18, CCL19, CCL2, CCL20, CCL21, CCL22, CCL23, CCL24, CCL25, CCL26, CCL27, CCL28, CCL3, CCL5, CCL7, CCL8, CCNB1, CCND1, CCNE1, CCR1, CCR10, CCR2, CCR3, CCR4, CCR5, CCR6, CCR7, CCR8, CCR9, CCRL2, CD154, CD19, CD1a, CD2, CD226, CD244, PDCD1LG1, CD28, CD34, CD36, CD38, CD3E, CD3G, CD3Z, CD4, CD40LG, CD5, CD54, CD6, CD68, CD69, CLIP, CD80, CD83, SLAMF5, CD86, CD8A, CDH11, CDH7, CDK2, CDK4, CDKN1A, CDKN1B, CDKN2A, CDKN2B, CEACAM1, COL4A5, CREBBP, CRLF2, CSF1, CSF2, CSF3, CTLA4, CTNNB1, CTSC, CX3CL1, CX3CR1, CXCL1, CXCL10, CXCL11, CXCL12, CXCL13, CXCL14, CXCL16, CXCL2, CXCL3, CXCL5, CXCL6, CXCL9, CXCR3, CXCR4, CXCR6, CYP1A2, CYP7A1, DCC, DCN, DEFA6, DICER1, DKK1, Dok-1, Dok-2, DOK6, DVL1, E2F4, EBI3, ECE1, ECGF1, EDN1, EGF, EGFR, EIF4E, CD105, ENPEP, ERBB2, EREG, FCGR3A, CGR3B, FN1, FOXP3, FYN, FZD1, GAPD, GLI2, GNLY, GOLPH4, GRB2, GSK3B, GSTP1, GUSB, GZMA, GZMB, GZMH, GZMK, HLA-B, HLA-C, HLA-, MA, HLA-DMB, HLA-DOA, HLA-DOB, HLA-DPA1, HLA-DQA2, HLA-DRA, HLX1, HMOX1, HRAS, HSPB3, HUWE1, ICAM1, ICAM-2, ICOS, ID1, ifna1, ifna17, ifna2, ifna5, ifna6, ifna8, IFNAR1, IFNAR2, IFNG, IFNGR1, IFNGR2, IGF1, IHH, IKBKB, IL10, IL12A, IL12B, IL12RB1, IL12RB2, IL13, IL13RA2, IL15, IL15RA, IL17, IL17R, IL17RB, IL18, IL1A, IL1B, IL1RI, IL2, IL21, IL21R, IL23A, IL23R, IL24, IL27, IL2RA, IL2RB, IL2RG, IL3, IL31RA, IL4, IL4RA, IL5, IL6, IL7, IL7RA, IL8, CXCR1, CXCR2, IL9, IL9R, IRF1, ISGF3G, ITGA4, ITGA7, integrin, alpha E (antigen CD103, human mucosal lymphocyte, antigen 1; alpha polypeptide), Gene hCG33203, ITGB3, JAK2, JAK3, KLRB1, KLRC4, KLRF1, KLRG1, KRAS, LAG3, LAIR2, LEF1, LGALS9, LILRB3, LRP2, LTA, SLAMF3, MADCAM1, MADH3, MADH7, MAF, MAP2K1, MDM2, MICA, MICB, MKI67, MMP12, MMP9, MTA1, MTSS1, MYC, MYD88, MYH6, NCAM1, NFATC1, NKG7, NLK, NOS2A, P2X7, PDCD1, PECAM-, CXCL4, PGK1, PIAS1, PIAS2, PIAS3, PIAS4, PLAT, PML, PP1A, CXCL7, PPP2CA, PRF1, PROM1, PSMB5, PTCH, PTGS2, PTP4A3, PTPN6, PTPRC, RAB23, RAC/RHO, RAC2, RAF, RB1, RBL1, REN, Drosha, SELE, SELL, SELP, SERPINE1, SFRP1, SIRP beta 1, SKI, SLAMF1, SLAMF6, SLAMF7, SLAMF8, SMAD2, SMAD4, SMO, SMOH, SMURF1, SOCS1, SOCS2, SOCS3, SOCS4, SOCS5, SOCS6, SOCS7, SOD1, SOD2, SOD3, SOS1, SOX17, CD43, ST14, STAM, STAT1, STAT2, STAT3, STAT4, STAT5A, STAT5B, STAT6, STK36, TAP1, TAP2, TBX21, TCF7, TERT, TFRC, TGFA, TGFB1, TGFBR1, TGFBR2, TIMP3, TLR1, TLR10, TLR2, TLR3, TLR4, TLR5, TLR6, TLR7, TLR8, TLR9, TNF, TNFRSF10A, TNFRSF11A, TNFRSF18, TNFRSF1A, TNFRSF1B, OX-40, TNFRSF5, TNFRSF6, TNFRSF7, TNFRSF8, TNFRSF9, TNFSF10; TNFSF6, TOB1, TP53, TSLP, VCAM1, VEGF, WIF1, WNT1, WNT4, XCL1, XCR1, ZAP70 and ZIC2 biological markers.

In one embodiment, said kit comprises a combination or a set of pair of primers comprising at least two kind of pair of primers, each kind of pair of primers being selected from the group consisting of pair of primers hybridising with one of the TNFRSF6B, CEACAM1, PDCD1LG1, CD8A, PTGS2, BIRC5, SELL, INDO, IRAK4, TNF, TNFRSF10A, MMP7, LILRB3, CD3Z, TNFRSF8, GAPD, CXCL10, EBAG9, IL8, STAT1, CXCR3, TGFB1, ICOS, CXCL9, CD97, IL18RAP, CXCR6, ART1, IRF1, B7H3, ACE, IL18RI, TBX21, IL18, PDCD1, IFNG, GNLY, GATA3, VEGF, GZMB, LAT, CD4, IRTA2, IL10, TNFSF4, THSD1 and PDCD1LG2 biological markers.

In one embodiment, said kit comprises a combination or a set of pair of primers comprising at least two kinds of pair of primers, each kind of pair of primers being selected from the group consisting of pair of primers hybridising with one of the CD3, CD8, GZMB, CD45RO, GLNY, TBX21, IRF1, IFNG, CXCL9, CXCL10, CD4, CXCR3, CXCR6, IL-18, IL-18Rbeta, Fractalkine, IL-23, IL-31, IL-15, IL-7, MIG, Perforin, TCRαβ, TCRγδ, LAT, ZAP70, CD5, CD2 biological markers.

In still another embodiment, said kit comprises a set or a combination of nucleic acid primers, or pairs of primers, each primer or pair of primer hybridising with each of PDCD1LG1, VEGF, TNFRSF6B, IRF1, IL8RA and SELL biological markers.

A primer kit according to the invention may comprise 2 to 20 kinds of pair or primers, each kind of pair of primers hybridising specifically with one biological marker of the invention. For instance, a primer kit according to the invention may comprise 2, 3, 4, 5, 6, 7, 8, 9, 10, 11, 12, 13, 14, 15, 16, 17, 18, 19 or 20 kinds of pairs of primers, each kind of pair of primers hybridising specifically against one biological marker as defined herein.

Notably, at least one pair of specific primers, as well as the corresponding detection nucleic acid probe, that hybridize specifically with one biological marker of interest, is already referenced and entirely described in the public "Quantitative PCR primer database", notably at the following Internet address: http://lpgws.nci.nih.gov/cgi-bin/PrimerViewer.

Monitoring Anti-Cancer Treatments

Monitoring the influence of agents (e.g., drug compounds) on the level of expression of a biological marker of the invention can be applied for monitoring the status of the adaptive immune response of the patient with time. For example, the effectiveness of an agent to affect biological marker expression can be monitored during treatments of subjects receiving anti-cancer treatments.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of one or more selected biological markers of the invention in the pre-administration sample; (iii) obtaining one or more post-administration samples from the subject; (iv) detecting the level of expression of the biological marker(s) in the post-administration samples; (v) comparing the level of expression of the biological marker(s) in the pre-administration sample with the level of expression of the marker(s) in the post-administration sample or samples; and (vi) altering the administration of the agent to the subject accordingly. For example, decreased expression of the biological marker gene(s) during the course of treatment may indicate ineffective dosage and the desirability of increasing the dosage. Conversely, increased expression of the biological marker gene(s) may indicate efficacious treatment and no need to change dosage.

As already mentioned previously in the present specification, performing the cancer prognosis method of the invention may indicate, with more precision than the prior art methods, those patients at high-risk of tumor recurrence who may benefit from adjuvant therapy, including immunotherapy.

For example, if, at the end of the cancer prognosis method of the invention, a good prognosis of no metastasis or a prognosis of a long time period of disease-free survival is determined, then the subsequent anti-cancer treatment will not comprise any adjuvant chemotherapy.

However, if, at the end of the cancer prognosis method of the invention, a bad prognosis with metastasis or a bad prognosis with a short time period of disease-free survival is determined, then the patient is administered with the appropriate composition of adjuvant chemotherapy.

Further, if, at the end of the cancer prognosis method of the invention, a bad prognosis with metastasis or a bad prognosis with a short time period of disease-free survival is determined, then the patient is administered with the appropriate immunostimulating composition, including pharmaceutical composition comprising an immunostimulating cytokine or chemokine, including interleukines.

Preferred immunostimulating cytokines or chemokines are selected from the group consisting of IL-1α, IL-1β, IL-2, IL-3, IL4, IL-5, IL-7, G-CSF, IL-15, GM-CSF, IFN-γ, CXCL9, CXCL10, Fractalkine, MIG, IFNα, IL-18, IL-12, IL-23 and IL-31.

Accordingly, the present invention also relates to a method for adapting a cancer treatment in a cancer patient, wherein said method comprises the steps of:

a) performing, on at least one tumor tissue sample collected from said patient, the cancer prognosis method that is disclosed herein;

b) adapting the cancer treatment of said cancer patient by administering to said patient an adjuvant chemotherapy or an immunostimulating therapy if a bad cancer prognosis is determined at the end of step a).

Another object of the invention consists of a kit for monitoring the effectiveness of treatment (adjuvant or neo-adjuvant) of a subject with an agent, which kit comprises means for quantifying at least one biological marker indicative of the status of the adaptive immune response of said patient against cancer.

The present invention is further illustrated by, without in any way being limited to, the examples below.

EXAMPLES

A. Material and Methods of the Examples

Material and Methods of Examples 1 to 4

A.1. Patients and Database

All cases of colorectal cancer (n=959) who underwent a primary resection of the tumor at the Laennec/HEGP Hospital between 1986 and 2004 were reviewed. The observation time in this unselected cohort was the interval between diagnosis and last contact (death or last follow-up). Data were censored at the last follow-up for patients who had not relapsed or who had died. The mean duration of follow-up was 44.5 months. Six patients lost to follow-up were excluded from the analysis. Histopathological and clinical findings were scored according to the UICC-TNM staging system (Sobin L H, Wittekind C, (eds). UICC TNM classification of malignant tumors. 6th ed. New York: Wiley-Liss, 2002), as disclosed in Table 1. Early metastatic invasion was defined as the presence of vascular emboli (VE), lymphatic invasion (LI), or perineural invasion (PI). A VELIPI-positive tumor had at least one of these pathologic findings, whereas a VELIPI-negative tumor had none of the three findings. TNM and VELIPI status of the tumors were determined from the histopathological reports at the time of resection. A secure Web-based database, TME.db (Tumoral MicroEnvironment Database), was built on a 3-tier architecture using Java-2 Enterprise-Edition (J2EE) to integrate clinical data sets, and the results from high-throughput technologies.

The records of 959 Patients with colorectal who underwent a primary resection at the Laennec/HEGP Hospital between 1986 and 2004 were retrospectively reviewed representing a prospective, continuous, unselected cohort of patients. Conventional histopathological parameters, including AJCC/UICC TNM stage, Duke's stage, tumor type, and grade of differentiation, lymphovascular embolies, perineural tumor invasion (VELIPI), are detailed in Table 1. Data on adjuvant and palliative chemotherapy were recorded. Adjuvant with S-fluorouracil (FU)-based chemotherapy was administered to 327 patients (57 patients with stage II disease, 136 with stage III disease, and 134 with stage IV disease).

Postsurgery patient surveillance was carried-out, at Laennec/HEGP and associated hospitals, for all patients according to general practice for colon cancer patients, including physical examination, blood counts, liver function tests, serum carcinoembryonic antigen, abdominal ultrasonography and computed tomography scan, and pulmonary x-ray. Colonoscopy was performed one year after resection and then once every three years if normal. If tumor relapse was suspected, the patient underwent intensive work-up, including abdominal computed tomography scan, magnetic resonance imaging, chest x-ray, colonoscopy, and biopsy, when applicable.

Clinical findings, treatment, histopathologic report, and follow-up data were collected prospectively and updated (by A.B) and included into TME.db. The database is accessible upon request to zlatko.traianoski@tugraz.at. Observation time was the interval between diagnosis and last contact (death or last follow-up). Data were censored at the last follow-up for patients without relapse, or death. The mean duration of follow-up was 44.5 months. The min:max values until progression/death or last follow-up were (0:214) months, respectively. Six patients lost to follow-up were excluded from the analysis. Time to recurrence or disease-free time was defined as the time period from the date of surgery to confirmed tumor relapse date for relapsed patients and from the date of surgery to the date of last follow-up for disease-free patients.

A.2. Histopathology

All the H&E sections of the tumors for each patient were reassessed blindly by two pathologist (D.D., T.M.) or two investigators (F.P., J.G.) trained in the pathology of colonic cancer, for each of the following: (a) tumoral lymphoid infiltrate (b) lymphoid reaction at the invasive margin (10 to 20 fields analyzed per-patient). The densities of these immune infiltrates were scored independently by the investigators, as weak (score 1), moderate (score 2), or strong (score 3), as disclosed hereunder.

Three hundred seventy seven randomly selected tumors from the 415 tumors evaluated by TMA were reassessed for immune cell density. Review of tissue sections was performed independently by two pathologists (D.D., T.M.) or two investigators (F.P. and J.G.) trained in the pathology of colonic cancer. A mean number of four sections of primary tumor were analyzed. The fields analyzed were chosen as representative of the region, and were at distance from necrotic material or abscesses. Immune infiltrates were scored as followed:

(a) Tumoral Lymphoid Infiltrates:

The density of tumoral lymphoid infiltrates was quantified by counting the small round lymphocytes distributed within the tumor epithelium and the peritumoral stroma in five medium power fields (Nikon microscope, ×20 objective). Immune-infiltrate density scored as 1 (weak), 2 (moderate) or 3 (strong), was observed in 16%, 62% and 22% of the series, respectively.

(b) Lymphoid Reaction at the Invasive Margin:

The cuff of lymphocytes abutting the deepest point of advancing tumor (invasive margin) was judged as, conspicuous (score 3), inconspicuous (score 2) or absent (score 1). The lymphoid reaction scored as 1, 2 or 3, was observed in 18%, 60% and 22% of the series, respectively.

(c) Lymphoid Nodules Surrounding the Periphery of the Tumor:

Crohn's-like lymphoid reaction was defined as lymphoid aggregates (often with germinal centers) ringing the periphery of invasive carcinoma typically found at the interface of the muscularis propria externa and pericolic fibro-adipose tissue, not associated with either mucosa (e.g., diverticular origin) or pre-existing lymph node. Two large lymphoid aggregates in a section were required for the presence of this feature (score 2). More than two large lymphoid aggregates referred to score 3, whereas only one or an absence of lymphoid aggregates was scored 1. The density of lymphoid nodules scored as 1, 2 or 3, was observed in 38%, 39% and 23% of the series, respectively.

Real-Time Taqman PCR Analysis

Total RNA was extracted from 100 randomly selected frozen tumor specimens from the cohort of 959 cases; 75 samples of sufficient quality and quantity were analyzed for gene expression using quantitative real-time TaqMan-PCR (Low-Density-Arrays) and the 7900 robotic PCR-system (Applied-Biosystems, Foster City, Calif.), as disclosed hereunder.

Tissue samples were snap-frozen within 15 minutes following surgery and stored in liquid $N_2$. Randomly selected frozen tumor specimens (n=100) from the cohort were extracted for RNA. Total RNA was isolated by homogenization with RNeasy isolation-kit (Qiagen, Valencia, Calif.). The integrity and the quantity of the RNA were evaluated on a bioanalyzer-2100 (Agilent Technologies, Palo Alto, Calif.). Seventy-five samples were of sufficient RNA quality and quantity for Low-Density-Array analysis. These samples, representative of the cohort, were all assessed for gene expression analysis. RT-PCR experiments were carried-out according to the manufacturer's instructions (Applied-Biosystems, Foster City, Calif.). Quantitative real-time TaqMan-PCR was performed using Low-Density-Arrays and the 7900 robotic real-time PCR-system (Applied-Biosystems) (see list of genes in Table 2 for details). 18S and GAPDH primers and probes were used as internal controls. Data were analyzed using the SDS Software v2.2 (Applied-Biosystems).

Tissue samples were snap-frozen within 15 minutes following surgery and stored in liquid $N_2$. Randomly selected frozen tumor specimens (n=100) from the cohort (n=959), were extracted for RFNA. Total RNA was isolated by homogenization with RNeasy isolation-kit (Qiagen, Valencia, Calif.) The integrity and the quantity of the RNA were evaluated on a bloanalyzer-2100 (Agilent Technologies, Palo Alto, Calif.). Seventy-five samples were of sufficient RNA quality and quantity for Low-Density-Array analysis. These samples, representative of the cohort, were all assessed for gene expression analysis. RT-PCR experiments were carried-out according to the manufacturer's instructions (Applied-Biosystems, Foster City, Calif.). Quantitative real-time TaqMan-PCR was performed using Low-Density-Arrays and the 7900 robotic real-time PCR-system (Applied-Biosystems) (see list of genes in Table 2 for details). 18S and GAPDH primers and probes were used as internal controls. Data were analyzed using the SDS Software v2.2 (Applied-Biosystems).

Large-Scale Flow-Cytometric Analysis

Cells were extracted by mechanical dispersion from 39 fresh tumor samples. All cells (including tumor cells) were analyzed by flow-cytometry. Cells from normal mucosa from a site that was distant from the fresh tumor were also analyzed. Cells were incubated for 30 minutes at 4° C. with antibodies against immune cell markers (See Table 3 for the list of antibodies). Analyses were performed with a four-color-FACScalibur flow cytometer and CellQuest software (Becton Dickinson, San Diego, Calif.). Immune subpopulations were measured as a percentage of the total number of all cells and a percentage of the number of total CD3+ cells. Average-linkage hierarchical clustering was applied and the results were displayed using the GENESIS program (Sturn A, Quackenbush J, Trajanoski Z. Genesis: cluster analysis of microarray data. Bioinformatics 2002; 18(1):207-8; Galon J, Franchimont D, Hiroi N, et al. Gene profiling reveals unknown enhancing and suppressive actions of glucocorticoids on immune cells. Faseb J 2002; 16(1):61-71; software available at http://www.genome.tugraz.at).

Tissue Microarray Construction

Using a tissue-array instrument (Beecher Instruments, ALPHELYS, Plaisir, France), two representative areas of the tumor (center and invasive margin) were removed (0.6 mm and 1 mm-diameter punches, respectively) from paraffin-embedded tissue-blocks that were prepared at the time of resection. Of the colonic carcinomas that were resected between 1990 and 2003, 50 percent (415) were randomly selected for construction of tissue microarrays. Based on T, N, M, VELIPI pathologic findings, patients with these tumors were representative of the entire cohort. Tissue-cores arrayed into recipient paraffin-blocks were cut into 5 μm sections for Harris's hematoxylin (HE) and immunohistochemical staining.

Immunohistochemistry

Following antigen retrieval and quenching of endogen-peroxidase activity, sections were incubated (60 min. at room temperature) with monoclonal antibodies against CD45RO and CD3 (Neomarkers, Fremont, Calif.). Envision+ system (enzyme-conjugated polymer backbone coupled to secondary antibodies) and DAB-chromogen were applied (Dako, Copenhagen, Denmark). Tissue sections were counterstained with Harris' hematoxylin. Isotype-matched mouse monoclonal antibodies were used as negative controls, Slides were analyzed using an image analysis workstation (Spot Browser®, ALPHELYS). Polychromatic high-resolution spot-images (740×540 pixel, 1.181 μm/pixel resolution) were obtained (×100 fold magnification). Measurements were recorded as the number of positive cells per-tissue surface-unit.

Statistical Analysis

Kaplan-Meier curves were used to assess the influence of pathologic signs of early metastatic invasion (VELIPI) on overall and disease-free survival. The significance of various clinical parameters was assessed by univariate analysis using the log-rank test (Table 1). We used a Cox proportional-hazards model to test the simultaneous influence on survival (overall and disease-free) of all covariates found significant in the univariate analysis. The same tests were used to assess the effect of the density of CD45RO (number of cells/mm$^2$) on overall and disease-free survival, alone or together with the tumor, node, and metastases (T, N, M) staging covariates. The Anova-t test and the Wilcoxon-Mann-Whitney test were the parametric and non-parametric tests used to identify markers with a significantly different expression among VELIPI-positive and VELIPI-negative tumors. Normality of the logarithm of the gene expression levels and of the CD45RO densities was determined using the Shapiro test. The Wilcoxon test was used to assess the significance of the difference between median survivals across different groups of patients. All tests were two-sided. A P-value <0.05 was considered statistically significant. All P-values are reported without multiple correction adjustments. All analyses were performed with the statistical software R and Statview.

Material and Methods of Example 5

A.3. Patients and Database

The records of 415 colorectal cancer (CRC) patients who underwent a primary resection of their tumor at the Laennec-HEGP Hospitals between 1990 and 2003 were reviewed. These 415 patients from Laennec-HEGP Hospitals were the main subject of our study (Table 11-S1).

Paraffin-embedded tumor samples were available from 150 consecutive patients diagnosed with CRCs in Avicenne Hospital between 1996 and 2001. Finally, 119 patients of this validation series, not lost to follow-up and with biopsy samples from the 2 tumor regions (Tissue-Microarray spots) available, were evaluated for the survival analyses. These 119 patients (12, 33, 48, and 26 patients with UICC-TNM stages 1, II, III, and IV, respectively) from Avicenne Hospital were the first validation set.

Frozen tumor samples from 75 patients from Laennec-HEGP Hospitals were selected for gene expression analysis. These patients are different from the main series of 415 patients. From this series of 75 patients (6, 17, 24, and 28 patients with UICC-TNM stages I, II, III, and IV, respectively), paraffin-embedded tumor samples from 69 patients, with biopsy samples from the 2 tumor regions (Tissue-Microarray spots) available, were evaluated for the survival analyses. These 69 patients from Laennec-HEGP Hospitals were the second validation set.

The observation time in these cohorts was the interval between diagnosis and last contact (death or last follow-up). Data were censored at the last follow-up for patients without relapse, or death. The mean duration of follow-up of the main series was 45.3 months. The min:max values until progression/death or last follow-up were (0:166) months, respectively. Time to recurrence or disease-free time was defined as the interval from the date of surgery to confirmed tumor relapse date for relapsed patients and from the date of surgery to the date of last follow-up for disease-free patients. Histopathological and clinical findings were scored according to the UICC-TNM staging system (L. Sobin, C. Wittekind, *TNM classification of malignant tumors*. 6th, Ed. (Wiley-Liss, New York, 2002). Postsurgery patient surveillance was performed at Laennec-HEGP, Avicenne and associated Hospitals for all patients according to general practice for CRC patients. Adjuvant chemotherapy was administered to patients with stage III CRCs, to high-risk stage II CRCs, and palliative chemotherapy to patients with advanced colorectal cancers (stage IV) and to patients without complete resection of the tumor.

Adjuvant chemotherapy was fluorouracil (FU)-based. Follow-up data were collected prospectively and updated. A secure Web-based database, TME.db (Tumor MicroEnvironment Database, access available upon request), was built on a 3-tier architecture using Java-2 Enterprise-Edition (J2EE) to integrate the clinical data and the data from high-throughput technologies.

A.4. Histopathology

Real-Time Taqman PCR Analysis

Real time Taqman PCR analysis was performed such as described in the Material and Methods of Examples 1 to 4 above.

Tissue Microarray Construction

Tissue Microarray Construction was performed such as described in the Material and Methods of Examples 1 to 4 above.

Immunochemistry

Tissue microarray sections were incubated (60 min. at room temperature) with monoclonal antibodies against CD3 (SP7), CD8 (4B11), CD45RO (OPD4), GZMB (GrB-7), cytokeratin (AE1AE3) and cytokeratin-8 (Neomarkers, Fremont, Calif.). Envision+ system (enzyme-conjugated polymer backbone coupled to secondary antibodies) and DAB-chromogen were applied (Dako, Copenhagen, Denmark). Double stainings were revealed with phosphate-conjugated secondary antibodies and FastBlue-chromogen. For single stainings, tissue sections were counterstained with Harris' hematoxylin. Isotype-matched mouse monoclonal antibodies were used as negative controls. Slides were analyzed using an image analysis workstation (Spot Browsers), ALPHELYS). Polychromatic high-resolution spot-images (740×540 pixel, 1.181 □m/pixel resolution) were obtained (×100 fold magnification). The density was recorded as the number of positive cells per unit tissue surface area. For each duplicate, the mean density was used for statistical analysis.

For each tumor, the duplicate of spots showed a good level of homogeneity of stained cell densities in each tumor region (CT and IM). Heterogeneous densities of the immune infiltrates (HiLo and LoHi) between tumor regions (CT/IM) were present in 37%, 33%, 47%, 36% of the tumors assessed for CD3, CD8, CD45RO and GZMB cell densities, respectively.

Statistical Analysis

Genesis clustering software (J. Galon et al., 2002, *Faseb J*, Vol. 16: 61) was used to visualize the correlation matrix presented in FIG. 1 and to perform Pearson un-centered hierarchical clustering. The pvcluster R package was used to validate the found clusters.

Kaplan Meier estimators of survival were used to visualize the survival curves and to obtain the estimators of the median, 75$^{th}$ percentile and survival rates at 2, 4 and 5 years for OS and DFS. The log-rank test was used to compare disease-free and overall survival between patients in different groups. For the markers measured with RT-PCR, the median expression level was taken as cut-off to dichotomize the variables. For the four markers further studied in two different regions (CT and IM) using TMA (CD3, CD45RO, CD8, GZM) the "minimum p-value" approach was applied to obtain the cutoff providing the best separation between the groups of patients related to their disease-free survival outcome. The cut-off values for CD3, CD8, CD45RO, GZMB cell densities were 370, 80, 80, 30 cells/mm$^2$ in the center of the tumor and 640, 300, 190 and 60 cells/mm$^2$ in the invasive margin, respectively. Because the P-values to obtained in this way might present severe over-fitting, DFS log-rank P-values were corrected using the formula proposed by Altman et al (D. G. Altman et al., 1994, *J. Natl Cancer Inst*, Vol. 86: 829). Additionally, DFS and OS log-rank P-values were calculated using 2-fold cross-validation after (D. Faraggi et al., 1996, *Stat Med*, Vol, 1&: 2203). 100 repetitions were performed (with and without stratifying on the grouping variable). The median p-values are summarized in Tables 13-14 (S4-S5) and 16-17 (S7-S8).

A multivariate Cox proportional hazards model was applied to the $CD3_{CT}CD3_{IM}$ combined regions marker to determine its hazard ratio after adjustment by traditional histopathological tumor markers. The Cox model was applied only to patients with UICC-TNM, I, II, III to guarantee a common baseline hazard function. Hazard ratios from the DFS model were corrected using a shrinkage factor estimated from leave-one-out cross-validation as suggested by Hollander et al (N. Hollander et al., 2004, *Stat Med*, Vol. 23: 1701). Models using the median as cutoff are presented in the Tables 14-15 and 18-19. Additionally, the markers of interest were an independent prognostic factor when considering the markers of interest in its original continuous scale (data not shown).

All through the text a P-value <0.05 was considered statistically significant. All analyses were performed with the statistical software R (survival package) and Statview.

B. Results

Example 1

Correlation between Clinical Outcome and Adaptive Immune Response 1.1 Early Metastatic Invasion and Clinical Outcome The prognostic significance of the presence of vascular emboli (VE), lymphatic invasion (LI), and perineural invasion (PI), which delineated early metastatic invasion (VE-LIPI), was investigated by univariate analysis of the 959 colorectal cancer patients. VE, LI, PI, and VELIPI as well as the T, N, M stage significantly influenced disease-free and overall survival (P<0.001) (Table 1).

The five-year disease-free survival rates were 32.4 percent among patients with VELIPI-negative tumors, and 12.1 percent among patients with VELIPI-positive tumors, respectively. Differences were also observed in the median duration of disease-free survival (3.3 vs 26.9 months for VELIPI-positive and VELIPI-negative tumors, respectively, P<0, 001). A similar pattern was found for overall survival (Table 1).

Furthermore, the presence of more than one sign of early metastatic invasion conferred a worse prognosis that a single sign. Kaplan-Meier curves suggested longer overall survival and disease-free survival in patients with VELIPI-negative tumors than in patients with VELIPI-positive tumors (log-rank test, P<0.001). VE, LI, or PI correlated with the N and M stages (P<0.001 for all comparisons). The influence of all significant covariates on survival was simultaneously tested using a Cox proportional-hazards model. Multivariate analysis adjusting for TNM staging confirmed that VELIPI status was significantly and independently associated with a better prognosis (P=0.04 and P=0.01 for overall and disease free survival, respectively). Adjusting for Dukes staging, VELIPI status was independently associated with a better prognosis (P=0.007 and P=0.002 for overall and disease free survival, respectively).

1.2 Immune Cell Infiltration, Inflammation, Early-Metastatic Invasion, and Prognosis Colorectal tumors (n=377) were assessed histopathologically for an immune cell infiltrate within the tumor and in the invasive margin.

The presence of strong immune infiltrate (score 3) was associated with VELIPI-negative tumors.

Figure 1:
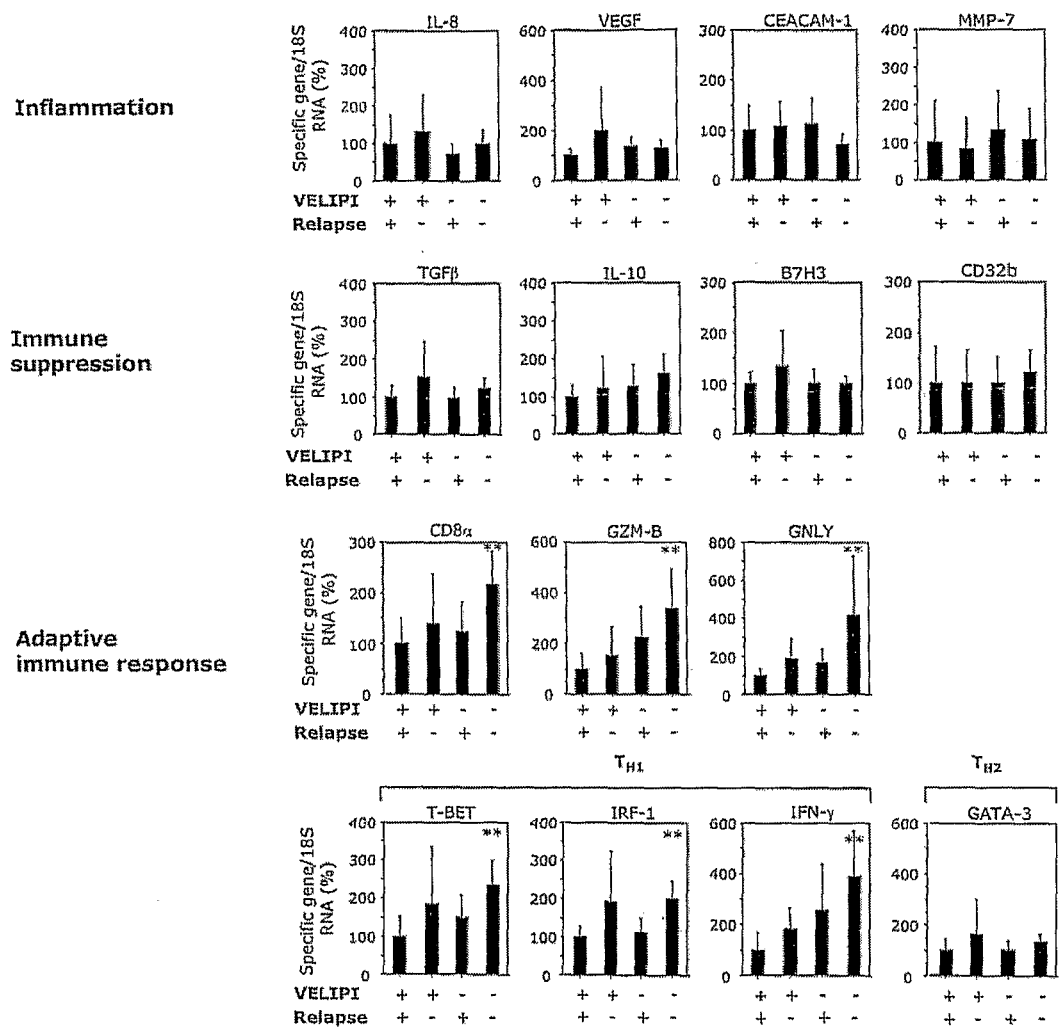
FIG. 1 illustrates results of expression of inflammatory-, immune suppressive- and immune adaptive-related genes in a series of 75 colorectal cancers according to the VELIPI status and relapse. Relative mRNA expression levels were normalized to the level of 18S mRNA for each sample. The levels are represented as fold increase (%) compared to the reference group of invasion positive (VELIPI+) patients that experienced a relapse. **: $P<0.05$ compared to the reference group.

The mRNAs for proinflammatory and immunosuppressive molecules in 75 colorectal tumors were measured by low density array quantitative real-time PCR. No significant association between content of mRNA for proinflammatory mediators (IL-8, VEGF, CEACAM-1, MMP-7, Cox-2 and thrombospondin-1), or for immunosuppressive molecules (TGFβ, IL-10, B7-H3, and CD32b) and VELIPI status or relapse was found (FIG. 1 and data not shown).

T-cells differentiate into $T_H1$ or $T_H2$ cells following expression of T-bet or GATA-3, respectively. Protective immune responses are mediated by effector-memory T-cells with the phenotype CD8+, CD45RO+, CCR7-, CD62L-, perforin+, granulysin+, granzyme-B+. These cells exert an immediate effector function upon antigen stimulation by releasing cytotoxic mediators. As shown in FIG. 1, CD8α, granulysin, and granzyme-B were increased in VELIPI-negative tumors and were further increased in such tumors from patients who had not relapsed, as compared with VELIPI-positive tumors from patients who had relapsed (P<0.05).

Moreover, VELIPI-negative tumors from patients who had not relapsed had a significant increase in the $T_H1$ mediators T-bet, IRF-1, and IFN-γ compared to VELIPI-positive tumors from patients who had relapsed (P<0.05). In contrast, the $T_H2$ transcription factor, GATA-3, was not increased in either group of patients (FIG. 1).

Example 2

Phenotypes of Tumor-Infiltrating Immune Cells

Subpopulations of immune cells from 39 freshly resected colon cancers were analyzed by large-scale flow-cytometry. To refine the analysis, 410 different combinations of surface markers were measured by FACS, and the results were plotted from the minimum to the maximum expression.

T-cells, B-cells, NK-cells, NKT-cells, and macrophages were analyzed in relation to the VELIPI status of the tumors, CD3+ T-cells were the most prevalent tumor-infiltrating immune cells. CD3+, CD3+CD4+, and CD3+CD8+ T-cells were significantly increased (2.6, 2.5, 4.9 fold increase, respectively, P<0.05) in VELIPI-negative tumors compared to VELIPI-positive tumors.

Large-scale analysis of phenotypic and functional markers of T-cell subpopulations (percentage of positive cells in the total population isolated from the tumor and within the CD3+ T-cell population) revealed a significant difference (P<0.05) between VELIPI-negative and VELIPI-positive tumors for 65 different combinations of markers. Hierarchical clustering (Eisen M B, Spellman P T, Brown P O, Botstein D. Cluster analysis and display of genome-wide expression patterns. Proc Natl Acad Sci USA 1998; 95(25):14863-8) showed a homogeneous pattern in VELIPI-positive tumors, whereas two subgroups of VELIPI-negative tumors could be distinguished.

All markers (CD45RO, CD45RA, CD27, CD28, CCR7, CD127) of the T-cell differentiation process from naïve to effector-memory T-cells were present in the cluster of differentially expressed markers. Markers of T cell migration (CD62L-, CCR7-, CD103, CD49d, CXCR3) and activation (HLA-DR, CD98, CD80, CD86, CD134) were also differentially expressed between VELIPI-negative and VELIPI-positive tumors.

The results have shown that naïve T cells (CD3+CCR7+) were rare in the tumors. By contrast, in the differentiation pathway from early-memory T cells (CD45RO+CCR7-CD28+CD27+) to effector-memory T-cells (CD45RO+CCR7-CD28-CD27-), all subpopulations were detected. Compared with VELIPI-positive tumors, VELPI-negative tumors had significantly more of these T cells (P<0.05). The results show that the high proportion of mature CD8+ T-cells in VELIPI-negative tumors. In contrast to tumors, distant normal mucosa from the same patients did not exhibit differences in the CD8+ T-cell subpopulations according to the VELIPI status.

Example 3

Effector-Memory T Cells and Survival

Immunohistochemical analysis on Tissue-MicroArrays prepared from 415 colorectal cancers was performed. Staining with an anti-CD3 antibody revealed the presence of T-cells both within and at the invasive margin of the tumor. CD45RO+ cells were counted by automatic image software. A validation study showed a close correlation between optical and automatic cell counts ($R^2$=0.914, P<0.001), VELIPI-negative tumors contained high numbers of CD45RO cells as compared to VELIPI-positive tumors (P-0.02). In addition, high density of memory T-cells was associated with lymph-node negative (N-) and metastasis negative (M-) tumors (P<0.001).

Figure 2:
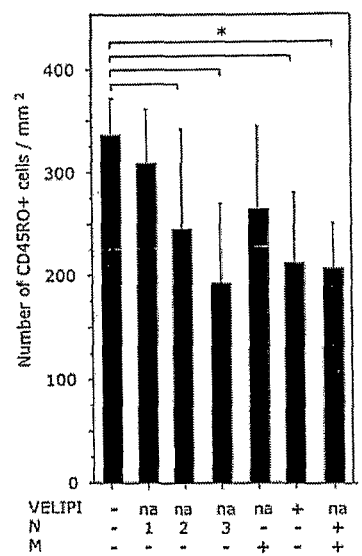
FIG. 2 shows the mean±SEM of CD45RO+ cells/mm$^2$ in the different groups of patients (N and M stages, according to the AJCC/UICC TNM staging, na: not applicable). Statistical analyses were performed using Mann-Whitney test. * Represent significant differences ($P<0.05$).

Advanced stages of lymph-node invasion (N2, N3) were associated with low densities of CD45RO in tumors (FIG. 2).

Figure 3:
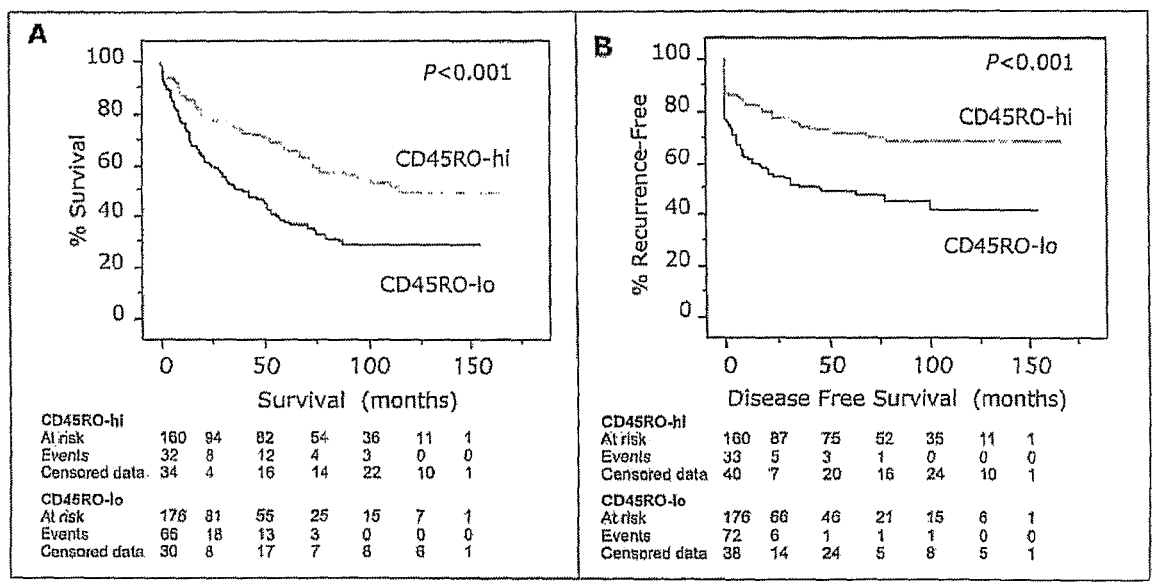
FIG. 3 shows Kaplan-Meier overall survival (OS) and disease free survival (DFS) curves in CD45RO-hi (>250 CD45RO+ cells/mm$^2$, n=176, upper line), and in CD45RO-lo (<250 CD45RO+ cells/mm$^2$, n=160, bottom line).

Multivariate Cox proportional-hazard analysis showed that M (P<0.001), N (P=0.002), and T (P=0.004) as well as CD45RO (P=0.02) were independent prognostic factors for overall survival, Kaplan-Meier curves suggested longer overall survival and disease-free survival (FIGS. 3A, 3B) in patients with tumors containing high density of CD45RO than in patients with low density (log-rank test, P<0.001). Patients whose tumors contained high density of CD45RO had a median disease-free survival of 36.5 months and a median overall survival of 53.2 months, as compared with 11.1 and 20.6 months, respectively, among patients with low density of CD45RO (P<0.001 for all comparisons) (FIGS. 3A, 3B). The five-year overall (FIG. 3A) and disease-free survival (FIG. 3B) rates were 46.3 and 43.1 percent among patients with tumors containing high density of CD45RO and 23.7 and 21.5 percent among patients with tumors containing low density of CD45RO.

Results of Examples 1 to 3 above show that there exists a relation between pathologic signs of early metastatic invasion (vascular emboli (VE), lymphatic invasion (LI), and perineural invasion (PI), collectively termed VELIPI) and the outcome in 959 colorectal cancers.

It has also been shown the existence of an association between the VELIPI status of the tumor and evidence of an immune response within the tumor. In particular, an analysis of 39 colorectal cancers showed that the presence of intratumoral effector-memory T-cells, defined by CD3, CD8, CD45RO, CCR7, CD28, and CD27 markers, was associated with VELIPI-negative tumors. Analysis of 415 colorectal tumors showed that high density of infiltrating CD45RO+ cells correlated with a good clinical outcome.

In the series of 959 colorectal cancers herein, emboli detected by meticulous pathological examination showed a significant, independent association between VELIPI status and overall survival.

In examples 1 to 3 above, no significant differences were found in the content of mRNAs for proinflammatory and immunosuppressive molecules in VELIPI-positive and VELIPI-negative tumors, or in tumors from patients who did or did not relapse. These findings suggest that inflammation is not a factor in early metastatic invasion.

In contrast, there was increased mRNA for products and markers of $T_H1$ effector T-cells (CD8, T-bet, IRF-1, IFN-γ, granulysin, and granzyme-B), and this increase was associated with prolonged survival and a lack of pathological, signs of early metastatic invasion.

Using tissue microarrays, the association between a high number of CD45RO+ T-cells and the absence of lymphovascular and perineural invasion (P<0.002) was shown in Examples 1 to 3 above. Tumors that contained high density of effector-memory T cells were associated with longer disease-free and overall survival than tumors lacking such cells (P<0.001). The presence of CD45RO-positive memory T-cells in the tumor was an independent prognostic factor.

In examples 1 to 3, the high-throughput quantitative measurement of cellular and molecular differences among colorectal cancers allowed a detailed characterization of the tumor micro-environment, and identification of associations with clinical outcome. The experimental results show that the tumor microenvironment and the host's immune response are of major importance in tumor progression.

Thus, it has been shown in Examples 1 to 3 above that univariate analysis showed significant differences in disease-free and overall survival according to the presence or absence of histological signs of early metastatic invasion (P<0.001). By multivariate Cox analysis, pathologic stage (T, N, M) (P<0.001) and early metastatic invasion (P=0.04) were independently associated with survival. Tumors lacking signs of early metastatic invasion had infiltrates of immune cells and increased mRNA for products of $T_H1$ effector T-cells (CD8, T-bet, IRF-1, IFN-γ, granulysin, and granzyme-B).

In contrast, neither proinflammatory mediators nor immunosuppressive molecules were differentially expressed. In tumors with or without early signs of metastatic invasion there were significant differences for 65 combinations of T-cell markers, and hierarchical clustering showed that markers of T cell migration, activation, and differentiation were increased in tumors lacking these signs.

These tumors contained increased numbers of CD8-positive T cells, ranging from early-memory (CD45RO+CCR7-CD28+CD27+) to effector-memory (CD45RO+CCR7-CD28-CD27-) T-cells. The presence of infiltrating memory CD45RO+ cells, evaluated by immunohistochemistry, correlated with signs of early metastatic invasion, pathological stage, and survival.

It has thus been shown that signs of an immune response within colorectal cancers are associated with the absence of pathological evidence of early metastatic invasion and prolonged survival, Example 4

Correlation between (i) Adaptive Immune Response and (i) Recurrence and Survival Times Functional orientation of the host-response within colorectal cancers was investigated by quantitative real-time PCR through the evaluation of 18 immune-related genes. These genes were variably expressed among the 75 tumours studied.

Correlation analyses performed between all genes (representing 153 correlation tests) showed 70 significant combinations (P<0.05) is including 39 highly significant combinations (P<0.0001) (See Table 4).

A correlation-matrix was generated, followed by unsupervised hierarchical clustering offering a convenient way to visualize patterns of similarity and difference among all correlations. This allowed the identification of a dominant cluster of co-modulated genes, composed of $T_{H1}$ (T-bet, IRF-1, IFNγ) and immune-adaptive (CD3ζ, CD8, GLNY, GZMB) related genes, and two clusters referring to proinflammatory and immune-suppressive mediators.

Expression patterns of the clusters were almost mutually exclusive in the tumours. Expression levels of genes from the $T_{H1}$/adaptive cluster inversely correlated with relapse, whereas the others (VEGF, MMP-7, Cox-2, IL-8, Survivin, CEACAM1, TRAIL-R, B7H3, IL-10, TGFb) did not.

A hierarchical tree structure classifying the 75 colorectal cancers according to the mRNA levels of genes from the $T_{H1}$/adaptive cluster (from maximal to minimal expression levels) showed progressive recurrence rates from 20% to 80%, (Fisher exact test comparing group 1 and group 2, P-0.016). Patients with a homogeneous increased pattern of $T_{H1}$/adaptive gene expression in tumour were associated with the best prognosis.

Altogether, these data provided evidence for a beneficial effect of in situ $T_{H1}$/adaptive immunity on clinical outcome.

Then, the cellular end results of the immune-adaptive gene expression profiles was assessed by immunohistochemical-based Tissue-MicroArrays analysis of 415 tumours.

Furthermore, distribution of the in situ adaptive immune response was explored by spotting the centre of the tumour (CT) along with the invasive margin (IM).

In both tumour regions, immunostaining for total T lymphocytes (CD3), CD8 T cell effectors and associated cytotoxic molecule (GZMB), and memory T cells (CD45RO) showed a wide spectrum of positive-immune cell densities among all sample tested, The 6640 corresponding immunostainings were analysed with a dedicated image analysis workstation for signal quantification (captured spot), allowing precise cell density measurements.

A validation study showed a close correlation between optical and automatic cell counts ($R^2$>0.9, P<0.001 for all markers).

Figure 4:
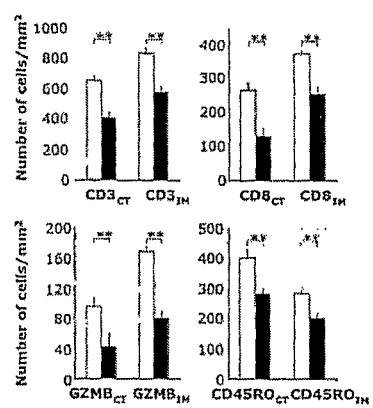
FIG. 4 shows a comparison of immune population densities in the center (CT) and the invasive margin (IM) of the tumours from patients with- (black histogram) or without-relapse (white histogram).

Immune cell distributions in specific regions were analysed in relation to the clinical outcome. Tumours from patients without relapse had a significantly higher immune cell density (CD3, CD8, CD45RO, GZMB) within each tumour region (CT or IM) (all P<0.003), than tumours from patients with relapse (FIG. 4).

Figure 5:
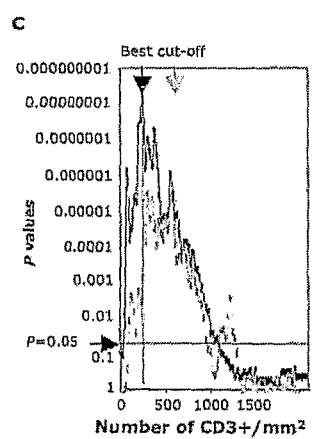
FIG. 5 The significance of all the cut-off were plotted as a function of the number of $CD3_{CT}/mm^2$ (black), and $CD3_{IM}/mm^2$ (green) for overall survival. Cut-offs for 25, 50 and 75% of the cohort are also represented for both regions. P-values above the horizontal line ($P=0.05$) are all significant.

Based on computer-signal quantification, a mean was devised to test the cut-off values of stained cells densities (for all markers in both tumour regions) for discrimination of patients for disease-free and overall survival times (1600 Log-rank tests). This permitted to define the optimal cut-off values of immune cell densities (CD3, CD8, CD45RO, GZMB), and to show that there was a large range of cut-off values in the two tumour regions that were significant (FIG. 5). According to these cut-off values, it was observed that immune-cell infiltrates (high or low densities for CD3, CD8, CD45RO, GZMB) in each region of the tumour (CT or IM) markedly distinguished patients (n=415) into groups with different median disease-free survival (DFS) (FIG. 5). Log-rank tests were highly significant for all markers studied in both tumour regions for DFS (P-values ranging from $1.5 \times 10^{-4}$ to $1.4 \times 10^{-8}$) (FIG. 5 and Table 5) and for OS (Table 6).

Figure 6:
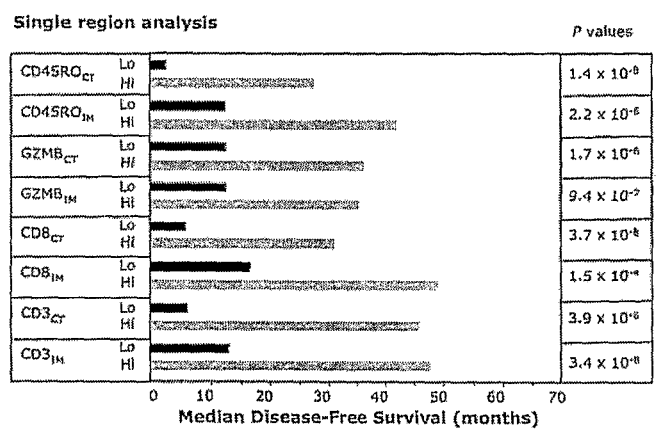
FIG. 6 shows the Median DFS of patients with high- (bottom histograms) or low-densities (upper histograms) of adaptive immune cells in each tumour region (CT or IM) is represented.
Figure 7:
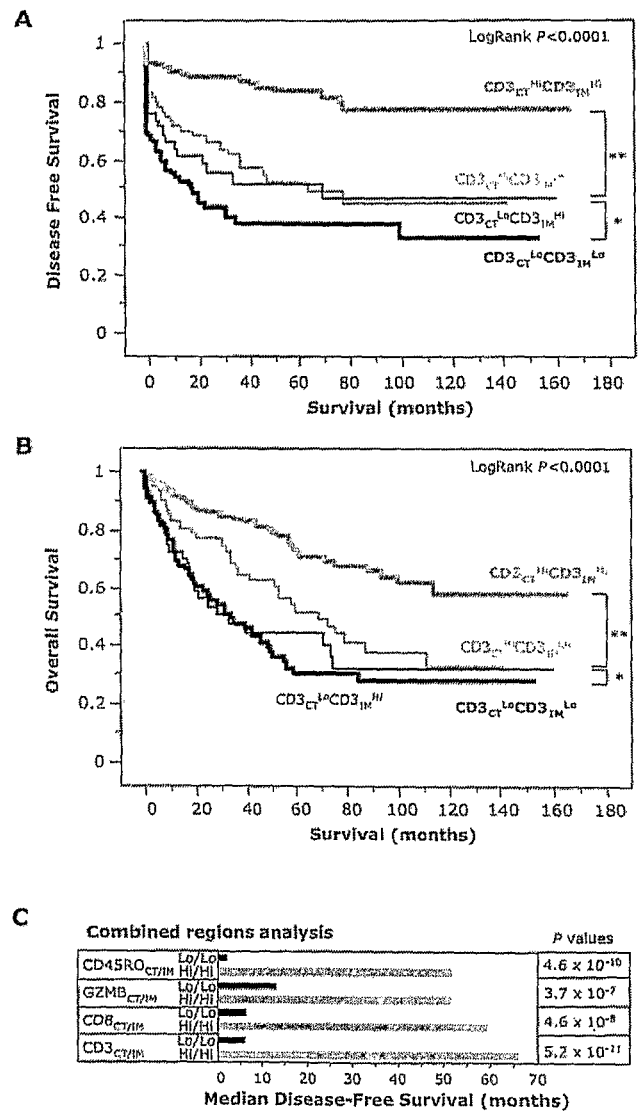
FIG. 7 shows Kaplan-Meier curves for the duration of DFS (7A) and OS (7B) according to the presence of High-CD3 density in the center of the tumour ($CD3_{CT}^{HI}$) and High-CD3 density in the invasive margin ($CD3_{IM}^{HI}$) (thick-grey), High-$CD3_{CT}$ and Low-$CD3_{IM}$ (thin-grey), Low-$CD3_{CT}$ and High-$CD3_{IM}$ (thin-black), and Low-$CD3_{CT}$ and LOW-$CD3_{IM}$ (thick-black), in 415 patients with colorectal cancer (logrank statistical test, $P<10^{-4}$ for OS and DFS; ** $p<10^{-4}$, * $P<0.05$).

It was further investigated whether the architectural distribution of the immune cells populations within the tumour (CT/IM) could influence prognosis. Kaplan-Meier curves for DFS and OS were analysed for patients with high or low CD3 densities in both tumour regions. This showed that high $CD3_{CT}/CD3_{IM}$ densities resulted in significantly better overall and disease-free survival as compared to high CD3 density in a single region (P<0.0001) (FIGS. 7A, 7B). The combined analysis of CT plus IM regions further increased median DFS differences between patients with High and Low densities for all adaptive immune markers (P-values ranging from $3.7 \times 10^{-7}$ to $6.2 \times 10^{-11}$), as compared to single analysis of CT or IM regions (FIG. 6 and FIG. 7C). Thus, median DFS for low- and high-patients were of 5.9 vs 45.9 months for CD3CT, 12.9 vs 47.8 months for $CD3_{IM}$ (FIG. 6), and of 5.9 vs 66.2 months for $CD3_{CT}/CD3_{IM}$, respectively (FIG. 7C and Table 4). Taken together, these observations indicate that disease-free and overall survival times can be predicted on the basis of the architectural distribution and of the amplitude of the in situ coordinated adaptive immune response in distinct tumour regions.

Colorectal cancer prognosis is currently based on histopathologic criteria of tumour invasion. Cox proportional-hazards regression-models adjusted for TNM-stages and tumour differentiation showed that $CD3_{CT}/CD3_{IM}$ density was an independent prognosticator for disease-free and overall survival ($P=2.8 \times 10^{-6}$, $P=3.0 \times 10^{-3}$, respectively) (Table 5). Remarkably, $CD3_{CT}/CD3_{IM}$ densities was the most significant parameter associated with disease-free survival and had a better P-value than those of T and N stages for overall survival analysis. Furthermore, all adaptive immune markers also presented with an independent prognostic value adjusted for TNM-stages and tumour differentiation for disease-free and overall survival (Table 7).

Figure 8:
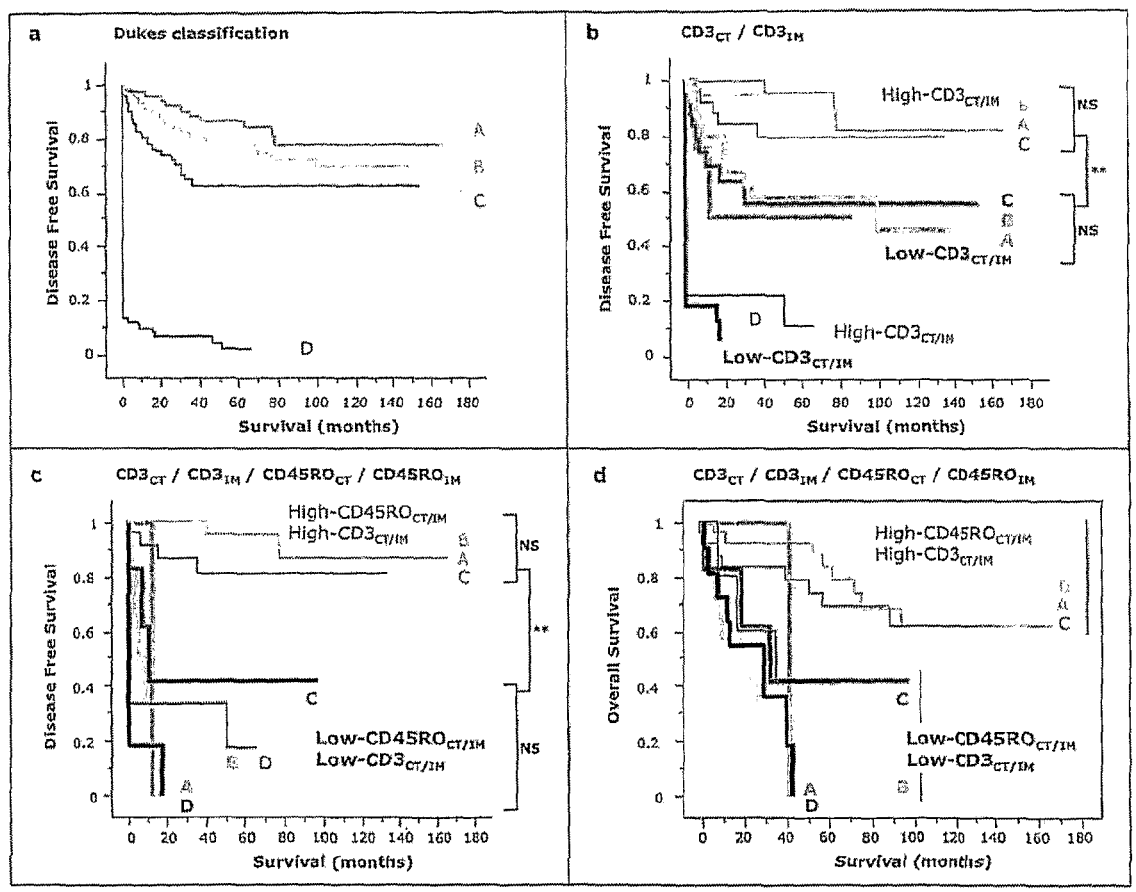
FIG. 8

Conventional staging of colorectal cancer does not account for the marked variability in outcome that exits within each stage. As the nature and the amplitude of the in situ immune response hold a strong independent prognostic value, we investigated whether evaluation of this coordinated immune response could further predict patient outcomes at each stage. We stratified patients according to Dukes' classification (FIG. 8a) and showed an influence of $CD3_{CT}/CD3_{IM}$ at all stages of the disease (FIG. 8b).

Unexpectedly, we found that a strong in situ coordinated adaptive immune response correlated with an equally favourable prognosis is regardless of the tumour invasion through the intestinal wall and extension to the local lymph-nodes (Dukes classification A, B, C). Conversely, a weak in situ adaptive immune response correlated with a very poor prognosis even in patients with minimal tumour invasion (Dukes classification A and B) (FIG. 8b).

In examples 1 to 3 above, it was demonstrated that the absence of early signs of tumour dissemination (lymphovascular and perineural invasion) and of invasion of lymph-nodes was associated with the presence of a strong density of intratumoral effector-memory T-cells (TEM).

It is in the present example further determined whether additional evaluation of memory (CD45RO+) cell density to the CD3+T cell density in both tumour regions further discriminate patients at risk of tumour recurrence. $CD3_{CT}/CD3_{IM}/CD45RO_{CT}/CD45RO_{IM}$ markedly stratified patients in two groups with high and low risk of tumour recurrence (FIG. 8c). Strikingly, low densities of these markers in both tumour regions revealed similar outcome for patients of Dukes C, B, and even A stages as compared to patients with concomitant distant metastasis (Dukes D).

Here, using high-throughput quantitative measurement of cellular and molecular immune parameters, the immunological forces in the microenvironment of human colorectal carcinoma was characterised.

Whatever the role of immunosurveillance and shaping, the present data clearly demonstrate the concept that once human colorectal carcinomas become clinically detectable, in situ natural anti-tumour immunity plays a major role in the control of tumour recurrence following surgical excision.

Beneficial in situ adaptive immune responses were not restricted to patients with minimal tumour invasion, indicating that in situ immunological forces might persist along with tumour progression. The possibility cannot be excluded that intra-tumoral lymphocytes modify tumour stroma or tumour cells, or both, in such a way that they attenuate the metastatic capacity of tumour cells.

However, the correlation of the expression of in situ adaptive immune markers, $T_{H1}$-associated molecules, and cytotoxic mediators with a low incidence of tumour recurrence provides evidence for immune-mediated rejection of persistent tumour cells following surgery.

In this way, the good prognosis value associated with the presence in situ of high density of memory-T cells (CD45RO positive cells), probably results from the critical trafficking properties and the long-lasting anti-tumour protection capacity of these cells, as shown in mice model[18].

The present evaluation of the in situ adaptive immune response that is performed, using quantitative measurements of immune cell densities at both the centre and the margin of the tumour, uncovered the importance of a coordinated adaptive immune response to control tumour recurrence.

Unexpectedly, the immunologic criteria, that are herein used, not only had a prognostic value that was superior and independent of those of the TNM and Dukes classifications, but also correlated with an equally favourable prognosis regardless of the tumour invasion.

Time to recurrence and overall survival time is shown to be governed more by the state of the local adaptive immune response rather than the presence of tumour spreading through the intestinal wall and to regional lymph node(s).

This novel insight has several important implications and may change the understanding of the evolution of carcinoma, including colorectal carcinoma. In addition, the criteria that have been used, should lead to a re-evaluation of the currently used classification of colorectal carcinoma, and indicate with more precision, those patients at high-risk of tumour recurrence who may benefit from adjuvant therapy (including immunotherapy).

The utility of immunohistochemistry, combined with the availability of an extensive set of antibodies against immune markers, should facilitate the application of our approach to other tumours.

Example 5

Additional Results Relating to the Correlation between (i) Adaptive Immune Response and (i) Recurrence and Survival Times Genomic and in situ immunostaining analyses were conducted on 75 and 415 patients, respectively (Table 11-S1). The data were entered into a dedicated Tumoral MicroEnvironment Database (TME.db; access available upon request). We used quantitative real-time PCR to evaluate the expression levels of Immune-genes related to inflammation, T-helper 1 ($T_{H1}$) adaptive immunity, and immunosuppression. These genes showed variable expression patterns in the 75 tumors studied. Correlation analyses performed between all genes showed 39 highly significant combinations (P<0.0001) (Table 4). A dominant cluster of co-modulated genes for $T_{H1}$ adaptive immunity was identified (T-box transcription factor 21 (T-bet), interferon regulatory factor 1 (IRF-1), IFNγ, CD3ζ, CD8, granulysin (GLNY), granzyme B (GZMB)). A hierarchical tree structure classifying the patients according to the expression levels of genes from this cluster revealed an inverse correlation between expression of these genes and tumor recurrence (P value comparing patient groups, all P<0.05). These data shows that $T_{H1}$ adaptive immunity has a beneficial effect on clinical outcome.

Tissue-MicroArrays were next used to investigate the in situ adaptive immune response in the center of the tumor (CT) and the invasive margin (IM) of 415 CRCs. Immunostaining for total T lymphocytes (CD3), CD8 T cell effectors and their associated cytotoxic molecule (GZMB), and memory T cells (CD45RO) were quantified using a dedicated image analysis workstation. Tumors from patients without recurrence had higher immune cell densities (CD3, CD8, GZMB, CD45RO) within each tumor region (CT, IM), than did those from patients whose tumors had recurred, as it was formerly observed in Example 4 above. In each tumor region (CT, IM) and for each marker (CD3, CD8, GZMB, CD45RC) there was a statistically significant correlation between immune cells density and patients outcome for a large range of cut-off values (FIG. 9-S5). In particular, using the cut-off that yielded the minimum P-value for disease-free survival, the densities of CD3+, CD8+, GZMB+, and CD45RO+ cells in each tumor region (CT and IM) allowed to stratify patients into groups with statistically different disease-free survival (P-values corrected after (23), ranging from $1.0\times10^{-2}$ to $4.8\times10^{-6}$) and overall survival (P-values ranging from $5.5\times10^{-3}$ to $7.9\times10^{8}$) (and Tables 12, 13-S3, S4). Re-analyses of the data using 100 repetitions of 2-fold cross-validations after (24) (Tables 12, 13-S3, S4) or setting the cut-off at the median of the data sets (Tables 14, 1-S5, S6), provided concordant results as to the prognostic value of each immune parameter.

It was then investigated whether the combined analysis of tumor regions could improve the prediction of patients' survival. For all the markers of adaptive immunity. (CD3, CD8, GZMB and CD45RO), the combined analysis of CT plus IM regions (HiHi vs LoLo) increased disease-free and overall survival time differences between patients, as compared to single region analysis (Hi vs Lo) (Tables 12-15-S3-S6). Data were also analyzed using 2-fold cross-validation after (24) (100*CV for each marker), showing highly significant differences (Tables 12, 13-S3, S4). $CD3_{CT}/CD3_{IM}$ was associated with the smallest P values for disease-free and overall survival analyses (P=$7.6\times10^{-8}$ and P=$4.0\times10^{-7}$ respectively) (Tables 12, 13-S3, S4), To confirm these results, an additional cohort of patients different from the first series and a third cohort of CRCs from another hospital were analyzed. For each cohort, the median cut-off values for $CD3_{CT}/CD3_{IM}$ (50% of patients with a high- and 50% of patients with a low-density) were determined. The two independent cohorts confirmed the data obtained on the first series. All statistical analyses were also performed in the subgroup of patients without concomitant distant metastasis (UICC-TNM stages I, II, and III). Significant P-values were observed for $CD_{CT/IM}$, $CD8_{CT/IM}$ and $CD45RO_{CT/IM}$ for disease-free survival and overall survival analyses (Tables 16-19-S7-S10).

It was determined whether these immune criteria could discriminate patient outcome at each step of cancer progression. Patients were stratified according to the UICC-TNM classification (25) (FIG. 10A). A strong in situ immune reaction in both tumor regions correlated with a favorable prognosis regardless of the local extent of the tumor and invasion to regional lymph-nodes (stages I, II, and III). Conversely, a weak in situ immune reaction in both tumor regions correlated with a poor prognosis even in patients with minimal tumor invasion (stage I) (FIG. 10B). We recently demonstrated the importance of the density of CD45RO+ memory T cells in limiting tumor dissemination of CRCs (22). We found that patients with low densities of CD3+ cells and CD45RO+ memory T cells in both tumor regions (CT and IM) had a very poor prognosis, similar to patients with concomitant distant metastasis (stage IV) (FIG. 10C). In multivariate analysis, after adjusting for tumor invasion (T-stage), tumor differentiation and lymph-node invasion (N-stage), $CD3_{CT}/CD3_{IM}$ density (HiHi, Heterogeneous, LoLo) remained an independent prognostic factor with the highest hazard ratio and the smallest P-value in disease-free survival analysis (HR of 2.391; P=$1.4\times10^{-6}$ corrected after (26)) (Table 20-S11). $CD3_{CT}/CD3_{IM}$ density was the unique independent parameter associated with overall survival (HR of 1.89 P=$1.2\times10^{-5}$) (Table 21-S12). The histopathological parameters were no longer associated with disease-free and overall survival in patients with coordinated high or low densities of the immune markers in both tumor regions (HiHi versus LoLo) (Tables and 21-S11 and S12).

Further, as shown in FIGS. 11 and 12, the in vitro prognosis method according to the invention may be successfully performed for the prognosis of various types of cancers, as illustrated by the prediction of the outcome of colon and rectum cancers.

Still further, as illustrated in FIG. 13, the in vitro prognosis method according to the invention has proved highly reliable for prognosis of the outcome of cancers in patients undergoing cancers at an rearly stage.

Yet further, as illustrated in FIG. 14, the in vitro prognosis method according to the invention has been shown to allow an accurate prognosis of outcome of cancers, using, as the one or more biological markers, a combination or a set of six biological markers, namely PDCD1LG1, VEGF, TNFRSF6B, IRF1, IL8RA and SELL, that were quantified by a gene expression analysis method, more precisely, Real-Time PCR analysis.

In summary, the results presented in Example 5 show that once human CRCs become clinically detectable, the adaptive immune response plays a role in preventing tumor recurrence.

A positive correlation was found between the presence of markers for $T_{H1}$ polarization, cytotoxic and memory T cells and a low incidence of tumor recurrence.

Thus, it was found herein that the type, the density, and the location of immune cells in CRCs had a prognostic value that was superior and independent of those of the UICC-TNM classification (L. Sobin et al., 2002, *TNIM classification of malignant tumors*. 6$^{th}$, Ed., Wiley-Liss, New York) These results show that time to recurrence and overall survival time are be mostly governed by the state of the local adaptive immune response.

The new immunological tool provided by the present invention may lead to revision of the current indicators of clinical outcome and may help identify the high-risk patients who would benefit the most from adjuvant therapy.

TABLE 1

| | Disease-free and Overall Survival (n = 959 patients) ||||||||
|---|---|---|---|---|---|---|---|---|
| | | Disease Free Survival (DFS) ||| | Overall Survival (OS) |||
| | N. of patients | Rate at 5 yr % | Median months | P value* | | Rate at 5 yr % | Median months | P value* |
| T stage | | | | <0.001 | s | | | <0.001 | s |
| pTis | 39 | 48.7 | 55.7 | | | 48.7 | 55.7 | |
| pT1 | 54 | 42.6 | 52.2 | | | 44.4 | 53.8 | |
| pT2 | 156 | 40.4 | 43.6 | | | 44.2 | 49.1 | |
| pT3 | 502 | 23.7 | 16.5 | | | 26.7 | 25.8 | |
| pT4 | 208 | 16.8 | 1.6 | | | 17.8 | 16.8 | |
| N stage | | | | <0.001 | s | | | <0.001 | s |
| N0 | 568 | 35.4 | 34.6 | | | 38.6 | 43.1 | |
| N+ | 384 | 15.1 | 4.3 | | | 16.7 | 16.9 | |
| M stage | | | | <0.001 | s | | | <0.001 | s |
| M0 | 747 | 34.5 | 32.6 | | | 37.6 | 41.1 | |
| M+ | 212 | 0.5 | 0.1 | | | 0.9 | 12.3 | |
| Dukes classification | | | | <0.001 | s | | | <0.001 | s |
| A | 83 | 47.0 | 55.6 | | | 47.0 | 55.6 | |
| B | 438 | 37.2 | 39.2 | | | 41.1 | 46.8 | |
| C | 227 | 24.7 | 19.5 | | | 27.3 | 28.1 | |
| D | 212 | 0.5 | 0.1 | | | 1.0 | 12.1 | |
| Sex | | | | 0.38 | ns | | | 0.47 | ns |
| Male | 494 | 25.9 | 16.4 | | | 28.5 | 29.4 | |
| Female | 465 | 28.2 | 19.3 | | | 30.5 | 27.3 | |
| Localization | | | | 0.20 | ns | | | 0.14 | ns |
| RC | 243 | 23.9 | 14.5 | | | 24.7 | 19.7 | |
| TC | 51 | 7.8 | 9.2 | | | 9.8 | 22.2 | |
| LC | 84 | 28.6 | 15.3 | | | 31.0 | 27.2 | |
| SC | 298 | 26.8 | 14.7 | | | 29.5 | 29.5 | |
| R | 287 | 32.4 | 32.1 | | | 36.5 | 40.4 | |
| Differentiation | | | | 0.26 | ns | | | 0.09 | ns |
| Well | 737 | 30.7 | 21.7 | | | 33.6 | 33.2 | |
| Moderate | 187 | 14.4 | 9.3 | | | 15.5 | 17.8 | |
| Poor | 35 | 17.1 | 2.6 | | | 17.1 | 11.6 | |
| Mucinous Colloid | | | | 0.087 | ns | | | 0.270 | ns |
| No | 766 | 28.2 | 19.5 | | | 30.9 | 30.9 | |
| Yes | 193 | 22.3 | 14.9 | | | 23.8 | 21.8 | |
| N. of lymph nodes analyzed | | | | 0.11 | ns | | | 0.69 | ns |
| <8 | 426 | 34.0 | 31.0 | | | 37.1 | 40.0 | |
| ≧8 | 533 | 21.4 | 12.9 | | | 23.5 | 23.2 | |
| VE | | | | <0.001 | s | | | <0.001 | s |
| No | 797 | 31.0 | 23.6 | | | 33.9 | 34.1 | |
| Yes | 162 | 7.4 | 1.4 | | | 8.0 | 13.9 | |
| LI | | | | <0.001 | s | | | <0.001 | s |
| No | 803 | 29.5 | 21.6 | | | 32.1 | 32.0 | |
| Yes | 156 | 14.1 | 0.5 | | | 16.0 | 16.1 | |
| PI | | | | <0.001 | s | | | <0.001 | s |
| No | 860 | 28.3 | 20.7 | | | 32.0 | 32.0 | |
| Yes | 99 | 7.1 | 0.1 | | | 8.1 | 16.2 | |
| VELIPI (VE or LI or PI) | | | | <0.001 | s | | | <0.001 | s |
| No | 702 | 32.4 | 26.9 | | | 35.5 | 35.5 | |
| Yes | 257 | 12.1 | 3.3 | | | 13.2 | 16.8 | |
| VE or LI | | | | <0.001 | s | | | <0.001 | s |
| No | 716 | 31.6 | 24.4 | | | 35.2 | 35.0 | |
| Yes | 243 | 13.6 | 3.7 | | | 12.6 | 16.3 | |
| VE and LI | | | | <0.001 | s | | | <0.001 | s |
| No | 884 | 28.3 | 19.7 | | | 31.2 | 31.0 | |
| Yes | 75 | 12.0 | 0.2 | | | 9.3 | 11.9 | |
| VE and LI and PI | | | | <0.001 | s | | | <0.001 | s |
| No | 911 | 28.0 | 19.5 | | | 30.7 | 30.5 | |
| Yes | 48 | 8.3 | 0.1 | | | 8.3 | 9.5 | |

RC: Right Colon,
TC: Transverse Colon,
LC: Left Colon,
SC: Sigmoid Colon,
R: Rectum
VE: Vascular Emboli,
LI: Lymphatic Invasion,
PI: Perineural Invasion
*P value LogRank test

TABLE 2

List of genes

| Gene | Name | Acc. number | Chr. Loc. |
|---|---|---|---|
| IL10 | Interleukin 10 | NM_000572 | 1q31-q32 |
| IL8 | Interleukin 8 | NM_000584 | 4q13-q21 |
| IFNG | Interferon, gamma | NM_000619 | 12q14 |
| TGFB1 | transforming growth factor, beta 1 | NM_000660 | 19q13.2 |
| PTGS2 | Prostaglandin-endoperoxide synthase 2 (Cox2) | NM_000963 | 1q25.2 |
| CEACAM1 | carcinoembryonic antigen-related cell adhesion molecule 1 | NM_001712 | 19q13.2 |
| IRF1 | Interferon regulatory factor 1 | NM_002198 | 5q31.1 |
| MMP7 | matrix metalloproteinase 7 (matrilysin, uterine) | NM_002423 | 11q21-q22 |
| VEGF | vascular endothelial growth factor | NM_003376 | 6p12 |
| GZMB | granzyme B | NM_004131 | 14q11.2 |
| TBX21 | T-box 21 (T-bet) | N_013351 | 17q21.2 |
| B7H3 | B7 homolog 3 | NM_025240 | 15q23-q24 |
| CD8A | CD8 antigen, alpha polypeptide (p32) | NM_001768 | 2p12 |
| GNLY | Granulysin | NM_006433 | 2p12-q11 |
| BIRC5 | baculoviral IAP repeat-containing 5 (survivin) | NM_001168 | 17q25 |
| CD3Z | CD3Z antigen, zeta polypeptide (TiT3 complex) | NM_198053 NM_000734 | 1q22-q23 |
| TNFRSF10A | tumor necrosis factor receptor superfamily, member 10a | NM_003844 | 8p21 |
| CD4 | CD4 antigen (p55) | NM_000616 | 12pter-p12 |

TABLE 3

List of antibodies

| Antibody | Common name | Clone | Isotype | Fluorochrom | specie | Manufacturer |
|---|---|---|---|---|---|---|
| CCR5 | CCR5 | 45531 | IgG2b | FITC | mouse | R&D systems |
| CCR7 | CCR7 | 3D12 | IgG2a | PE | rat | BD pharmingen |
| CD103 | Integrin alpha E | Ber-ATC8 | IgG1 | PE | mouse | BD pharmingen |
| CD119 | IFN-gamma-R1 | BB1E2 | IgG2a | FITC | mouse | serotec |
| CD120a | TNFR1 | H398 | IgG2a | PE | mouse | serotec |
| CD120b | TNFR2 | MR2-1 | IgG1 | PE | mouse | serotec |
| CD122 | IL-2R-beta | MIK-beta1 | IgG2a | FITC | mouse | serotec |
| CD127 | IL-7R-alpha | R34.34 | IgG1 | PE | mouse | beckman coulter |
| CD134 | OX40L-R | ACT35 | IgG1 | FITC | mouse | BD pharmingen |
| CD14 | CD14 | M5E2 | IgG2a | APC | mouse | BD pharmingen |
| CD152 | CTLA-4 | BNI3 | IgG2a | APC | mouse | BD pharmingen |
| CD154 | CD40L | TRAP1 | IgG1 | FITC | mouse | BD pharmingen |
| CD178 | FasL | NOK1 | IgG1 | — | mouse | BD pharmingen |
| CD183 | CXCR3 | 1C6/CXCR3 | IgG1 | APC | mouse | BD pharmingen |
| CD184 | CXCR4 | 12G5 | IgG2a | APC | mouse | BD pharmingen |
| CD19 | CD19 | HIB19 | IgG1 | FITC | mouse | BD pharmingen |
| CD1a | CD1a | HI149 | IgG1 | FITC | mouse | BD pharmingen |
| CD210 | IL-10R-alpha | 3F9 | IgG2a | PE | rat | BD pharmingen |
| CD25 | IL-2R-alpha | M-A251 | IgG1 | APC | mouse | BD pharmingen |
| CD26 | Dipeptidyl-peptidase IV | M-A261 | IgG1 | PE | mouse | BD pharmingen |
| CD27 | CD27 | M-T271 | IgG1 | PE | mouse | BD pharmingen |
| CD28 | CD28 | CD28.2 | IgG1 | APC | mouse | BD pharmingen |
| CD3 | CD3ε | UCHT1 | IgG1 | FITC | mouse | BD pharmingen |
| CD3 | CD3$$ | UCHT1 | IgG1 | CyCr | mouse | BD pharmingen |
| CD3 | CD3ε | S4.1 | IgG2a | PE-Cy5 | mouse | serotec |
| CD32 | FcγRII | AT10 | IgG1 | FITC | mouse | serotec |
| CD4 | CD4 | RPA-T4 | IgG1 | FITC | mouse | BD pharmingen |
| CD4 | CD4 | RPA-T4 | IgG1 | PE | mouse | BD pharmingen |
| CD44 | CD44 | G44-26 | IgG2b | APC | mouse | BD pharmingen |
| CD45 | CD45 | HI30 | IgG1 | CyCr | mouse | BD pharmingen |
| CD45Ra | CD45Ra | HI100 | IgG2b | FITC | mouse | BD pharmingen |
| CD45Ro | CD45Ro | UCHTL1 | IgG2a | APC | mouse | BD pharmingen |
| CD47 | CD47 | B6H12 | IgG1 | PE | mouse | BD pharmingen |
| CD49d | VLA-4 | 9F10 | IgG1 | PE | mouse | BD pharmingen |
| CD5 | CD5 | UCHT2 | IgG1 | PE | mouse | BD pharmingen |
| CD54 | ICAM-1 | HA58 | IgG1 | PE | mouse | BD pharmingen |
| CD56 | CD56 | B159 | IgG1 | PE | mouse | BD pharmingen |
| CD62L | L-selectin | Dreg56 | IgG1 | FITC | mouse | BD pharmingen |
| CD69 | CD69 | FN50 | IgG1 | APC | mouse | BD pharmingen |
| CD7 | CD7 | M-T701 | IgG1 | FITC | mouse | BD pharmingen |
| CD8 | CD8 | RPA-T8 | IgG1 | APC | mouse | BD pharmingen |
| CD8 | CD8 | HIT8a | IgG1 | PE | mouse | BD pharmingen |
| CD80 | B7.1 | L307.4 | IgG1 | PE | mouse | BD pharmingen |
| CD83 | CD83 | HB15e | IgG1 | PE | mouse | BD pharmingen |
| CD86 | B7.2 | FUN-1 | IgG1 | FITC | mouse | BD pharmingen |
| CD95 | Fas | DX2 | IgG1 | APC | mouse | BD pharmingen |
| CD97 | CD97 | VIM3b | IgG1 | FITC | mouse | BD pharmingen |
| CD98 | CD98 | UM7F8 | IgG1 | FITC | mouse | BD pharmingen |
| CXCR6 | CXCR6 | 56811 | IgG2b | PE | mouse | R&D systems |
| GITR | GITR | polyclonal | IgG | — | goat | R&D systems |
| HLA-DR | HLA-DR | G46.6(L243) | IgG2a | FITC | mouse | BD pharmingen |

TABLE 3-continued

List of antibodies

| Antibody | Common name | Clone | Isotype | Fluorochrom | specie | Manufacturer |
|---|---|---|---|---|---|---|
| ICOS | ICOS | C394.4A | IgG | PE | mouse | cliniciences |
| IFNγRII | IFNγRII | polyclonal | IgG | — | goat | R&D systems |
| IL-18Rα | IL-18Rα | 70625 | IgG1 | PE | mouse | R&D systems |
| KIR-NKAT2 | KIR-NKAT2 | DX27 | IgG2a | FITC | mouse | BD pharmingen |
| PD1 | PD1 | J116 | IgG1 | PE | mouse | cliniciences |
| Streptavidin | Streptavidin | — | — | APC | — | BD pharmingen |
| TCR αβ | TCR αβ | T10B9.A1-31 | IgM | FITC | mouse | BD pharmingen |
| TGFRII | TGFRII | 25508 | IgG1 | FITC | mouse | R&D systems |

TABLE 4

Correlation analysis

| Genes | Correlation | 95% CI | P value |
|---|---|---|---|
| CD8A - TBX21 | 0.902 | (0.848/0.938) | <0.0001 |
| CD3Z - CD8A | 0.797 | (0.694/0.868) | <0.0001 |
| CD3Z - TBX21 | 0.784 | (0.676/0.859) | <0.0001 |
| B7H3 - TGFB1 | 0.760 | (0.643/0.843) | <0.0001 |
| IFNG - TBX21 | 0.759 | (0.635/0.844) | <0.0001 |
| CD4 - CD8A | 0.738 | (0.612/0.828) | <0.0001 |
| CD8A - IFNG | 0.728 | (0.592/0.823) | <0.0001 |
| CD4 - TBX21 | 0.727 | (0.597/0.820) | <0.0001 |
| CD3Z - CD4 | 0.719 | (0.586/0.815) | <0.0001 |
| CD4 - TGFB1 | 0.678 | (0.531/0.786) | <0.0001 |
| CD8A - GNLY | 0.671 | (0.522/0.781) | <0.0001 |
| IFNG - IRF1 | 0.664 | (0.505/0.779) | <0.0001 |
| GNLY - IFNG | 0.663 | (0.505/0.779) | <0.0001 |
| IRF1 - TBX21 | 0.656 | (0.502/0.770) | <0.0001 |
| IL8 - PTGS2 | 0.643 | (0.485/0.761) | <0.0001 |
| GNLY - TBX21 | 0.627 | (0.464/0.749) | <0.0001 |
| CD3Z - IRF1 | 0.617 | (0.451/0.742) | <0.0001 |
| CD8A - IRF1 | 0.617 | (0.451/0.742) | <0.0001 |
| CD3Z - GNLY | 0.613 | (0.446/0.739) | <0.0001 |
| CD3Z - IFNG | 0.605 | (0.428/0.737) | <0.0001 |
| GZMB - IFNG | 0.604 | (0.422/0.739) | <0.0001 |
| GNLY - IRF1 | 0.597 | (0.425/0.727) | <0.0001 |
| IL10 - TGFB1 | 0.596 | (0.424/0.726) | <0.0001 |
| CD8A - IL10 | 0.586 | (0.411/0.719) | <0.0001 |
| CD4 - IL10 | 0.583 | (0.408/0.717) | <0.0001 |
| CD8A - GZMB | 0.574 | (0.392/0.713) | <0.0001 |
| GZMB - TBX21 | 0.548 | (0.359/0.693) | <0.0001 |
| CD3Z - GZMB | 0.538 | (0.347/0.687) | <0.0001 |
| CD4 - IRF1 | 0.520 | (0.330/0.670) | <0.0001 |
| GNLY - GZMB | 0.520 | (0.324/0.673) | <0.0001 |
| B7H3 - IL10 | 0.517 | (0.326/0.668) | <0.0001 |
| CD4 - GZMB | 0.507 | (0.309/0.663) | <0.0001 |
| GZMB - IRF1 | 0.504 | (0.305/0.661) | <0.0001 |
| IL10 - TBX21 | 0.494 | (0.297/0.650) | <0.0001 |
| CD4 - IFNG | 0.493 | (0.289/0.655) | <0.0001 |
| B7H3 - CD4 | 0.475 | (0.275/0.636) | <0.0001 |
| CD8A - TGFB1 | 0.466 | (0.264/0.628) | <0.0001 |
| CD3Z - IL10 | 0.459 | (0.255/0.623) | <0.0001 |
| CD4 - GNLY | 0.454 | (0.250/0.619) | <0.0001 |
| TBX21 - TGFB1 | 0.433 | (0.226/0.603) | 0.0001 |
| GNLY - IL10 | 0.413 | (0.202/0.587) | 0.0002 |
| CD3Z - TGFB1 | 0.398 | (0.185/0.575) | 0.0004 |
| IFNG - IL10 | 0.390 | (0.168/0.575) | 0.0009 |
| B7H3 - VEGF | 0.371 | (0.155/0.554) | 0.0011 |
| B7H3 - IL8 | 0.370 | (0.152/0.553) | 0.0012 |
| CEACAM1 - IRF1 | 0.359 | (0.140/0.544) | 0.0017 |
| IL10 - IRF1 | 0.355 | (0.136/0.541) | 0.0019 |
| IRF1 - VEGF | 0.351 | (0.131/0.538) | 0.0022 |
| B7H3 - MMP7 | 0.335 | (0.112/0.526) | 0.0038 |
| B7H3 - PTGS2 | 0.333 | (0.112/0.523) | 0.0037 |
| IRF1 - TGFB1 | 0.333 | (0.111/0.523) | 0.0038 |
| IL10 - PTGS2 | 0.325 | (0.103/0.517) | 0.0047 |
| GZMB - IL10 | 0.320 | (0.092/0.517) | 0.0066 |
| CD4 - VEGF | 0.316 | (0.093/0.509) | 0.0062 |
| GZMB - TGFB1 | 0.306 | (0.076/0.504) | 0.0097 |
| IL8 - MMP7 | 0.295 | (0.068/0.493) | 0.0116 |
| TBX21 - VEGF | 0.294 | (0.069/0.491) | 0.0113 |
| CEACAM1 - VEGF | 0.292 | (0.066/0.489) | 0.0119 |
| TGFB1 - VEGF | 0.290 | (0.065/0.488) | 0.0124 |
| BIRC5 - IRF1 | 0.265 | (0.037/0.466) | 0.0234 |
| GNLY - TGFB1 | 0.257 | (0.029/0.460) | 0.0278 |
| PTGS2 - TGFB1 | 0.257 | (0.028/0.459) | 0.0281 |
| MMP7 - VEGF | 0.251 | (0.020/0.456) | 0.0332 |
| IFNG - TGFB1 | 0.239 | (0.001/0.452) | 0.0492 |
| IRF1 - TNFRSF10A | 0.238 | (0.009/0.444) | 0.042 |
| BIRC5 - PTGS2 | 0.224 | (−0.007/0.431) | 0.0571 |
| IL8 - TGFB1 | 0.223 | (−0.007/0.431) | 0.0578 |
| B7H3 - IRF1 | 0.222 | (−0.009/0.430) | 0.059 |
| MMP7 - TGFB1 | 0.221 | (−0.012/0.430) | 0.0622 |
| B7H3 - CD8A | 0.216 | (−0.015/0.425) | 0.0664 |
| GZMB - VEGF | 0.209 | (−0.028/0.423) | 0.0829 |
| CD3Z - VEGF | 0.207 | (−0.024/0.418) | 0.0784 |
| IFNG - IL8 | 0.206 | (−0.034/0.424) | 0.0922 |
| CD3Z - CEACAM1 | 0.204 | (−0.027/0.415) | 0.0836 |
| CD8A - VEGF | 0.203 | (−0.028/0.414) | 0.0846 |
| IL10 - IL8 | 0.196 | (−0.036/0.408) | 0.0967 |
| BIRC5 - IFNG | 0.195 | (−0.045/0.414) | 0.111 |
| GZMB - IL8 | 0.194 | (−0.043/0.410) | 0.1087 |
| B7H3 - TBX21 | 0.191 | (−0.041/0.403) | 0.1056 |
| B7H3 - CD3Z | 0.188 | (−0.044/0.401) | 0.1109 |
| CD4 - MMP7 | 0.181 | (−0.052/0.397) | 0.1274 |
| CEACAM1 - TBX21 | 0.174 | (−0.059/0.388) | 0.1416 |
| GNLY - PTGS2 | 0.173 | (−0.059/0.388) | 0.1435 |
| MMP7 - PTGS2 | 0.162 | (−0.073/0.379) | 0.1748 |
| BIRC5 - GZMB | 0.161 | (−0.077/0.381) | 0.1842 |
| B7H3 - GZMB | 0.160 | (−0.078/0.381) | 0.1862 |
| CD4 - TNFRSF10A | 0.160 | (−0.072/0.377) | 0.176 |
| IFNG - TNFRSF10A | 0.156 | (−0.086/0.380) | 0.2048 |
| GNLY - TNFRSF10A | 0.153 | (−0.079/0.370) | 0.1957 |
| TBX21 - TNFRSF10A | 0.147 | (−0.086/0.365) | 0.2157 |
| BIRC5 - IL8 | 0.145 | (−0.088/0.363) | 0.2225 |
| TNFRSF10A - VEGF | 0.136 | (−0.097/0.355) | 0.2518 |
| B7H3 - TNFRSF10A | 0.135 | (−0.098/0.355) | 0.2541 |
| CD8A - TNFRSF10A | 0.134 | (−0.099/0.354) | 0.2577 |
| GZMB - PTGS2 | 0.134 | (−0.104/0.358) | 0.2702 |
| CEACAM1 - TNFRSF10A | 0.133 | (−0.100/0.352) | 0.2641 |
| B7H3 - IFNG | 0.126 | (−0.116/0.353) | 0.3088 |
| IFNG - VEGF | 0.123 | (−0.119/0.351) | 0.3177 |
| CD3Z - TNFRSF10A | 0.117 | (−0.117/0.338) | 0.3269 |
| BIRC5 - CEACAM1 | 0.109 | (−0.124/0.331) | 0.3597 |
| GNLY - IL8 | 0.106 | (−0.128/0.328) | 0.3754 |
| IFNG - PTGS2 | 0.106 | (−0.136/0.336) | 0.3903 |
| GZMB - TNFRSF10A | 0.104 | (−0.135/0.331) | 0.3942 |
| CEACAM1 - IFNG | 0.093 | (−0.148/0.325) | 0.4506 |
| B7H3 - GNLY | 0.090 | (−0.143/0.313) | 0.4514 |
| BIRC5 - GNLY | 0.088 | (−0.145/0.311) | 0.4628 |
| CEACAM1 - GZMB | 0.087 | (−0.151/0.316) | 0.4736 |
| CEACAM1 - GNLY | 0.082 | (−0.151/0.306) | 0.4911 |
| IL10 - MMP7 | 0.081 | (−0.153/0.307) | 0.499 |
| IL8 - VEGF | 0.078 | (−0.155/0.303) | 0.5132 |
| BIRC5 - MMP7 | 0.077 | (−0.157/0.304) | 0.5192 |
| CD8A - CEACAM1 | 0.076 | (−0.157/0.301) | 0.5232 |
| TGFB1 - TNFRSF10A | 0.071 | (−0.162/0.296) | 0.5538 |
| BIRC5 - VEGF | 0.065 | (−0.168/0.291) | 0.5855 |
| IRF1 - PTGS2 | 0.064 | (−0.169/0.289) | 0.594 |
| IRF1 - MMP7 | 0.063 | (−0.171/0.290) | 0.6012 |

TABLE 4-continued

Correlation analysis

| Genes | Correlation | 95% CI | P value |
|---|---|---|---|
| PTGS2 - VEGF | 0.063 | (−0.170/0.289) | 0.5995 |
| CEACAM1 - MMP7 | 0.035 | (−0.199/0.264) | 0.7742 |
| IL10 - TNFRSF10A | 0.032 | (−0.199/0.261) | 0.786 |
| IL8 - IRF1 | 0.021 | (−0.211/0.249) | 0.8633 |
| CD4 - CEACAM1 | 0.014 | (−0.217/0.243) | 0.9088 |
| BIRC5 - TBX21 | 0.013 | (−0.218/0.242) | 0.9124 |
| IFNG - MMP7 | 0.009 | (−0.231/0.249) | 0.9402 |
| CD3Z - MMP7 | 0.005 | (−0.227/0.236) | 0.968 |
| CEACAM1 - PTGS2 | −0.001 | (−0.231/0.229) | 0.9923 |
| IL10 - VEGF | −0.004 | (−0.234/0.226) | 0.9721 |
| CD8A - PTGS2 | −0.008 | (−0.238/0.222) | 0.9448 |
| GZMB - MMP7 | −0.008 | (−0.244/0.229) | 0.947 |
| IL8 - TNFRSF10A | −0.017 | (−0.246/0.214) | 0.8892 |
| GNLY - VEGF | −0.023 | (−0.252/0.208) | 0.8484 |
| PTGS2 - TBX21 | −0.036 | (−0.264/0.196) | 0.7631 |
| MMP7 - TBX21 | −0.049 | (−0.277/0.185) | 0.6844 |
| BIRC5 - CD8A | −0.051 | (−0.278/0.181) | 0.6675 |
| CD3Z - PTGS2 | −0.051 | (−0.278/0.181) | 0.6683 |
| BIRC5 - CD3Z | −0.054 | (−0.280/0.179) | 0.6528 |
| B7H3 - CEACAM1 | −0.063 | (−0.289/0.169) | 0.5972 |
| PTGS2 - TNFRSF10A | −0.066 | (−0.292/0.166) | 0.5782 |
| CD8A - MMP7 | −0.086 | (−0.311/0.149) | 0.4739 |
| B7H3 - BIRC5 | −0.095 | (−0.318/0.138) | 0.4236 |
| CD4 - IL8 | −0.101 | (−0.323/0.133) | 0.3987 |
| CEACAM1 - IL8 | −0.101 | (−0.323/0.132) | 0.3979 |
| CD4 - PTGS2 | −0.111 | (−0.333/0.122) | 0.3494 |
| CEACAM1 - IL10 | −0.111 | (−0.333/0.122) | 0.3495 |
| IL8 - TBX21 | −0.131 | (−0.350/0.102) | 0.2714 |
| BIRC5 - IL10 | −0.134 | (−0.353/0.099) | 0.2583 |
| CD8A - IL8 | −0.163 | (−0.378/0.070) | 0.1701 |
| MMP7 - TNFRSF10A | −0.217 | (−0.427/0.015) | 0.0668 |
| BIRC5 - TGFB1 | −0.218 | (−0.426/0.013) | 0.0643 |
| BIRC5 - CD4 | −0.231 | (−0.438/−0.001) | 0.0489 |
| CEACAM1 - TGFB1 | −0.239 | (−0.445/−0.010) | 0.0413 |
| GNLY - MMP7 | −0.241 | (−0.448/−0.010) | 0.0408 |
| BIRC5 - TNFRSF10A | −0.243 | (−0.448/−0.014) | 0.0378 |
| CD3Z - IL8 | −0.258 | (−0.461/−0.030) | 0.0272 |

TABLE 5

Disease Free Survival (DFS)

| | N. of patients | Rate at 2 yr % | Rate at 4 yr % | Rate at 5 yr % | Median months | P value |
|---|---|---|---|---|---|---|
| GZM-CT | | | | | | 1.66E−06 |
| Hi | 163 | 57.66 | 46.62 | 41.71 | 36.5 | |
| Lo | 191 | 35.93 | 26.04 | 21.87 | 12.4 | |
| GZM-IM | | | | | | 9.42E−07 |
| Hi | 175 | 56.00 | 44.57 | 38.28 | 36.6 | |
| Lo | 129 | 38.76 | 31.00 | 26.36 | 12.9 | |
| CD45RO-CT | | | | | | 1.43E−08 |
| Hi | 294 | 51.70 | 40.81 | 36.05 | 27.4 | |
| Lo | 67 | 20.58 | 11.76 | 8.82 | 2.4 | |
| CD45RO-IM | | | | | | 2.16E−06 |
| Hi | 190 | 56.31 | 46.84 | 42.10 | 42.0 | |
| Lo | 178 | 35.19 | 24.58 | 20.11 | 12.4 | |
| CD8-CT | | | | | | 3.68E−08 |
| Hi | 227 | 54.18 | 43.17 | 38.32 | 31.1 | |
| Lo | 132 | 27.81 | 20.30 | 16.54 | 5.9 | |
| CD8-IM | | | | | | 1.53E−04 |
| Hi | 129 | 60.93 | 50.78 | 45.31 | 49.2 | |
| Lo | 185 | 40.64 | 29.41 | 24.59 | 16.6 | |
| CD3-CT | | | | | | 3.90E−08 |
| Hi | 192 | 60.41 | 48.95 | 43.75 | 45.9 | |
| Lo | 165 | 28.91 | 19.87 | 16.26 | 5.9 | |
| CD3-IM | | | | | | 3.37E−08 |
| Hi | 178 | 59.77 | 49.72 | 44.69 | 47.8 | |
| Lo | 175 | 35.42 | 24.57 | 20.00 | 12.9 | |
| GZM-CT/IM | | | | | | 3.67E−07 |
| HiHi | 95 | 62.74 | 51.96 | 46.07 | 51.4 | |
| LoLo | 80 | 39.43 | 29.57 | 25.35 | 12.9 | |

TABLE 5-continued

Disease Free Survival (DFS)

| | N. of patients | Rate at 2 yr % | Rate at 4 yr % | Rate at 5 yr % | Median months | P value |
|---|---|---|---|---|---|---|
| CD45RO-CT/IM | | | | | | 4.57E−10 |
| HiHi | 151 | 60.26 | 52.31 | 47.68 | 51.6 | |
| LoLo | 41 | 16.66 | 11.90 | 9.52 | 1.8 | |
| CD8-CT/IM | | | | | | 4.61E−08 |
| HiHi | 96 | 65.62 | 55.20 | 50.00 | 59.2 | |
| LoLo | 93 | 30.85 | 21.27 | 17.02 | 5.9 | |
| CD3-CT/IM | | | | | | 5.20E−11 |
| HiHi | 109 | 69.72 | 61.46 | 55.04 | 66.2 | |
| LoLo | 93 | 27.95 | 19.35 | 13.97 | 5.9 | |

TABLE 6

Overall Survival (OS)

| | N. of patients | Rate at 2 yr % | Rate at 4 yr % | Rate at 5 yr % | Median months | P Value |
|---|---|---|---|---|---|---|
| GZM-CT | | | | | | 8.18E−07 |
| Hi | 163 | 62.58 | 50.31 | 43.56 | 50.2 | |
| Lo | 191 | 48.17 | 32.46 | 25.13 | 21.2 | |
| GZM-IM | | | | | | 1.27E−02 |
| Hi | 175 | 61.14 | 48.57 | 39.43 | 45.3 | |
| Lo | 129 | 55.04 | 37.21 | 29.46 | 29.1 | |
| CD45RO-CT | | | | | | 3.14E−09 |
| Hi | 294 | 57.82 | 45.92 | 38.78 | 34.9 | |
| Lo | 67 | 37.31 | 16.42 | 11.94 | 16.4 | |
| CD45RO-IM | | | | | | 7.68E−04 |
| Hi | 190 | 62.63 | 50.53 | 44.21 | 49.2 | |
| Lo | 178 | 46.63 | 30.90 | 23.03 | 19.8 | |
| CD8-CT | | | | | | 2.66E−07 |
| Hi | 227 | 59.47 | 48.02 | 40.53 | 42.5 | |
| Lo | 132 | 43.94 | 25.76 | 19.70 | 18.7 | |
| CD8-IM | | | | | | 1.22E−03 |
| Hi | 129 | 65.63 | 53.91 | 46.88 | 54.8 | |
| Lo | 185 | 54.84 | 37.10 | 28.50 | 29.6 | |
| CD3-CT | | | | | | 7.86E−08 |
| Hi | 192 | 65.63 | 55.21 | 47.40 | 57.8 | |
| Lo | 165 | 42.42 | 24.24 | 18.18 | 18.6 | |
| CD3-IM | | | | | | 9.08E−05 |
| Hi | 178 | 64.04 | 52.25 | 46.07 | 52.6 | |
| Lo | 175 | 48.57 | 32.57 | 24.00 | 21.4 | |
| GZM-CT/IM | | | | | | 1.50E−03 |
| HiHi | 95 | 68.42 | 55.79 | 47.37 | 58.3 | |
| LoLo | 80 | 58.75 | 37.50 | 28.75 | 32.0 | |
| CD45RO-CT/IM | | | | | | 4.12E−07 |
| HiHi | 151 | 64.24 | 54.97 | 49.67 | 59.6 | |
| LoLo | 41 | 39.02 | 14.63 | 12.20 | 17.7 | |
| CD8-CT/IM | | | | | | 1.21E−06 |
| HiHi | 96 | 69.79 | 59.38 | 52.08 | 61.2 | |
| LoLo | 93 | 49.46 | 29.03 | 21.51 | 22.3 | |
| CD3-CT/IM | | | | | | 5.07E−08 |
| HiHi | 109 | 72.48 | 64.22 | 55.96 | 63.9 | |
| LoLo | 93 | 45.16 | 25.81 | 16.13 | 19.3 | |

TABLE 7

Multivariate proportional hazard analysis for DFS

| Variable* | Hazard ratio | 95% CI | P |
|---|---|---|---|
| T-stage | 1.780 | (1.348-2.362) | 5.2E−05 |
| N-stage | 2.130 | (1.481-3.060) | 4.5E−05 |
| Differentiation | 1.110 | (0.777-1.584) | 5.7E−01 |
| $CD3_{CT}/CD3_{IM}$ patterns | 0.570 | (0.450-0.721) | 2.8E−06 |
| T-stage | 1.700 | (1.275-2.268) | 3.1E−05 |
| N-stage | 2.117 | (1.449-3.093) | 1.1E−04 |
| Differentiation | 0.969 | (0.676-1.389) | 8.6E−01 |
| $CD8_{CT}/CD8_{IM}$ patterns | 0.614 | (0.480-0.786) | 1.1E−04 |

TABLE 7-continued

| | | | |
|---|---|---|---|
| T-stage | 1.880 | (1.441-2.452) | 3.3E−06 |
| N-stage | 2.298 | (1.599-3.301) | 6.8E−06 |
| Differentiation | 1.035 | (0.736-1.457) | 8.4E−01 |
| $CD45RO_{CT}/CD45RO_{IM}$ patterns | 0.564 | (0.439-0.723) | 6.2E−06 |
| T-stage | 1.777 | (1.334-2.37) | 8.5E−05 |
| N-stage | 2.449 | (1.651-3.63) | 8.3E−06 |
| Differentiation | 1.049 | (0.707-1.56) | 8.1E−01 |
| $GZMB_{CT}/GZMB_{IM}$ patterns | 0.591 | (0.459-0.76) | 4.3E−05 |

Multivariate proportional hazard analysis for OS

| Variable | Hazard ratio | 95% CI | P |
|---|---|---|---|
| T-stage | 1.335 | (1.052-1.693) | 1.7E−02 |
| N-stage | 1.657 | (2.989-6.595) | 3.6E−03 |
| M-stage | 4.440 | (1.179-2.328) | 1.5E−13 |
| Differentiation | 1.058 | (0.748-1.496) | 7.5E−01 |
| $CD3_{CT}/CD3_{IM}$ patterns | 0.726 | (0.587-0.897) | 3.0E−03 |
| T-stage | 1.376 | (1.070-1.769) | 1.3E−02 |
| N-stage | 1.575 | (1.100-2.254) | 1.3E−02 |
| M-stage | 4.467 | (2.966-6.729) | 8.0E−13 |
| Differentiation | 0.966 | (0.679-1.375) | 8.5E−01 |
| $CD8_{CT}/CD8_{IM}$ patterns | 0.712 | (0.571-0.888) | 2.5E−03 |
| T-stage | 1.396 | (1.114-1.750) | 3.7E−03 |
| N-stage | 1.684 | (1.204-2.355) | 2.3E−03 |
| M-stage | 4.160 | (2.805-6.170) | 1.4E−12 |
| Differentiation | 0.935 | (0.677-1.292) | 6.9E−01 |
| $CD45RO_{CT}/CD45RO_{IM}$ patterns | 0.703 | (0.558-0.885) | 2.8E−03 |
| T-stage | 1.360 | (1.071-1.73) | 1.2E−02 |
| N-stage | 1.710 | (1.188-2.46) | 3.9E−03 |
| M-stage | 4.392 | (2.866-6.73) | 1.1E−11 |
| Differentiation | 1.094 | (0.752-1.59) | 6.4E−01 |
| $GZMB_{CT}/GZMB_{IM}$ patterns | 0.905 | (0.722-1.14) | 3.9E−01 |

*M stratified

TABLE 8

| Gene Combinations | Status1 | Status2 | Percentage Relapse | Nr, No Relapse | Nr, Relapse | LogRank p-value | LOLO vs Combination | HiHi vs Combination |
|---|---|---|---|---|---|---|---|---|
| IRF1 GNLY | 1 | 1 | 25 | 27 | 9 | 0.00000637 | 1.26E−04 | 1 |
| IRF1 GNLY | 0 | 0 | 71.42857143 | 10 | 25 | 0.00000637 | 1 | 1.26E−04 |
| PDCD1LG1 GNLY | 1 | 1 | 32.43243243 | 25 | 12 | 0.00001957 | 3.89E−04 | 1 |
| PDCD1LG1 GNLY | 0 | 0 | 75 | 9 | 27 | 0.00001957 | 1 | 3.89E−04 |
| PDCD1LG2 IRF1 | 1 | 1 | 25.71428571 | 26 | 9 | 0.00003780 | 2.71E−04 | 1 |
| PDCD1LG2 IRF1 | 0 | 0 | 70.58823529 | 10 | 24 | 0.00003780 | 1 | 2.71E−04 |
| PDCD1LG1 IRF1 | 1 | 1 | 30.23255814 | 30 | 13 | 0.00003942 | 4.85E−04 | 1 |
| PDCD1LG1 IRF1 | 0 | 0 | 69.04761905 | 13 | 29 | 0.00003942 | 1 | 4.85E−04 |
| PDCD1LG1 GNLY | 0 | 1 | 40 | 9 | 6 | 0.00005604 | 0.02553386 | 0.74929474 |
| PDCD1LG1 GNLY | 1 | 0 | 40 | 9 | 6 | 0.00005604 | 0.02553386 | 0.74929474 |
| IRF1 IL8 | 1 | 1 | 26.66666667 | 22 | 8 | 0.00008324 | 6.56E−04 | 1 |
| IRF1 IL8 | 0 | 0 | 72.4137931 | 8 | 21 | 0.00008324 | 1 | 6.56E−04 |
| ICOS GNLY | 0 | 1 | 33.33333333 | 12 | 6 | 0.00009669 | 0.00648539 | 1 |
| ICOS GNLY | 1 | 0 | 47.36842105 | 10 | 9 | 0.00009669 | 0.069525 | 0.55885623 |
| ICOS GNLY | 1 | 1 | 35.29411765 | 22 | 12 | 0.00009903 | 0.00148605 | 1 |
| ICOS GNLY | 0 | 0 | 75 | 8 | 24 | 0.00009903 | 1 | 0.00148605 |
| TNFRSF6B IRF1 | 1 | 1 | 27.27272727 | 24 | 9 | 0.00010448 | 4.71E−04 | 1 |
| TNFRSF6B IRF1 | 0 | 0 | 71.875 | 9 | 23 | 0.00010448 | 1 | 4.71E−04 |
| PDCD1LG2 GNLY | 1 | 1 | 28.57142857 | 25 | 10 | 0.00010559 | 7.00E−04 | 1 |
| PDCD1LG2 GNLY | 0 | 0 | 70.58823529 | 10 | 24 | 0.00010559 | 1 | 7.00E−04 |
| IRTA2 GNLY | 1 | 1 | 26.92307692 | 19 | 7 | 0.00010819 | 7.02E−04 | 1 |
| IRTA2 GNLY | 0 | 0 | 76 | 6 | 19 | 0.00010819 | 1 | 7.02E−04 |
| IRF1 GNLY | 1 | 0 | 50 | 8 | 8 | 0.00013118 | 0.20696761 | 0.11061678 |
| IRF1 GNLY | 0 | 1 | 56.25 | 7 | 9 | 0.00013118 | 0.34514115 | 0.05584765 |
| STAT1 PDCD1LG1 | 1 | 1 | 31.03448276 | 20 | 9 | 0.00015364 | 0.00411737 | 1 |
| STAT1 PDCD1LG1 | 0 | 0 | 70 | 9 | 21 | 0.00015364 | 1 | 0.00411737 |
| STAT1 IRF1 | 1 | 1 | 25 | 21 | 7 | 0.00017203 | 0.00136119 | 1 |
| STAT1 IRF1 | 0 | 0 | 68.96551724 | 9 | 20 | 0.00017203 | 1 | 0.00136119 |
| GATA3 CD8A | 0 | 1 | 69.23076923 | 4 | 9 | 0.00018062 | 0.3355095 | 0.02232563 |
| GATA3 CD8A | 1 | 0 | 84.61538462 | 2 | 11 | 0.00018062 | 0.04841363 | 0.00103488 |
| GNLY CXCL9 | 1 | 1 | 31.42857143 | 24 | 11 | 0.00018108 | 0.00167576 | 1 |
| GNLY CXCL9 | 0 | 0 | 70.58823529 | 10 | 24 | 0.00018108 | 1 | 0.00167576 |
| TBX21 GNLY | 1 | 1 | 30.3030303 | 23 | 10 | 0.00021196 | 4.58E−04 | 1 |
| TBX21 GNLY | 0 | 0 | 75 | 8 | 24 | 0.00021196 | 1 | 4.58E−04 |
| TNFRSF6B PDCD1LG1 | 1 | 1 | 31.25 | 22 | 10 | 0.00021333 | 9.67E−04 | 1 |
| TNFRSF6B PDCD1LG1 | 0 | 0 | 74.19354839 | 8 | 23 | 0.00021333 | 1 | 9.67E−04 |
| IRF1 ICOS | 1 | 1 | 27.77777778 | 26 | 10 | 0.00021448 | 0.00164508 | 1 |
| IRF1 ICOS | 0 | 0 | 67.64705882 | 11 | 23 | 0.00021448 | 1 | 0.00164508 |
| IL8 CD4 | 1 | 0 | 33.33333333 | 18 | 9 | 0.00021968 | 3.65E−04 | 0.39718035 |
| IL8 CD4 | 0 | 1 | 37.93103448 | 18 | 11 | 0.00021968 | 5.91E−04 | 0.58270625 |
| TBX21 IRF1 | 1 | 1 | 25 | 27 | 9 | 0.00022445 | 3.28E−04 | 1 |
| TBX21 IRF1 | 0 | 0 | 68.57142857 | 11 | 24 | 0.00022445 | 1 | 3.28E−04 |
| PDCD1LG2 IRF1 | 0 | 1 | 47.05882353 | 9 | 8 | 0.00022793 | 0.13051259 | 0.20662362 |
| PDCD1LG2 IRF1 | 1 | 0 | 58.82352941 | 7 | 10 | 0.00022793 | 0.53057151 | 0.03154075 |
| GNLY CD4 | 1 | 0 | 22.22222222 | 14 | 4 | 0.00023630 | 2.62E−04 | 0.22728471 |
| GPNLY CD4 | 0 | 1 | 45 | 11 | 9 | 0.00023630 | 0.03419617 | 1 |
| MMP7 IRF1 | 1 | 1 | 25 | 21 | 7 | 0.00025303 | 4.06E−04 | 1 |
| MMP7 IRF1 | 0 | 0 | 74.07407407 | 7 | 20 | 0.00025303 | 1 | 4.06E−04 |
| TNF PDCD1LG1 | 0 | 1 | 29.41176471 | 12 | 5 | 0.00027386 | 0.00205134 | 0.75798695 |
| TNF PDCD1LG1 | 1 | 0 | 41.17647059 | 10 | 7 | 0.00027386 | 0.02760881 | 1 |
| TNFRSF6B GNLY | 1 | 1 | 30.3030303 | 23 | 10 | 0.00027678 | 0.00119011 | 1 |
| TNFRSF6B GNLY | 0 | 0 | 71.875 | 9 | 23 | 0.00027678 | 1 | 0.00119011 |
| TGFB1 IRF1 | 1 | 1 | 29.03225806 | 22 | 9 | 0.00028329 | 8.07E−04 | 1 |
| TGFB1 IRF1 | 0 | 0 | 73.33333333 | 8 | 22 | 0.00028329 | 1 | 8.07E−04 |

TABLE 8-continued

| Gene Combinations | Status1 | Status2 | Percentage Relapse | Nr, No Relapse | Nr, Relapse | LogRank p-value | LOLO vs Combination | HiHi vs Combination |
|---|---|---|---|---|---|---|---|---|
| PDCD1LG2 PDCD1LG1 | 1 | 1 | 31.70731707 | 28 | 13 | 0.00031033 | 0.00180905 | 1 |
| PDCD1LG2 PDCD1LG1 | 0 | 0 | 67.5 | 13 | 27 | 0.00031033 | 1 | 0.00180905 |
| TGFB1 IRF1 | 0 | 1 | 38.0952381 | 13 | 8 | 0.00031619 | 0.02015558 | 0.5556315 |
| TGFB1 IRF1 | 1 | 0 | 57.14285714 | 9 | 12 | 0.00031619 | 0.24654453 | 0.05090421 |
| TBX21 PDCD1LG1 | 1 | 1 | 27.77777778 | 26 | 10 | 0.00033814 | 8.35E-04 | 1 |
| TBX21 PDCD1LG1 | 0 | 0 | 68.57142857 | 11 | 24 | 0.00033814 | 1 | 8.35E-04 |
| TNF GNLY | 1 | 1 | 34.48275862 | 19 | 10 | 0.00033997 | 4.10E-04 | 1 |
| TNF GNLY | 0 | 0 | 82.14285714 | 5 | 23 | 0.00033997 | 1 | 4.10E-04 |
| PDCD1LG1 IRF1 | 0 | 1 | 44.44444444 | 5 | 4 | 0.00035285 | 0.24937129 | 0.45141556 |
| PDCD1LG1 IRF1 | 1 | 0 | 55.55555556 | 4 | 5 | 0.00035285 | 0.45891075 | 0.24655356 |
| IRF1 CXCL9 | 1 | 1 | 30 | 28 | 12 | 0.00036339 | 0.00157043 | 1 |
| IRF1 CXCL9 | 0 | 0 | 66.66666667 | 13 | 26 | 0.00036339 | 1 | 0.00157043 |
| TBX21 GNLY | 0 | 1 | 42.10526316 | 11 | 8 | 0.00037639 | 0.03467136 | 0.54586516 |
| TBX21 GNLY | 1 | 0 | 47.36842105 | 10 | 9 | 0.00037639 | 0.069525 | 0.24596116 |
| PTGS2 IRF1 | 1 | 1 | 30.76923077 | 18 | 8 | 0.00038160 | 0.00500586 | 1 |
| PTGS2 IRF1 | 0 | 0 | 72 | 7 | 18 | 0.00038160 | 1 | 0.00500586 |
| IRF1 ART1 | 1 | 0 | 20 | 8 | 2 | 0.00038775 | 0.01498501 | 0.6043956 |
| IRF1 ART1 | 0 | 1 | 66.66666667 | 3 | 6 | 0.00038775 | 0.4965035 | 0.31468531 |
| INDO GNLY | 1 | 1 | 35.29411765 | 22 | 12 | 0.00039262 | 0.00707271 | 1 |
| INDO GNLY | 0 | 0 | 69.6969697 | 10 | 23 | 0.00039262 | 1 | 0.00707271 |
| PDCD1LG1 ICOS | 1 | 1 | 31.57894737 | 26 | 12 | 0.00039662 | 0.00489333 | 1 |
| PDCD1LG1 ICOS | 0 | 0 | 66.66666667 | 12 | 24 | 0.00039662 | 1 | 0.00489333 |
| PDCD1LG2 GNLY | 0 | 1 | 47.05882353 | 9 | 8 | 0.00039685 | 0.13051259 | 0.22435124 |
| PDCD1LG2 GNLY | 1 | 0 | 52.94117647 | 8 | 9 | 0.00039685 | 0.23279471 | 0.12613911 |
| TNFRSF6B TBX21 | 1 | 1 | 24 | 19 | 6 | 0.00041496 | 5.44E-04 | 1 |
| TNFRSF6B TBX21 | 0 | 0 | 75 | 6 | 18 | 0.00041496 | 1 | 5.44E-04 |
| PDCD1 IRF1 | 1 | 1 | 25.64102564 | 29 | 10 | 0.00043410 | 5.64E-04 | 1 |
| PDCD1 IRF1 | 0 | 0 | 65.78947368 | 13 | 25 | 0.00043410 | 1 | 5.64E-04 |
| IRF1 IFNG | 1 | 1 | 27.02702703 | 27 | 10 | 0.00043964 | 7.09E-04 | 1 |
| IRF1 IFNG | 0 | 0 | 68.75 | 10 | 22 | 0.00043964 | 1 | 7.09E-04 |
| TNF GNLY | 0 | 1 | 34.7826087 | 15 | 8 | 0.00044402 | 0.00122608 | 1 |
| TNF GNLY | 1 | 0 | 43.47826087 | 13 | 10 | 0.00044402 | 0.00736128 | 0.57364958 |
| IL8 GNLY | 1 | 1 | 31.03448276 | 20 | 9 | 0.00046499 | 0.00136119 | 1 |
| IL8 GNLY | 0 | 0 | 75 | 7 | 21 | 0.00046499 | 1 | 0.00136119 |
| TNFRSF6B IFNG | 1 | 1 | 25 | 21 | 7 | 0.00046651 | 9.10E-04 | 1 |
| TNFRSF6B IFNG | 0 | 0 | 72 | 7 | 18 | 0.00046651 | 1 | 9.10E-04 |
| PDCD1LG1 PDCD1 | 1 | 1 | 27.02702703 | 27 | 10 | 0.00047832 | 9.77E-04 | 1 |
| PDCD1LG1 PDCD1 | 0 | 0 | 66.66666667 | 12 | 24 | 0.00047832 | 1 | 9.77E-04 |
| IRTA2 GNLY | 0 | 1 | 42.30759231 | 15 | 11 | 0.00048486 | 0.0227009 | 0.3822679 |
| IRTA2 GNLY | 1 | 0 | 56 | 11 | 14 | 0.00048486 | 0.23209547 | 0.04831826 |
| PDCD1LG1 CXCL9 | 1 | 1 | 34.14634146 | 27 | 14 | 0.00050191 | 0.0038056 | 1 |
| PDCD1LG1 CXCL9 | 0 | 0 | 67.5 | 13 | 27 | 0.00050191 | 1 | 0.0038056 |
| IL8 ICOS | 1 | 1 | 39.28571429 | 17 | 11 | 0.00050590 | 0.00668911 | 1 |
| IL8 ICOS | 0 | 0 | 76.92307692 | 6 | 20 | 0.00050590 | 1 | 0.00668911 |
| TNF IRF1 | 1 | 1 | 31.42857143 | 24 | 11 | 0.00054072 | 6.84E-04 | 1 |
| TNF IRF1 | 0 | 0 | 73.52941176 | 9 | 25 | 0.00054072 | 1 | 6.84E-04 |
| IL8 ICOS | 0 | 1 | 40 | 15 | 10 | 0.00055140 | 0.01074613 | 1 |
| IL8 ICOS | 1 | 0 | 41.66666667 | 14 | 10 | 0.00055140 | 0.01996838 | 1 |
| IRF1 IL8 | 1 | 0 | 40.90909091 | 13 | 9 | 0.00057567 | 0.04324338 | 0.37231571 |
| IRF1 IL8 | 0 | 1 | 59.09090909 | 9 | 13 | 0.00057567 | 0.37716737 | 0.02446738 |
| PDCD1 GNLY | 1 | 1 | 31.42857143 | 24 | 11 | 0.00058024 | 6.84E-04 | 1 |
| PDCD1 GNLY | 0 | 0 | 73.52941176 | 9 | 25 | 0.00058024 | 1 | 6.84E-04 |
| TNFRSF6B CXCL9 | 1 | 1 | 32.14285714 | 19 | 9 | 0.00063900 | 0.00694187 | 1 |
| TNFRSF6B CXCL9 | 0 | 0 | 71.42857143 | 8 | 20 | 0.00063900 | 1 | 0.00694187 |
| GNLY CXCL10 | 1 | 1 | 34.28571429 | 23 | 12 | 0.00064897 | 0.00374119 | 1 |
| GNLY CXCL10 | 0 | 0 | 70.58823529 | 10 | 24 | 0.00064897 | 1 | 0.00374119 |
| SELL GNLY | 1 | 1 | 32.14285714 | 19 | 9 | 0.00065255 | 0.00105233 | 1 |
| SELL GNLY | 0 | 0 | 77.77777778 | 6 | 21 | 0.00065255 | 1 | 0.00105233 |
| SELL IRF1 | 1 | 1 | 26.66666667 | 22 | 8 | 0.00065555 | 6.56E-04 | 1 |
| SELL IRF1 | 0 | 0 | 72.4137931 | 8 | 21 | 0.00065555 | 1 | 6.56E-04 |
| MMP7 GNLY | 1 | 1 | 31.03448276 | 20 | 9 | 0.00067878 | 0.00136119 | 1 |
| MMP7 GNLY | 0 | 0 | 75 | 7 | 21 | 0.00067878 | 1 | 0.00136119 |
| PDCD1LG1 EBAG9 | 1 | 1 | 37.93103448 | 18 | 11 | 0.00067896 | 0.03430795 | 1 |
| PDCD1LG1 EBAG9 | 0 | 0 | 68.96551724 | 9 | 20 | 0.00067896 | 1 | 0.03430795 |
| TGFB1 GNLY | 1 | 1 | 29.03225806 | 22 | 9 | 0.00071504 | 0.00204606 | 1 |
| TGFB1 GNLY | 0 | 0 | 70 | 9 | 21 | 0.00071504 | 1 | 0.00204606 |
| IL18R1 GNLY | 1 | 1 | 36.36363636 | 21 | 12 | 0.00075372 | 0.01304077 | 1 |
| IL18R1 GNLY | 0 | 0 | 68.75 | 10 | 22 | 0.00075372 | 1 | 0.01304077 |
| IFNG GNLY | 1 | 1 | 28.57142857 | 25 | 10 | 0.00075584 | 0.00119534 | 1 |
| IFNG GNLY | 0 | 0 | 70 | 9 | 21 | 0.00075584 | 1 | 0.00119534 |
| TNFRSF6B PDCD1LG2 | 1 | 1 | 26.66666667 | 22 | 8 | 0.00076477 | 0.00169422 | 1 |
| TNFRSF6B PDCD1LG2 | 0 | 0 | 68.96551724 | 9 | 20 | 0.00076477 | 1 | 0.00169422 |
| TNFRSF6B PDCD1 | 1 | 1 | 29.62962963 | 19 | 8 | 0.00081540 | 8.73E-04 | 1 |
| TNFRSF6B PDCD1 | 0 | 0 | 76.92307692 | 6 | 20 | 0.00081540 | 1 | 8.73E-04 |
| INDO GNLY | 0 | 1 | 33.33333333 | 12 | 6 | 0.00081585 | 0.01830705 | 1 |
| INDO GNLY | 1 | 0 | 55.55555556 | 8 | 10 | 0.00081585 | 0.36715926 | 0.23851535 |
| TBX21 IL8 | 1 | 0 | 39.28571429 | 17 | 11 | 0.00081677 | 0.00372377 | 0.77529553 |

TABLE 8-continued

| Gene Combinations | Status1 | Status2 | Percentage Relapse | Nr, No Relapse | Nr, Relapse | LogRank p-value | LOLO vs Combination | HiHi vs Combination |
|---|---|---|---|---|---|---|---|---|
| TBX21 IL8 | 0 | 1 | 46.42857143 | 15 | 13 | 0.00081677 | 0.00995396 | 0.40283859 |
| TNFRSF8 IRF1 | 1 | 1 | 25.80645161 | 23 | 8 | 0.00082357 | 0.00458134 | 1 |
| TNFRSF8 IRF1 | 0 | 0 | 63.33333333 | 11 | 19 | 0.00082357 | 1 | 0.00458134 |
| TNF PDCD1LG1 | 1 | 1 | 37.14285714 | 22 | 13 | 0.00083836 | 0.00148511 | 1 |
| TNF PDCD1LG1 | 0 | 0 | 76.47058824 | 8 | 26 | 0.00083836 | 1 | 0.00148511 |
| IRF1 EBAG9 | 1 | 1 | 35.71428571 | 18 | 10 | 0.00085969 | 0.01512429 | 1 |
| IRF1 EBAG9 | 0 | 0 | 71.42857143 | 8 | 20 | 0.00085969 | 1 | 0.01512429 |
| PDCD1LG1 IL18R1 | 1 | 1 | 37.14285714 | 22 | 13 | 0.00087042 | 0.01603268 | 1 |
| PDCD1LG1 IL18R1 | 0 | 0 | 67.64705882 | 11 | 23 | 0.00087042 | 1 | 0.01603268 |
| IRTA2 IRF1 | 1 | 1 | 33.33333333 | 22 | 11 | 0.00087051 | 0.00113427 | 1 |
| IRTA2 IRF1 | 0 | 0 | 75 | 8 | 24 | 0.00087051 | 1 | 0.00113427 |
| IRF1 IL18R1 | 1 | 1 | 33.33333333 | 22 | 11 | 0.00087233 | 0.0063032 | 1 |
| IRF1 IL18R1 | 0 | 0 | 68.75 | 10 | 22 | 0.00087233 | 1 | 0.0063032 |
| LAT IL8 | 0 | 1 | 34.48275862 | 19 | 10 | 0.00091759 | 0.00148805 | 0.3996356 |
| LAT IL8 | 1 | 0 | 41.37931034 | 17 | 12 | 0.00091759 | 0.00461551 | 0.77997357 |
| SELL GNLY | 0 | 1 | 37.5 | 15 | 9 | 0.00095410 | 0.00482852 | 0.77381721 |
| SELL GNLY | 1 | 0 | 50 | 12 | 12 | 0.00095410 | 0.04632871 | 0.25940735 |

TABLE 9

| gene name (old) | alternate name | gene pathway | gene description | Public RefSeq |
|---|---|---|---|---|
| 18s | | endogenous control | endogenous control | X03205 |
| ACE | ACE | Tumor | DCP, ACE1, DCP1, CD143, MGC26566 | NM_000789 |
| ACTB | Beta Actin | endogenous control | endogenous control | NM_003234 |
| AGTR1 | angiotensin II receptor, type 1 | angiogenesis | AT1, AG2S, AT1B, AT2R1, HAT1R, AGTR1A, AGTR1B, AT2R1A, AT2R1B | NM_031850.1, NM_000685.3 |
| AGTR2 | angiotensin II receptor, type 2 | angiogenesis | AT2 | NM_000686 |
| APC | | | | NM_000038 |
| APOA1 | apolipoprotein A-I | MHC pathway | present sur cell tum et module cytotox, interaction TCRg9d2 | NM_000039 |
| ARF1 | p53 signalling | tumor suppressor | | NM_001658 |
| AXIN1 | Axin | Axin | | NM_181050| NM_003502 |
| BAX | BAX | Apoptosis pathway | | NM_138763, NM_138765, NM_004324, NM_138761 |
| BCL2 | BCL2 | Apoptosis pathway | | NM_000633 |
| BCL2L1 | BCL-XL | Apoptosis pathway | | NM_001191 |
| CXCR5 | | chemokine pathway | | NM_001716 |
| BMP2 | BMP2 | TGF pathway | Bone morphogenetic protein 8a | NM_001200 |
| BRCA1 | | | | NM_007294| NM_007295| NM_007296| NM_007297| NM_007298| NM_007299| NM_007300| NM_007301| NM_007302| NM_007303| NM_007304| |

TABLE 9-continued

| gene name (old) | alternate name | gene pathway | gene description | Public RefSeq |
|---|---|---|---|---|
| BTLA | BTLA | Adaptive immunity | B and T lymphocyte associated | NM_007305\| NM_007306 NM_181780 |
| C3 | C3 | C3 | | NM_000064 |
| CASP3 | apoptosis | apoptosis | | NM_004346 |
| CASP9 | caspase 9, apoptosis-related cysteine peptidase, Gene hCG25367 Celera Annotation | | | NM_001229.2 |
| CCL1 | CCL1 | chemokine pathway | Chemokine (C-C motif) ligand 1 | NM_002981 |
| CCL11 | Eotaxin | chemokine pathway | Chemokine (C-C motif) ligand 11 | NM_002986 |
| CCL13 | MCP-4 | chemokine pathway | Chemokine (C-C motif) ligand 13 | NM_005408 |
| CCL16 | HCC-4 | chemokine pathway | CC Chemokines & Receptors | NM_004590 |
| CCL17 | TARC | chemokine pathway | Chemokine (C-C motif) ligand 17 | NM_002987 |
| CCL18 | PARC | chemokine pathway | CC Chemokines & Receptors | NM_002988 |
| CCL19 | Mip-3c, MIP-3 beta | chemokine pathway | SCYA19 | NM_006274 |
| CCL2 | MCP-1 | chemokine pathway | SCYA2 | NM_002982 |
| CCL20 | MIP-3 alpha | chemokine pathway | Chemokine (C-C motif) ligand 20 | NM_004591 |
| CCL21 | 6Ckine | chemokine pathway | chemokine (C-C motif) ligand 21 | NM_002989 |
| CCL22 | CCR4 ligand, MDC, T-reg spec | chemokine pathway | chemokine (C-C motif) ligand 22 | NM_002990 |
| CCL23 | MPIF-1 | chemokine pathway | chemokine (C-C motif) ligand 23 | NM_145898\| NM_005064 |
| CCL24 | Eotaxin-2 | chemokine pathway | chemokine (C-C motif) ligand 24 | NM_002991 |
| CCL25 | TECK | chemokine pathway | chemokine (C-C motif) ligand 25 | NM_148888\| NM_005624 |
| CCL26 | Eotaxin-3 | chemokine pathway | chemokine (C-C motif) ligand 26 | NM_006072 |
| CCL27 | CTACK | chemokine pathway | chemokine (C-C motif) ligand 27 | NM_006664 |
| CCL28 | CCL28 | chemokine pathway | chemokine (C-C motif) ligand 28 | NM_019846\| NM_148672 |
| CCL3 | Mip-1a | chemokine pathway | SCYA3 | NM_002983 |
| CCL5 | Rantes | chemokine pathway | SCYA5 | NM_002985 |
| CCL7 | MCP-3 | chemokine pathway | chemokine (C-C motif) ligand 7 | NM_006273 |
| CCL8 | MCP-2 | chemokine pathway | chemokine (C-C motif) ligand 8 | NM_005623 |
| CCNB1 | | cell cycle | | NM_031966 |
| CCND1 | | cell cycle | | NM_053056 |
| CCNE1 | | cell cycle | | NM_001238\| NM_057182 |
| CCR1 | | chemokine pathway | CC Chemokines & Receptors | NM_001295 |

TABLE 9-continued

| gene name (old) | alternate name | gene pathway | gene description | Public RefSeq |
|---|---|---|---|---|
| CCR10 | CCR10 | chemokine pathway | chemokine (C-C motif) receptor 10 | NM_016602 |
| CCR2 | CCR2 | chemokine pathway | | NM_000647 |
| CCR3 | CCR3 | chemokine pathway | chemokine (C-C motif) receptor 3 | NM_178329\| NM_001837 |
| CCR4 | CCR4 | chemokine pathway | chemokine (C-C motif) receptor 4 | NM_005508 |
| CCR5 | CCR5 | chemokine pathway | | NM_000579 |
| CCR6 | CCR6 | chemokine pathway | chemokine (C-C motif) receptor 6 | NM_031409\| NM_004367 |
| CCR7 | CCR7 | chemokine pathway | | NM_001838 |
| CCR8 | CCR8 | chemokine pathway | chemokine (C-C motif) receptor 8 | NM_005201 |
| CCR9 | CCR9 | chemokine pathway | chemokine (C-C motif) receptor 9 | NM_006641 |
| CCRL2 | HCR | chemokine pathway | CC Chemokines & Receptors | |
| CD154 | CD154 (TNFSF5) | Adaptive immunity | | NM_000074 |
| CD19 | B cells | Adaptive immunity | | NM_001770 |
| CD1a | CD1A | Adaptive immunity | CD1A antigen, a polypeptide | NM_001763 |
| CD2 | CD2 antigen (p50), sheep red blood cell receptor | Adaptive immunity | | NM_001767 |
| CD226 | PTA1; DNAM1; DNAM-1; TLiSA1 Summary: CD226 is a ~65 kDa glycoprotein expressed on the surface of NK cells, platelets, monocytes and a subset of T cells. It is a member of the Ig-superfamily containing 2 Ig-like domains of the V-set and is encoded by a gene on human chromosome 18q22.3. CD226 mediates cellular adhesion to other cells bearing an unidentified ligand and cross-linking CD226 with antibodies causes cellular activation | adhesion, activation | | NM_006566 |
| CD244 | CD244 natural killer cell receptor 2B4 | | | NM_016382 |
| PDCD1LG1 | B7H1 | Adaptive immunity | | NM_014143 |
| CD28 | CD28 | Adaptive immunity | | NM_006139 |

TABLE 9-continued

| gene name (old) | alternate name | gene pathway | gene description | Public RefSeq |
|---|---|---|---|---|
| CD34 | CD34 | CD34 | | NM_001773 |
| CD36 | CD36 antigen (collagen type I receptor, thrombospondin receptor) | | | NM_001001547\| NM_001001548\| NM_000072 |
| CD38 | CD38 | Adaptive immunity | | NM_001775 |
| CD3E | CD3E antigen, epsilon polypeptide (TiT3 complex) | Adaptive immunity | | NM_000733 |
| CD3G | CD3G antigen, gamma polypeptide (TiT3 complex) | Adaptive immunity | | NM_000073 |
| CD3Z | CD3Z antigen, zeta polypeptide (TiT3 complex) | Adaptive immunity | | NM_000734 |
| CD4 | CD4 antigen (p55) | Adaptive immunity | | NM_000616 |
| CD40LG | TNFSF5 | Adaptive immunity | CD40L | NM_000074 |
| CD5 | | Adaptive immunity | | NM_014207 |
| CD54 | ICAM-1 | Adaptive immunity | | NM_000201 |
| CD6 | | Adaptive immunity | | NM_006725 |
| CD68 | CD68 | Innate immunity | | NM_001251 |
| CD69 | | Adaptive immunity | | NM_001781 |
| CLIP | CD74 antigen (invariant polypeptide of major histocompatibility complex, class II antigen-associated) | MHC pathway | | NM_001025158\| NM_001025159\| NM_004355 |
| CD80 | CD80 | Adaptive immunity | | NM_005191 |
| CD83 | | Adaptive immunity | | NM_004233 |
| SLAMF5 | CD84 | Adaptive immunity | | NM_003874 |
| CD86 | CD86 | Adaptive immunity | | NM_006889 |
| CD8A | CD8 | Adaptive immunity | | NM_001768.1 |
| CDH1 | cadherin 1, type 1, E-cadherin (epithelial) | adhesion, metastasis | Embols | NM_004360 |
| CDH7 | Adhesion | adhesion | | NM_004361 |
| CDK2 | | cell cycle | | NM_052827\| NM_001798 |
| CDK4 | | cell cycle | | NM_000075 |
| CDKN1A | CIP1 p21 | mutation and methylation | cyclin-dependent kinase inhibitor 1A (p21, Cip1) | |
| DKN1B | KIP1 p27 | mutation and methylation | cyclin-dependent kinase inhibitor 1B (p27, Kip1) | NM_004064 |
| CDKN2A | p16INK4a | mutation and methylation | cyclin-dependent kinase inhibitor 2A (melanoma, p16, inhibits CDK4) | NM_000077; NM_058195; NM_058197; |
| CDKN2B | CDKN2B | | cyclin-dependent kinase inhibitor 2B (p15, inhibits CDK4) | NM_004936 |

TABLE 9-continued

| gene name (old) | alternate name | gene pathway | gene description | Public RefSeq |
|---|---|---|---|---|
| CEACAM1 | (CD66a) | Tumor | | NM_001024912\| NM_001712 |
| COL4A5 | Collagen IV (COL4A5) | Collagen IV (COL4A5) | | NM_033381.1, NM_033380.1, NM_000495.3 |
| CREBBP | | CK pathway | Histone acetyltransferase | NM_004380 |
| CRLF2 | TSLP R | Adaptive immunity | | NM_022148\| NM_001012288 |
| CSF1 | colony stimulating factor 1 (macrophage) | | CSF-1 | NM_000757 |
| CSF2 | CSF-2 | | CSF-2 | NM_000758 |
| CSF3 | CSF-3 | | CSF-3 | NM_000759 |
| CTLA4 | CD152 | Adaptive immunity | CD152 | NM_005214 |
| CTNNB1 | beta-catenin wnt pathway catenin (cadherin-associated protein), beta 1, 88 kDa | wnt pathway | catenin (cadherin-associated protein), beta 1, 88 kDa | NM_001904 |
| CTSC | | Adaptive immunity | DNA microarray T | NM_148170.2\| NM_001814.2 |
| CX3CL1 | Fractalkine | chemokine pathway | chemokine (C—X3—C motif) ligand 1 | NM_002996 |
| CX3CR1 | CX3CR1 | chemokine pathway | chemokine (C—X3—C motif) receptor 1 | NM_001337 |
| CXCL1 | GRO alpha | chemokine pathway | chemokine (C—X—C motif) ligand 1 (melanoma growth stimulating activity, alpha) | NM_001511 |
| CXCL10 | IP10 | chemokine pathway | SCYB11 | NM_001565 |
| CXCL11 | ITAC | chemokine pathway | SCYB11 | NM_005409 |
| CXCL12 | SDF-1 | chemokine pathway | chemokine (C—X—C motif) ligand 12 (stromal cell-derived factor 1) | NM_199168\| NM_000609 |
| CXCL13 | BLC | chemokine pathway | chemokine (C—X—C motif) ligand 13 (B-cell chemoattractant) | NM_006419 |
| CXCL14 | BRAK | chemokine pathway | CXC Chemokines & Receptors | NM_004887 |
| CXCL16 | CXCR6 ligand, Th1 | chemokine pathway | chemokine (C—X—C motif) ligand 16 | NM_022059 |
| CXCL2 | GRO beta | chemokine pathway | chemokine (C—X—C motif) ligand 2 | NM_002089 |
| CXCL3 | GRO gamma | chemokine pathway | chemokine (C—X—C motif) ligand 3 | NM_002090 |
| CXCL5 | ENA | chemokine pathway | Chemokine (C—X—C motif) ligand 5 | NM_002994 |
| CXCL6 | GCP-2 | chemokine pathway | chemokine (C—X—C motif) ligand 6 (granulocyte chemotactic protein 2) | NM_002993 |

TABLE 9-continued

| gene name (old) | alternate name | gene pathway | gene description | Public RefSeq |
|---|---|---|---|---|
| CXCL9 | MIG | chemokine pathway | CXC Chemokines & Receptors | NM_002416 |
| CXCR3 | CXCR3 | chemokine pathway | GPR9 | NM_001504 |
| CXCR4 | CXCR4 | chemokine pathway | chemokine (C—X—C motif) receptor 4 | NM_003467 |
| CXCR6 | CXCR6 | chemokine pathway | chemokine (C—X—C motif) receptor 6 | NM_006564 |
| CYP1A2 | CYP1A2 | CYP1A2 | | NM_000761 |
| CYP7A1 | CYP7A1 | CYP7A1 | | NM_000780 |
| DCC | deleted in colorectal carcinoma, Gene hCG1811785 Celera Annotation | metastasis | | NM_005215.1 |
| DCN | DCN | TGF pathway | Decorin Inh TGF | NM_133503\| NM_133504\| NM_133505\| NM_001920 |
| DEFA6 | Defensin alpha 6, over expression in colon K | Defense | over expression in colon K | NM_001926 |
| DICER1 | Dicer1, Dcr-1 homolog (*Drosophila*) | MRNA pathway | | NM_030621; NM_177438 |
| DKK1 | | wnt pathway | dickkopf homolog 1 (*Xenopus laevis*) | NM_012242 |
| Dok-1 | p62Dok | TCR pathway | exprimé parcell hematopoietiques, role inh prolif T | NM_001381 |
| Dok-2 | P56Dok-2, FRIP | TCR pathway | exprimé dans les T, role Inh prolif T | NM_201349\| NM_003974 |
| DOK6 | | | | NM_152721 |
| DVL1 | DHS1 homolog (dishevelled) | DHS1 homolog (dishevelled) | | NM_181870\| NM_182779\| NM_004421 |
| E2F4 | E2F4 | TGF pathway | E2F transcription factor 4, p107/p130-binding | NM_001950 |
| EBI3 | | | | NM_005755 |
| ECE1 | ECE-1 | ECE-1 | ECE | NM_001397 |
| ECGF1 | metastasis | metastasis | | NM_001953 |
| EDN1 | endothelin 1, Gene hCG37405 Celera Annotation | EDN1, hCG37405 | | NM_001955.2 |
| EGF | | | epidermal growth factor (beta-urogastrone) | NM_001963 |
| EGFR | | predicted STRING | epidermal growth factor receptor (erythroblastic leukemia viral (v-erb-b) oncogene homolog, avian) | NM_005228 |

TABLE 9-continued

| gene name (old) | alternate name | gene pathway | gene description | Public RefSeq |
|---|---|---|---|---|
| EIF4E | | | eukaryotic translation initiation factor 4E | |
| CD105 | angiogenese Endoglin | angiogenesis | | NM_000118 |
| ENPEP | glutamyl aminopeptidase (aminopeptidase A), Gene hCG21423 Celera Annotation | ENPEP, hCG21423 | | NM_001977.2 |
| ERBB2 | | | | NM_001005862\| NM_004448 |
| EREG | epiregulin, Gene hCG14966 Celera Annotation | EREG, hCG14966 | | NM_001432.1 |
| FCGR3A, FCGR3B | CD16 | CD16 | | NM_000569, NM_000570 |
| FN1 | Fibronectin (FN precursor) | Fibronectin (FN precursor) | FN, CIG, FINC, LETS | NM_002026.1, NM_054034.1 |
| FOXP3 | FOXP3 | Adaptive immunity | forkhead box P3 | NM_014009 |
| FYN | FYN | TCR pathway | FYN oncogene related to SRC, FGR, YES | NM_153047\| NM_153048\| NM_002037 |
| FZD1 | frizzled | frizzled | frizzled homolog 1 (*Drosophila*) | NM_003505 |
| GAPD | GAPDH | endogenous control | endogenous control | NM_002046 |
| GLI2 | | hedgehog pathway GLI-Kruppel family member GLI2 | GLI-Kruppel family member GLI2 | NM_030379\| NM_030380\| NM_030381\| NM_005270 |
| GNLY | Granulysin (GNLY) | Cytotox pathway | 519, LAG2, NKG5, LAG-2, D2S69E, TLA519 | NM_012483.1, NM_006433.2 |
| GOLPH4 | golgi phosphoprotein 4 | Golgi transporter | required for protein transport from the er to the golgi complex | NM_014498 U55853 |
| GRB2 | | TCR pathway | | NM_203506\| NM_002086 |
| GSK3B | | wnt pathway | glycogen synthase kinase 3 beta | NM_002093 |
| GSTP1 | anti-oxidant | anti-oxidant | | NM_000852 |
| GUSB | GUSB | endogenous control | endogenous control | NM_000181 |
| GZMA | | Adaptive immunity | DNA microarray T | NM_006144.2 |
| GZMB | Granzyme B (GZMB) | Cytotox pathway | CCPI, CSPB, CGL-1, CSP-B, CTLA1 | NM_004131 |
| GZMH | | Adaptive immunity | DNA microarray T | NM_033423.2 |
| GZMK | granzyme K (granzyme 3; tryptase II), Gene hCG40447 Celera Annotation | | DNA microarray T | NM_002104.1 |
| HLA-B | HLA-B | MHC pathway | major histocompatibility complex, class I, B | NM_005514 |
| HLA-C | HLA-C | MHC pathway | major histocompatibility complex, class I, C | NM_002117 |

TABLE 9-continued

| gene name (old) | alternate name | gene pathway | gene description | Public RefSeq |
|---|---|---|---|---|
| HLA-DMA | HLA-DMA | MHC pathway | major histocompatibility complex, class II, DM alpha | NM_006120 |
| HLA-DMB | HLA-DMB | MHC pathway | major histocompatibility complex, class II, DM beta | NM_002118 |
| HLA-DOA | HLA-DOA | MHC pathway | major histocompatibility complex, class II, DO alpha | NM_002119 |
| HLA-DOB | HLA-DOB | MHC pathway | major histocompatibility complex, class II, DO beta | NM_002120 |
| HLA-DPA1 | HLA-DPA1 | MHC pathway | major histocompatibility complex, class II, DP alpha 1 | NM_033554 |
| HLA-DQA2 | HLA-DQA2 | MHC pathway | major histocompatibility complex, class II, DQ alpha 2 | NM_020056 |
| HLA-DRA | HLA-DRA | MHC pathway | HLA-DRA | NM_019111 |
| HLX1 | H2.0-like homeo box 1 (*Drosophila*), Gene hCG25119 Celera Annotation | Th1 | Th1 | NM_021958.2 |
| HMOX1 | HO-1 | HO-1 | | NM_002133 |
| HRAS | expression of high levels of V12 HRAS - a constitutively active (and therefore oncogenic) mutant of HRAS - leads to a premature growth arrest that is similar in many respects to the arrest that is observed when human cells reach replicative senescence 68. | mutation and methylation | v-Ha-ras Harvey rat sarcoma viral oncogene homolog | NM_176795 |
| HSPB3 | heat shock 27 kDa protein 3 | | | NM_006308 |
| HUWE1 | UREB1, Proteolysis; Protein metabolism and modification | MHC pathway | ubiquitin, arf, Proteolysis; Protein metabolism and modification | NM_031407 |
| ICAM1 | metastasis | metastasis | | NM_000201 |
| ICAM-2 | CD102 | Adaptive immunity | | NM_000873 |
| ICOS | ICOS | Adaptive immunity | | NM_012092 |

TABLE 9-continued

| gene name (old) | alternate name | gene pathway | gene description | Public RefSeq |
|---|---|---|---|---|
| ID1 | inhibitor of DNA binding 1, dominant negative helix-loop-helix protein, Gene hCG37143 Celera Annotation | ID1, hCG37143 | metastasis signature | NM_002165.2 |
| ifna1 | Ifna1 | Interferon pathway | Interferon, alpha 1 | NM_024013 |
| ifna17 | Ifna17 | Interferon pathway | Interferon, alpha 17 | NM_021268 |
| ifna2 | Ifna2 | Interferon pathway | interferon, alpha 2 | NM_000605 |
| ifna5 | Ifna5 | Interferon pathway | interferon, alpha 5 | NM_002169 |
| ifna6 | Ifna6 | Interferon pathway | interferon, alpha 6 | NM_021002 |
| ifna8 | Ifna8 | Interferon pathway | interferon, alpha 8 | NM_002170 |
| IFNAR1 | ifnar1 | Interferon pathway | Interferon (alpha, beta and omega) receptor 1 | NM_000629 |
| IFNAR2 | ifnar2 | Interferon pathway | interferon (alpha, beta and omega) receptor 2 | NM_207584\| NM_207585\| NM_000874 |
| IFNG | IFN-g | Interferon pathway | IFG, IFI | NM_000619 |
| IFNGR1 | IFN-gamma R1 | Interferon pathway | | NM_000416 |
| IFNGR2 | IFN-gamma R2 | Interferon pathway | | NM_005534 |
| IGF1 | insulin-like growth factor 1 (somatomedin C) | growth pathway | | NM_000618 |
| IHH | | hedgehog pathway Indian hedgehog homolog (Drosophila) | Indian hedgehog homolog (Drosophila) | NM_002181 |
| IKBKB | IkB2 | CK pathway | | AF080158 |
| IL10 | IL-10 | CK pathway | | NM_000572 |
| IL12A | IL-12p35 | CK pathway | interleukin 12 | NM_000882 |
| IL12B | IL-12p40 | CK pathway | interleukin 12 | NM_002187 |
| IL12RB1 | IL-12 R beta 1 | Adaptive immunity | interleukin 12 receptor, beta 1 | NM_153701\| NM_005535 |
| IL12RB2 | IL12RB2 | CK pathway | interleukin 12 receptor, beta 2 | NM_001559 |
| IL13 | IL-13 | CK pathway | | NM_002188 |
| IL13RA2 | interleukin 13 receptor, alpha 2, Gene hCG20596 Celera Annotation | IL13RA2, hCG20596 | metastasis signature | NM_000640.2 |
| IL15 | IL-15 | CK pathway | | NM_000585 |
| IL15RA | IL-15 R alpha | CK pathway | interleukin 15 receptor, alpha | NM_002189 |
| IL17 | IL-17 | CK pathway | interleukin 17 (cytotoxic T-lymphocyte-associated serine esterase 8) | NM_002190 |

TABLE 9-continued

| gene name (old) | alternate name | gene pathway | gene description | Public RefSeq |
|---|---|---|---|---|
| IL17R | IL17R | CK pathway | interleukin 17 receptor | NM_014339 |
| IL17RB | IL17RB | CK pathway | Interleukin 17 receptor B | NM_018725\| NM_172234 |
| IL18 | IL-18 | CK pathway | | NM_001562 |
| IL1A | IL-1a | CK pathway | | NM_000575 |
| IL1B | IL-1b | CK pathway | | NM_000576 |
| IL1R1 | IL-1 RI | Adaptive immunity | | NM_000877 |
| IL2 | IL-2 | CK pathway | | NM_000586 |
| IL21 | IL-21 | CK pathway | Common gamma Chain Receptor Family | NM_021803 |
| IL21R | IL-21 R | CK pathway | Common gamma Chain Receptor Family | NM_181078\| NM_181079\| NM_021798 |
| IL23A | IL-23 | CK pathway | interleukin 23, alpha subunit p19 | NM_016584 |
| IL23R | IL-23R | CK pathway | interleukin 23 receptor | NM_144701 |
| IL24 | IL24 | CK pathway | Interleukin 24 | NM_006850 |
| IL27 | IL27 | CK pathway | interleukin 27 | NM_145659 |
| IL2RA | CD25 | CK pathway | | NM_000417 |
| IL2RB | IL-2 R beta, CD122 | CK pathway | Adaptive immunity | NM_000878 |
| IL2RG | IL-2 R gamma, CD132 | CK pathway | Adaptive immunity | NM_000206 |
| IL3 | IL-3 | CK pathway | | NM_000588 |
| IL31RA | IL31RA | CK pathway | interleukin 31 receptor A | NM_139017 |
| IL4 | IL-4 | CK pathway | | NM_000589 |
| IL4RA | IL-4 R | CK pathway | Th1/Th2 Cells | NM_001008699\| NM_000418 |
| IL5 | IL-5 | CK pathway | | NM_000879 |
| IL6 | IL-6 | CK pathway | | NM_000600 |
| IL7 | IL-7 | CK pathway | | NM_000880 |
| IL7RA | IL-7 R alpha | CK pathway | Adaptive immunity | NM_002185 |
| IL8 | CXCL8 | inflammation pathway | CK pathway | NM_000584 |
| CXCR1 | IL-8 RA | Adaptive immunity | | NM_000634 |
| CXCR2 | IL-8 RB | chemokine pathway | CXC Chemokines & Receptors | NM_001557 |
| IL9 | IL-9 | CK pathway | | NM_000590 |
| IL9R | IL-9 R | CK pathway | Common gamma Chain Receptor Family | NM_176786 |
| IRF1 | interferon regulatory factor 1 | Adaptive immunity | | NM_002198 |
| ISGF3G | interferon-stimulated transcription factor 3, gamma 48 kDa | Interferon pathway | interferon-stimulated transcription factor 3, gamma 48 kDa | NM_006084; |
| ITGA4 | integrin a4b7 | adhesion, metastasis | integrin, alpha 4 (antigen CD49D, alpha 4 subunit of VLA-4 receptor) | NM_000885 |
| ITGA7 | integrin, alpha 7 | adhesion, metastasis | | NM_002206 |

TABLE 9-continued

| gene name (old) | alternate name | gene pathway | gene description | Public RefSeq |
|---|---|---|---|---|
| integrin, alpha E (antigen CD103, human mucosal lymphocyte antigen 1; alpha polypeptide), Gene hCG33203 Celera Annotation | CD103 | Adaptive immunity | | NM_002208.3 |
| ITGB3 | integrin, beta 3 (platelet glycoprotein IIIa, antigen CD61), Gene hCG27604 Celera Annotation | metastasis | | NM_000212.2 |
| JAK2 | Janus kinase 2 (a protein tyrosine kinase), Gene hCG31308 Celera Annotation | JAK2, hCG31308 | | NM_004972.2 |
| JAK3 | | cytokine pathway | | NM_000215 |
| KLRB1 | | Adaptive immunity | DNA microarray T | NM_002258.2 |
| KLRC4 | killer cell lectin-like receptor subfamily C, member 4, killer cell lectin-like receptor subfamily K, member 1, Gene hCG2009644 Celera Annotation | AF030313 | | NM_007360.1 |
| KLRF1 | | Adaptive immunity | DNA microarray T | NM_016523.1 |
| KLRG1 | killer cell lectin-like receptor subfamily G, member 1, Gene hCG25214 Celera Annotation | AF097367 | | NM_005810.3 |
| KRAS | | | | NM_004985 |
| LAG3 | immune | Adaptive immunity | lymphocyte-activation gene 3 | NM_002286 |
| LAIR2 | | Adaptive immunity | | NM_002288\| NM_021270 |
| LEF1 | lymphoid enhancer-binding factor 1 | lymphoid enhancer-binding factor 1 | | NM_016269 |
| LGALS9 | lectin, galactoside-binding, soluble, 9 (galectin 9), Gene hCG1749919 Celera Annotation | | | NM_009587.1\| NM_002308.2 |
| LILRB3 | leukocyte immunoglobulin-like receptor, subfamily B | IRT5 Wang microarray | immunosuppression | |

TABLE 9-continued

| gene name (old) | alternate name | gene pathway | gene description | Public RefSeq |
|---|---|---|---|---|
| | (with TM and ITIM domains), member 3 | | | |
| LRP2 | MEGALIN | | MEGALIN | NM_004525 |
| LTA | TNF-b | CK pathway | LT, TNFB, TNFSF1 | NM_000595 |
| SLAMF3 | CD229 | Adaptive immunity | | NM_002348 |
| MADCAM1 | mucosal vascular addressin cell adhesion molecule 1, Gene hCG20569 Celera Annotation | | MADCAM1, hCG20569 | NM_130760.1\| NM_130761.1 |
| MADH3 | MADH-3 | TGF pathway | SMAD3, JV15-2 | NM_005902 |
| MADH7 | MADH-7 | TGF pathway | MADH8, SMAD7 | NM_005904 |
| MAF | c-maf Th2 | CK pathway | v-maf musculoaponeurotic fibrosarcoma oncogene homolog (avian) | NM_005360 |
| MAP2K1 | | | | NM_002755 |
| MDM2 | Mdm2, transformed 3T3 cell double minute 2, p53 binding protein (mouse) | p53 pathway | | NM_002392; NM_006878; NM_006879; NM_006880; NM_006881; NM_006882; |
| MICA | MHC class I polypeptide-related sequence A | MHC pathway | present sur cell turn et module cytotox | NM_000247 |
| MICB | MHC class I polypeptide-related sequence B | MHC pathway | present sur cell turn et module cytotox | NM_005931 |
| MKI67 | proliferation | proliferation | | NM_002417 |
| MMP12 | matrix metallopeptidase 12 (macrophage elastase) | adhesion, metastasis | | NM_002426 L23808 |
| MMP9 | matrix metallopeptidase 9 (gelatinase B, 92 kDa gelatinase, 92 kDa type IV collagenase) | adhesion, metastasis | | NM_004994 |
| MTA1 | Metastasis associated 1, Gene hCG19442 Celera Annotation | metastasis | | NM_004689.2 |
| MTSS1 | Metastasis suppressor 1, Gene hCG2009512 Celera Annotation | metastasis | | NM_014751.2 |
| MYC | MYC | TGF pathway | v-myc myelocytomatosis viral oncogene homolog (avian) | NM_002467 |

TABLE 9-continued

| gene name (old) | alternate name | gene pathway | gene description | Public RefSeq |
|---|---|---|---|---|
| MYD88 | | Toll-like pathway | | NM_002468 |
| MYH6 | MYH6 | MYH6 | | D00943 (Gene card) |
| NCAM1 | | Adaptive immunity | | |
| NFATC1 | activation T | activation T | | NM_172387\| NM_172388\| NM_172389\| NM_172390\| NM_006162 |
| NKG7 | | Adaptive immunity | DNA microarray T | NM_005601.3 |
| NLK | | wnt pathway | nemo like kinase | NM_016231 |
| NOS2A | iNos(Nos2A) | iNos(Nos2A) | | NM_000625 |
| P2X7 | Purinergic receptor P2X, ligand-gated ion channel, 7, Gene hCG1641456 Celera Annotation | P2RX7, hCG1641456 | | NM_177427.2\| NM_002562.4 |
| PDCD1 | PD-1 | Adaptive immunity | | NM_005018 |
| PECAM-1 | CD31 | Adaptive immunity | | NM_000442 |
| CXCL4 | PF4 | chemokine pathway | CXC Chemokines & Receptors | NM_002619 |
| PGK1 | PGK1 | endogenous control | endogenous control | NM_000291 |
| PIAS1 | | CK pathway | protein inhibitor of activated STAT, 1 | NM_016166 |
| PIAS2 | | CK pathway | protein inhibitor of activated STAT, 2 | NM_173206\| NM_004671 |
| PIAS3 | | CK pathway | protein inhibitor of activated STAT, 3 | NM_006099 |
| PIAS4 | | CK pathway | protein inhibitor of activated STAT, 4 | NM_015897 |
| PLAT | plasminogen activator, tissue, Gene hCG17154 Celera Annotation | PLAT, hCG17154 | | NM_033011.1\| NM_000930.2\| NM_000931.2 |
| PML | tumor suppressor, interferon signalling | | | NM_033238\| NM_033239\| NM_033240\| NM_033242\| NM_033244\| NM_033245\| NM_033246\| NM_033247\| NM_033249\| NM_033250\| NM_002675 |
| PP1A | PP1 | PP1 | | NM_021130 |
| CXCL7 | NAP-2 | chemokine pathway | | NM_002704 |
| PPP2CA | PP2A | | | NM_002715 |
| PRF1 | Perforin (PRF1) | Cytotox pathway | P1, PFP, HPLH2 | NM_005041 |
| PROM1 | CD133, prominin 1, pentaspan transmembrane glycoprotein, | | CD133 positive fraction of human bone marrow, cord blood and peripheral blood have | NM_006017 |

TABLE 9-continued

| gene name (old) | alternate name | gene pathway | gene description | Public RefSeq |
|---|---|---|---|---|
| | | | been shown to efficiently engraft in xenotransplantation models, and have been shown to contain the majority of the granulocyte/macrophage precursors, | |
| PSMB5 | proteasome (prosome, macropain) subunit, beta type, 5 | MHC pathway | | NM_002797 |
| PTCH | | hedgehog pathway patched homolog (Drosophila) | | NM_000264 |
| PTGS2 | COX-2 | inflammation pathway | | NM_000963 |
| PTP4A3 | protein tyrosine phosphatase type IVA, member 3 | metastasis | | NM_032611.1 |
| PTPN6 | | CK pathway | protein tyrosine phosphatase, non-receptor type 6 | NM_080548|NM_080549| NM_002831 |
| PTPRC | CD45 | CD45 | | NM_002838, NM_080922, NM_080923, NM_080921 |
| RAB23 | | hedgehog pathway RAB23, member RAS oncogene family | | NM_183227|NM_016277 |
| RAC/RHO | | | | NM_018890 |
| RAC2 | RAC2 | RAC2 | ras-related C3 botulinum toxin substrate 2 (rho family, small GTP binding protein Rac2) | NM_002872 |
| RAF | | | | NM_002880 |
| RB1 | retinoblastoma 1 (including osteosarcoma) | mutation and methylation | cell cycle | NM_000321; |
| RBL1 | retinoblastoma-like 1 (p107) | retinoblastoma-like 1 (p107) | | NM_183404| NM_002895 |
| REN | RENIN (REN) | | RENIN (REN) | NM_000537 |
| Drosha | RNASEN, Droshan microRNA | microRNA | | AJ242976 |
| SELE | CD62E (SELE) | metastasis | | NM_000450 |
| SELL | CD62L | | | NM_000655 |
| SELP | CD62E (SELP) | metastasis | | NM_003005 |
| SERPINE1 | serpin peptidase inhibitor, clade E (nexin, plasminogen activator inhibitor type 1), member 1, Gene hCG17353 Celera Annotation | SERPINE1, hCG17353 | | NM_000602.1 |

TABLE 9-continued

| gene name (old) | alternate name | gene pathway | gene description | Public RefSeq |
|---|---|---|---|---|
| SFRP1 | secreted frizzled | secreted frizzled | | NM_003012 |
| SIRP beta 1 | | Adaptive immunity | | NM_006065 |
| SKI | c-ski (SKI) | c-ski (SKI) | SKV | NM_003036 |
| SLAMF1 | | Adaptive immunity | | NM_003037 |
| SLAMF6 | NTB-A | Adaptive immunity | | NM_052931 |
| SLAMF7 | CRACC | Adaptive immunity | | NM_021181 |
| SLAMF8 | BLAME | Adaptive immunity | | NM_020125 |
| SMAD2 | SMAD2 | TGF pathway | SMAD, mothers against DPP homolog 2 (*Drosophila*) | NM_001003652\| NM_005901 |
| SMAD4 | SMAD4 | TGF pathway | SMAD, mothers against DPP homolog 4 (*Drosophila*) | NM_005359 |
| SMO, SMOH | SMO | SMO | smoothened homolog (*Drosophila*) | NM_005631 |
| SMURF1 | SMURF1 | SMURF1 | SMAD specific E3 ubiquitin protein ligase 1 | NM_181349\| NM_020429 |
| SOCS1 | | CK pathway | suppressor of cytokine signaling 1 | NM_003745 |
| SOCS2 | | CK pathway | suppressor of cytokine signaling 2 | NM_003877 |
| SOCS3 | | CK pathway | suppressor of cytokine signaling 3 | NM_003955 |
| SOCS4 | | CK pathway | suppressor of cytokine signaling 4 | NM_199421\| NM_080867 |
| SOCS5 | | CK pathway | suppressor of cytokine signaling 5 | NM_014011 |
| SOCS6 | | CK pathway | suppressor of cytokine signaling 6 | NM_004232 |
| SOCS7 | | CK pathway | suppressor of cytokine signaling 7 | NM_014598 |
| SOD1 | anti-oxidant | anti-oxidant | | NM_000454 |
| SOD2 | anti-oxidant | anti-oxidant | | NM_001024465\| NM_001024466\| NM_000636 |
| SOD3 | anti-oxidant | anti-oxidant | | NM_003102 |
| SOS1 | | TCR pathway | | NM_005633 |
| SOX17 | SOX17 | SOX17 | SRY (sex determining region Y)-box 17 | NM_022454 |
| CD43 | | Adaptive immunity | | NM_003123 |
| ST14 | suppression of tumorigenicity 14 (colon carcinoma, matriptase, epithin) | protease, cytotox | | NM_021978 |
| STAM | STAM | STAM | signal transducing adaptor molecule (SH3 domain and ITAM motif) 1 | NM_003473 |
| STAT1 | STAT1 | STAT1 | Signal transducer | NM_139266\| NM_007315 |

TABLE 9-continued

| gene name (old) | alternate name | gene pathway | gene description | Public RefSeq |
|---|---|---|---|---|
| | | | and activator of transcription 1, 91 kDa | |
| STAT2 | STAT2 | STAT2 | signal transducer and activator of transcription 2, 113 kDa | |
| STAT3 | STAT3 | STAT3 | Signal transducer and activator of transcription 3 (acute-phase response factor) | NM_213662\| NM_139276\| NM_003150 |
| STAT4 | STAT4 | STAT4 | signal transducer and activator of transcription 4 | NM_003151 |
| STAT5A | STAT5A | STAT5A | signal transducer and activator of transcription 5A | NM_003152 |
| STAT5B | STAT5B | STAT5B | signal transducer and activator of transcription 5B | NM_012448 |
| STAT6 | STAT6 | STAT6 | signal transducer and activator of transcription 6, interleukin-4 induced | NM_003153 |
| STK36 | STK36 | STK36 | serine/threonine kinase 36 (fused homolog, *Drosophila*) | NM_015690 |
| TAP1 | transporter 1, ATP-binding cassette, sub-family B (MDR/TAP) | MHC pathway | | NM_000593 |
| TAP2 | transporter 2, ATP-binding cassette, sub-family B (MDR/TAP) | MHC pathway | transporter 2, ATP-binding cassette, sub-family B (MDR/TAP) | NM_000544 |
| TBX21 | T-bet (TBX21) | Adaptive immunity | | NM_013351 |
| TCF7 | TCF7 | wnt pathway | transcription factor 7 (T-cell specific, HMG-box) | NM_201633\| NM_201632\| NM_201634\| NM_213648\| NM_003202 |
| TERT | | | | NM_198255\| NM_003219 |
| TFRC | CD71 | endogenous control | endogenous control | NM_003234 |
| TGFA | | | | NM_003236 |
| TGFB1 | TGF-b/ BIGH3 | TGF pathway | | NM_000660 |
| TGFBR1 | TGFBR1 | TGF pathway | transforming growth factor, beta receptor I | NM_004612 |

TABLE 9-continued

| gene name (old) | alternate name | gene pathway | gene description | Public RefSeq |
|---|---|---|---|---|
| TGFBR2 | TGFBR2 | TGF pathway | (activin A receptor type II-like kinase, 53 kDa) transforming growth factor, beta receptor II (70/80 kDa) | NM_001024847\| NM_003242 |
| TIMP3 | TIMP metallopeptidase inhibitor 3 (Sorsby fundus dystrophy, pseudoinflammatory) | TGF pathway | adhesion, metastasis | NM_000362 |
| TLR1 | TLR1 | Toll-like pathway | toll-like receptor 1 | NM_003263 |
| TLR10 | TLR10 | Toll-like pathway | toll-like receptor 10 | NM_030956 |
| TLR2 | TLR2 | Toll-like pathway | toll-like receptor 2 | NM_003264 |
| TLR3 | TLR3 | Toll-like pathway | toll-like receptor 3 | NM_003265 |
| TLR4 | TLR4 | Toll-like pathway | toll-like receptor 4 | NM_138554\| NM_003266 |
| TLR5 | TLR5 | Toll-like pathway | toll-like receptor 5 | NM_003268 |
| TLR6 | TLR6 | Toll-like pathway | toll-like receptor 6 | NM_006068 |
| TLR7 | TLR7 | Toll-like pathway | toll-like receptor 7 | NM_016562 |
| TLR8 | TLR8 | Toll-like pathway | toll-like receptor 8 | NM_138636 |
| TLR9 | TLR9 | Toll-like pathway | toll-like receptor 9 | NM_017442\| NM_138688 |
| TNF | TNF-a | TNF-a | DIF, TNFA, TNFSF2, CACHECTIN | NM_000594 |
| TNFRSF10A | TRAILR1 | apoptosis pathway | | NM_003844 |
| TNFRSF11A | RANK | Adaptive immunity | | NM_003839 |
| TNFRSF18 | GITR (TNFRSF18) | Adaptive immunity | | NM_004195 |
| TNFRSF1A | TNF RI | Adaptive immunity | | NM_001065 |
| TNFRSF1B | TNF RII | Adaptive immunity | | NM_001066 |
| OX-40 | | | | NM_003327 |
| TNFRSF5 | CD40 | Adaptive immunity | | NM_001250, NM_152854 |
| TNFRSF6 | Fas | Apoptosis pathway | FAS, APT1, CD95, APO-1, FASTM | NM_000043 |
| TNFRSF7 | CD27 | Adaptive immunity | | NM_001242 |
| TNFRSF8 | CD30 | Adaptive immunity | | NM_152942\| NM_001243 |
| TNFRSF9 | 4-1BB | Adaptive immunity | | NM_001561 |
| TNFSF10 | TRAIL | | tumor necrosis factor (ligand) superfamily, member 10 | NM_003810 |
| TNFSF6 | FasL | apopyosis pathway | FASL, FasL, CD178, CD95L, APT1LG1 | NM_000639 |
| TOB1 | transducer of ERBB2 | TCR pathway | transducer of ERBB2, 1 | NM_005749 |
| TP53 | tumor protein p53 (Li-Fraumeni syndrome) | p53 pathway | | NM_000546 |
| TSLP | | Adaptive immunity | | NM_033035\| NM_138551 |
| VCAM1 | vascular cell adhesion molecule 1, Gene | MGC99561, INCAM-100, DKFZp779G2333, HGNC: 12663 | metastasis signature | NM_001078.2 |

TABLE 9-continued

| gene name (old) | alternate name | gene pathway | gene description | Public RefSeq |
|---|---|---|---|---|
| | hCG32384 Celera Annotation | | | |
| VEGF | VEGF A | VEGF A | | NM_003376 |
| WIF1 | | wnt pathway | inhibitory factor 1 | NM_007191 |
| WNT1 | | wnt pathway | wingless-type MMTV integration site family, member 1 | NM_005430 |
| WNT4 | wingless-type MMTV integration site family, member 4 | wnt pathway | wingless-type MMTV integration site family, member 4 | NM_030761 |
| XCL1 | Lymphotactin | chemokine pathway | chemokine (C motif) ligand 1 | NM_002995 |
| XCR1 | | chemokine pathway | chemokine (C motif) receptor 1 | NM_001024644\| NM_005283 |
| ZAP70 | ZAP70 | TCR pathway | zeta-chain (TCR) associated protein kinase 70 kDa | NM_001079 |
| ZIC2 | | hedgehog pathway Zic family member 2 (odd-paired homolog, *Drosophila*) | Zic family member 2 (odd-paired homolog, *Drosophila*) | NM_007129 |

TABLE 10

| Access. N° | Name | Description | Type | Location |
|---|---|---|---|---|
| 2 transcripts | TNFRSF6B | tumor necrosis factor receptor superfamily, member 6b, decoy | hCG22751:7 transcripts | 20q13.3 |
| NM_001712 | CEACAM1 | Carcinoembryonic antigen-related cell adhesion molecule 1 (biliary glycoprotein) | hCG21881:2 transcripts | 19q13.2, |
| NM_014143 | PDCD1LG1 | programmed cell death 1 ligand 1 | hCG27938:1 transcripts | 9p24, |
| 2 transcripts | CD8A | CD8 antigen, alpha polypeptide (p32) | hCG34192:3 transcripts | 2p12 |
| NM_000963 | PTGS2 | Prostaglandin-endoperoxide synthase 2 (prostaglandin G/H synthase and cyclooxygenase) | hCG39885:1 transcripts | 1q25.2-q25.3, |
| NM_001168 | BIRC5 | baculoviral IAP repeat-containing 5 (survivin) | hCG27811:4 transcripts | 17q25, |
| NM_000655 | SELL | selectin L (lymphocyte adhesion molecule 1) | hCG37088:5 transcripts | 1q23-q25, |
| NM_002164 | INDO | indoleamine-pyrrole 2,3 dioxygenase | hCG27061:2 transcripts | 8p12-p11, |
| NM_016123 | IRAK4 | interleukin-1 receptor-associated kinase 4 | hCG39494:1 transcripts | 4, |
| NM_000594 | TNF | tumor necrosis factor (TNF superfamily, member 2) | hCG43716:1 transcripts | 6p21.3, |
| NM_003844 | TNFRSF10A | tumor necrosis factor receptor superfamily, member 10a | hCG31588:1 transcripts | 8p21, |
| NM_002423 | MMP7 | Matrix metalloproteinase 7 (matrilysin, uterine) | hCG1640914:1 transcripts | 11q21-q22, |

TABLE 10-continued

| Access. N° | Name | Description | Type | Location |
|---|---|---|---|---|
| NM_006864 | LILRB3 | Leukocyte immunoglobulin-like receptor, subfamily B (with TM and ITIM domains), member 3 | hCG2009348:1 transcripts | 19q13.4, |
| 2 transcripts | CD3Z | CD3Z antigen, zeta polypeptide (TiT3 complex) | hCG1769040:2 transcripts | 1q22-q23, |
| 2 transcripts | TNFRSF8 | tumor necrosis factor receptor superfamily, member 8 | hCG25063:1 transcripts | 1p36, |
| NM_002046 | GAPD | glyceraldehyde-3-phosphate dehydrogenase | hCG2005673:1 transcripts | 12p13, |
| NM_001565 | CXCL10 | chemokine (C—X—C motif) ligand 10 | hCG23842:2 transcripts | 4q21, |
| 2 transcripts | EBAG9 | estrogen receptor binding site associated, antigen, 9 | hCG15046:2 transcripts | 8q23, |
| NM_000584 | IL8 | interleukin 8 | hCG16372:2 transcripts | 4q13-q21 |
| 2 transcripts | STAT1 | signal transducer and activator of transcription 1, 91 kDa | hCG25794:6 transcripts | 2q32.2, |
| NM_001504 | CXCR3 | chemokine (C—X—C motif) receptor 3 | hCG19964:1 transcripts | Xq13, |
| NM_000660 | TGFB1 | transforming growth factor, beta 1 (Camurati-Engelmann disease) | hCG22321:2 transcripts | 19q13.2, |
| NM_012092 | ICOS | inducible T-cell co-stimulator | hCG1642889:1 transcripts | 2q33, |
| NM_002416 | CXCL9 | chemokine (C—X—C motif) ligand 9 | hCG1781951:1 transcripts | 4q21, |
| 2 transcripts | CD97 | CD97 antigen | hCG27517:5 transcripts | 19p13, |
| NM_003853 | IL18RAP | interleukin 18 receptor accessory protein | hCG28161:1 transcripts | 2p24.3-p24.1 |
| NM_006564 | CXCR6 | chemokine (C—X—C motif) receptor 6 | hCG15326:1 transcripts | 3p21, |
| NM_004314 | ART1 | ADP-ribosyltransferase 1 | hCG16165:1 transcripts | 11p15, |
| NM_002198 | IRF1 | interferon regulatory factor 1 | hCG24115:1 transcripts | 5q31.1, |
| NM_025240 | B7H3 | B7 homolog 3 | hCG40826:1 transcripts | 15q23-q24, |
| 3 transcripts | ACE | angiotensin I converting enzyme (peptidyl-dipeptidase A) 1 | hCG41821:5 transcripts | 17q23, |
| NM_003855 | IL18R1 | interleukin 18 receptor 1 | hCG28160:3 transcripts | 2q12 |
| NM_013351 | TBX21 | T-box 21 | hCG27200:1 transcripts | 17q21.2, |
| NM_001562 | IL18 | interleukin 18 (interferon-gamma-inducing factor) | hCG39294:2 transcripts | 11q22.2-q22.3 |
| NM_005018 | PDCD1 | programmed cell death 1 | hCG1776289:1 transcripts | 2q37.3, |
| NM_000619 | IFNG | interferon, gamma | hCG15987:1 transcripts | 12q14, |
| 2 transcripts | GNLY | Granulysin | hCG32948:3 transcripts | 2p12-q11, |
| NM_002051 | GATA3 | GATA binding protein 3 | hCG23634:3 transcripts | 10p15, |
| NM_003376 | VEGF | vascular endothelial growth factor | hCG18998:7 transcripts | 6p12 |
| NM_004131 | GZMB | granzyme B (granzyme 2, cytotoxic T-lymphocyte-associated serine esterase 1) | hCG40183:1 transcripts | 14q11.2, |
| NM_014387 | LAT | linker for activation of T cells | hCG2039637:5 transcripts | 16q13, |
| NM_000616 | CD4 | CD4 antigen (p55) | hCG25949:2 transcripts | 12pter-p12, |

TABLE 10-continued

| Access. N° | Name | Description | Type | Location |
|---|---|---|---|---|
| NM_031281 | IRTA2 | immunoglobulin superfamily receptor translocation associated 2 | hCG39827:3 transcripts | 1q21, |
| NM_000572 | IL10 | interleukin 10 | hCG22208:1 transcripts | 1q31-q32, |
| NM_003326 | TNFSF4 | tumor necrosis factor (ligand) superfamily, member 4 (tax-transcriptionally activated glycoprotein 1, 34 kDa) | hCG37644:2 transcripts | 1q25, |
| NM_018676 | THSD1 | thrombospondin, type I, domain 1 | hCG29569:4 transcripts | 13q14.13, |
| NM_025239 | PDCD1LG2 | programmed cell death 1 ligand 2 | hCG1641650:1 transcripts | 9p24.2, |

TABLE 11

Table S1: Characteristics of the three cohorts of patients

| Characteristic | Cohorts | | |
|---|---|---|---|
| | HEGP | Avicenne | HEGP-2 |
| | | No. of Patients | |
| Tumor (T) stage† | | | |
| pT1 | 23 | 3 | 2 |
| pT2 | 69 | 13 | 7 |
| pT3 | 218 | 76 | 57 |
| pT4 | 97 | 27 | 9 |
| Nodal (N) status | | | |
| Negative | 241 | 48 | 30 |
| Positive | 166 | 71 | 43 |
| Nx‡ | | | 2 |
| Distant metastases (M) | | | |
| None detected | 313 | 93 | 47 |
| Present | 94 | 26 | 28 |
| UICC-TNM Classification (25) | | | |
| I | 75 | 12 | 6 |
| II | 137 | 33 | 17 |
| III | 100 | 48 | 24 |
| IV | 95 | 26 | 28 |
| Sex | | | |
| Male | 216 | 57 | 42 |
| Female | 191 | 62 | 33 |
| Location | | | |
| Colon | 162 | 35 | 41 |
| Sigmoid | 114 | 53 | 25 |
| Rectum | 131 | 31 | 9 |
| Differentiation | | | |
| Well | 312 | 78 | 47 |
| Poor | 95 | 41 | 28 |

†The stage was determined by pathological (p) examination. T1 tumor invading submucosa, T2 tumor invading muscularis propria, T3 tumor penetrating muscularis propria and invading subserosa, and T4 tumor invading other organs or structures or perforating visceral peritoneum.
‡It was not possible to determine the nodal status of two patients.

TABLE 12

Table S3: Disease-free survival analyses for all patients according to the minimum P-value cut-offs

| | Disease-Free Survival (DFS) for all patients | | | | | | |
|---|---|---|---|---|---|---|---|
| | No. of patients | Median months | Rate at 2 yr % | Rate at 4 yr % | Rate at 5 yr % | P value* | P value† | P value‡ |
| $GZMB_{CT}$ | | | | | | $1.78\ 10^{-4}$ | $9.70\ 10^{-5}$ | $4.85\ 10^{-5}$ |
| Lo | 191 | 34.6 | 53.8 | 46.1 | 46.1 | | | |
| Hi | 163 | NR | 76.6 | 73.1 | 72.1 | | | |
| $GZMB_{IM}$ | | | | | | $1.99\ 10^{-5}$ | $1.28\ 10^{-5}$ | $5.38\ 10^{-6}$ |
| Lo | 109 | 20.1 | 47.1 | 41.0 | 41.0 | | | |
| Hi | 195 | NR | 75.4 | 70.9 | 70.0 | | | |
| $CD45RO_{CT}$ | | | | | | $4.33\ 10^{-5}$ | $9.81\ 10^{-5}$ | $1.27\ 10^{-4}$ |
| Lo | 45 | 11.5 | 27.5 | 24.0 | 24.0 | | | |
| Hi | 261 | NR | 72.0 | 65.5 | 64.9 | | | |
| $CD45RO_{IM}$ | | | | | | $3.71\ 10^{-3}$ | $4.29\ 10^{-4}$ | $4.41\ 10^{-4}$ |
| Lo | 168 | 41.5 | 55.4 | 47.3 | 47.3 | | | |
| Hi | 145 | NR | 76.8 | 72.9 | 71.9 | | | |
| $CD8_{CT}$ | | | | | | $5.19\ 10^{-6}$ | $3.44\ 10^{-6}$ | $1.45\ 10^{-6}$ |
| Lo | 132 | 21.0 | 46.0 | 39.1 | 39.1 | | | |
| Hi | 227 | NR | 74.9 | 69.5 | 68.8 | | | |

TABLE 12-continued

Table S3: Disease-free survival analyses for all patients according to the minimum P-value cut-offs

| | No. of patients | Median months | Rate at 2 yr % | Rate at 4 yr % | Rate at 5 yr % | P value* | P value† | P value‡ |
|---|---|---|---|---|---|---|---|---|
| $CD8_{IM}$ | | | | | | $1.08\ 10^{-2}$ | $1.11\ 10^{-2}$ | $8.09\ 10^{-3}$ |
| Lo | 186 | 45.5 | 56.4 | 49.1 | 49.1 | | | |
| Hi | 128 | NR | 77.8 | 73.5 | 72.3 | | | |
| $CD3_{CT}$ | | | | | | $5.48\ 10^{-6}$ | $1.38\ 10^{-5}$ | $1.09\ 10^{-6}$ |
| Lo | 165 | 23.1 | 48.2 | 43.4 | 43.4 | | | |
| Hi | 192 | NR | 79.8 | 72.4 | 71.6 | | | |
| $CD3_{IM}$ | | | | | | $4.78\ 10^{-6}$ | $6.23\ 10^{-5}$ | $6.32\ 10^{-6}$ |
| Lo | 175 | 31.1 | 51.8 | 43.5 | 48.5 | | | |
| Hi | 178 | NR | 78.7 | 74.7 | 73.9 | | | |
| $GZMB_{CT/IM}$ | | | | | | $3.32\ 10^{-4}$ | $8.34\ 10^{-5}$ | $5.45\ 10^{-5}$ |
| Lo/Lo | 70 | 20.1 | 46.3 | 39.1 | 39.1 | | | |
| Het | 98 | 77.5 | 62.2 | 54.4 | 54.4 | | | |
| Hi/Hi | 102 | NR | 80.6 | 77.8 | 76.3 | | | |
| $CD45RO_{CT/IM}$ | | | | | | $6.61\ 10^{-3}$ | $1.05\ 10^{-5}$ | $1.69\ 10^{-5}$ |
| Lo/Lo | 32 | 5.85 | 24.2 | 24.2 | 24.2 | | | |
| Het | 141 | 63.28 | 61.2 | 50.7 | 50.7 | | | |
| Hi/Hi | 127 | NR | 80.3 | 78.1 | 76.9 | | | |
| $CD8_{CT/IM}$ | | | | | | $3.80\ 10^{-5}$ | $7.70\ 10^{-5}$ | $5.52\ 10^{-5}$ |
| Lo/Lo | 93 | 20.1 | 44.3 | 35.9 | 35.9 | | | |
| Het | 94 | NR | 63.8 | 58.9 | 58.9 | | | |
| Hi/Hi | 96 | NR | 81.6 | 76.1 | 74.6 | | | |
| $CD3_{CT/IM}$ | | | | | | $7.56\ 10^{-3}$ | $1.22\ 10^{-7}$ | $1.16\ 10^{-7}$ |
| Lo/Lo | 93 | 17.3 | 42.8 | 37.4 | 37.4 | | | |
| Het | 116 | 68.7 | 61.7 | 51.8 | 51.8 | | | |
| Hi/Hi | 109 | NR | 87.6 | 84.0 | 82.7 | | | |

*Log-rank P value corrected (Altman et al. 1994),
†P value median 100 * CV Log-rank
‡P value median 100 * CV stratified Log-rank
NR: Not Reached,
Het: Hi/Lo and Lo/Hi

TABLE 13

Table S4: Overall survival analyses for all patients according to the minimum P-value cut-offs

| | No. of patients | Median months | Rate at 2 yr % | Rate at 4 yr % | Rate at 5 yr % | P value* | P value† | P value‡ |
|---|---|---|---|---|---|---|---|---|
| $GZMB_{CT}$ | | | | | | $8.18\ 10^{-7}$ | $1.29\ 10^{-5}$ | $1.16\ 10^{-5}$ |
| Lo | 191 | 42.7 | 62.2 | 47.3 | 40.1 | | | |
| Hi | 163 | NR | 83.8 | 76.0 | 68.4 | | | |
| $GZMB_{IM}$ | | | | | | $5.55\ 10^{-3}$ | $8.39\ 10^{-2}$ | $6.77\ 10^{-2}$ |
| Lo | 109 | 43 | 68.6 | 47.3 | 39.9 | | | |
| Hi | 195 | 89.0 | 74.6 | 66.7 | 57.8 | | | |
| $CD45RO_{CT}$ | | | | | | $5.77\ 10^{-7}$ | $8.99\ 10^{-5}$ | $6.57\ 10^{-5}$ |
| Lo | 45 | 25.6 | 55.5 | 26.9 | 20.9 | | | |
| Hi | 261 | 100.7 | 74.9 | 66.3 | 58.7 | | | |
| $CD45RO_{IM}$ | | | | | | $1.65\ 10^{-3}$ | $8.20\ 10^{-3}$ | $1.07\ 10^{-2}$ |
| Lo | 168 | 46.9 | 67.1 | 49.4 | 42.0 | | | |
| Hi | 145 | NR | 78.6 | 73.3 | 65.5 | | | |
| $CD8_{CT}$ | | | | | | $2.66\ 10^{-7}$ | $6.66\ 10^{-6}$ | $3.79\ 10^{-6}$ |
| Lo | 132 | 35.1 | 60.3 | 41.8 | 36.5 | | | |
| Hi | 227 | NR | 79.8 | 71.0 | 62.3 | | | |
| $CD8_{IM}$ | | | | | | $1.22\ 10^{-3}$ | $1.51\ 10^{-2}$ | $1.50\ 10^{-2}$ |
| Lo | 186 | 51.3 | 70.2 | 61.6 | 43.0 | | | |
| Hi | 128 | NR | 78.4 | 72.6 | 66.1 | | | |
| $CD3_{CT}$ | | | | | | $7.86\ 10^{-8}$ | $1.35\ 10^{-5}$ | $9.65\ 10^{-6}$ |
| Lo | 165 | 33.5 | 57.9 | 42.4 | 35.6 | | | |
| Hi | 192 | 115.1 | 83.2 | 74.3 | 66.4 | | | |
| $CD3_{IM}$ | | | | | | $9.08\ 10^{-5}$ | $1.83\ 10^{-4}$ | $1.46\ 10^{-4}$ |
| Lo | 175 | 46.9 | 65.9 | 49.3 | 40.3 | | | |
| Hi | 178 | NR | 77.3 | 70.2 | 64.0 | | | |
| $GZMB_{CT/IM}$ | | | | | | $2.00\ 10^{-4}$ | $1.67\ 10^{-2}$ | $1.60\ 10^{-2}$ |
| Lo/Lo | 70 | 50.8 | 72.4 | 50.7 | 45.2 | | | |
| Het | 98 | 40.3 | 60.8 | 48.0 | 35.4 | | | |
| Hi/Hi | 102 | NR | 84.1 | 77.8 | 70.8 | | | |

TABLE 13-continued

Table S4: Overall survival analyses for all patients according to the minimum P-value cut-offs

| | \ | Overall Survival (OS) for all patients | | | | | |
|---|---|---|---|---|---|---|---|
| | No. of patients | Median months | Rate at 2 yr % | Rate at 4 yr % | Rate at 5 yr % | P value* | P value† | P value‡ |
| $CD45RO_{CT/IM}$ | | | | | | $8.56\ 10^{-6}$ | $3.34\ 10^{-4}$ | $2.91\ 10^{-4}$ |
| Lo/Lo | 32 | 28.4 | 60.6 | 22.5 | 22.5 | | | |
| Het | 141 | 51.5 | 66.3 | 54.5 | 44.1 | | | |
| Hi/Hi | 127 | NR | 81.2 | 76.1 | 70.5 | | | |
| $CD8_{CT/IM}$ | | | | | | $6.25\ 10^{-6}$ | $4.69\ 10^{-4}$ | $4.28\ 10^{-4}$ |
| Lo/Lo | 93 | 35.1 | 61.2 | 40.0 | 33.8 | | | |
| Het | 94 | 59.6 | 74.6 | 61.0 | 49.3 | | | |
| Hi/Hi | 96 | NR | 82.3 | 75.9 | 69.2 | | | |
| $CD3_{CT/IM}$ | | | | | | $3.97\ 10^{-7}$ | $2.11\ 10^{-6}$ | $1.37\ 10^{-6}$ |
| Lo/Lo | 93 | 35.1 | 59.3 | 40.7 | 29.9 | | | |
| Het | 116 | 57.8 | 68.0 | 54.7 | 49.5 | | | |
| Hi/Hi | 109 | NR | 86.4 | 80.8 | 72.6 | | | |

*Log-rank P value,
†P value median 100 * CV Log-rank
‡P value median 100 * CV stratified Log-rank
NR: Not Reached,
Het: Hi/Lo and Lo/Hi

TABLE 14

Table S5: Disease-free survival analyses for all patients according to median cut-offs

| | Disease-Free Survival (DFS) for all patients | | | | |
|---|---|---|---|---|---|
| | No. of patients | Median months | Rate at 2 yr % | Rate at 4 yr % | Rate at 5 yr % | P value* |
| $GZMB_{CT}$ | | | | | | $9.94\ 10^{-7}$ |
| Lo | 190 | 34.6 | 53.5 | 45.7 | 45.7 | |
| Hi | 164 | NR | 76.8 | 73.2 | 72.3 | |
| $GZMB_{IM}$ | | | | | | $1.99\ 10^{-6}$ |
| Lo | 152 | 31.1 | 51.0 | 46.6 | 46.6 | |
| Hi | 152 | NR | 79.5 | 73.6 | 72.5 | |
| $CD45RO_{CT}$ | | | | | | $2.21\ 10^{-2}$ |
| Lo | 153 | 77.4 | 59.3 | 54.2 | 54.2 | |
| Hi | 153 | NR | 72.9 | 65.8 | 64.8 | |
| $CD45RO_{IM}$ | | | | | | $1.85\ 10^{-4}$ |
| Lo | 158 | 36.0 | 53.7 | 48.0 | 48.0 | |
| Hi | 155 | NR | 77.0 | 70.7 | 69.7 | |
| $CD8_{CT}$ | | | | | | $3.06\ 10^{-7}$ |
| Lo | 180 | 31.3 | 51.1 | 45.4 | 45.4 | |
| Hi | 179 | NR | 78.0 | 72.1 | 71.2 | |
| $CD8_{IM}$ | | | | | | $2.72\ 10^{-4}$ |
| Lo | 157 | 36.0 | 56.3 | 47.7 | 47.7 | |
| Hi | 157 | NR | 74.3 | 70.7 | 69.7 | |
| $CD3_{CT}$ | | | | | | $1.65\ 10^{-6}$ |
| Lo | 179 | 31.3 | 52.0 | 46.7 | 46.7 | |
| Hi | 178 | NR | 78.7 | 71.6 | 70.8 | |
| $CD3_{IM}$ | | | | | | $2.98\ 10^{-8}$ |
| Lo | 177 | 31.1 | 51.8 | 43.6 | 43.6 | |
| Hi | 176 | NR | 79.1 | 75.1 | 74.2 | |
| $GZMB_{CT/IM}$ | | | | | | $5.07\ 10^{-6}$ |
| Lo/Lo | 91 | 23.0 | 46.6 | 40.9 | 40.9 | |
| Het | 93 | NR | 67.2 | 59.2 | 59.2 | |
| Hi/Hi | 86 | NR | 82.1 | 78.7 | 77.0 | |
| $CD45RO_{CT/IM}$ | | | | | | $7.60\ 10^{-4}$ |
| Lo/Lo | 92 | 35.8 | 52.6 | 49.5 | 49.5 | |
| Het | 119 | 100.2 | 63.7 | 54.4 | 54.4 | |
| Hi/Hi | 89 | NR | 81.7 | 77.3 | 75.8 | |
| $CD8_{CT/IM}$ | | | | | | $7.75\ 10^{-7}$ |
| Lo/Lo | 98 | 20.8 | 44.9 | 37.3 | 37.3 | |
| Het | 92 | NR | 67.8 | 61.1 | 61.1 | |
| Hi/Hi | 93 | NR | 79.7 | 75.4 | 73.8 | |
| $CD3_{CT/IM}$ | | | | | | $3.52\ 10^{-9}$ |
| Lo/Lo | 96 | 18.2 | 44.9 | 39.7 | 39.7 | |
| Het | 119 | 68.7 | 62.5 | 53.2 | 53.2 | |
| Hi/Hi | 101 | NR | 87.8 | 84.0 | 82.5 | |

*Log-rank P value for median cut-off
NR: Not Reached,
Het: Hi/Lo and Lo/Hi

TABLE 15

Table S6: Overall survival analyses for all patients according to median cut-offs

| | Overall Survival (OS) for all patients | | | | |
|---|---|---|---|---|---|
| | No. of patients | Median months | Rate at 2 yr % | Rate at 4 yr % | Rate at 5 yr % | P value* |
| $GZMB_{CT}$ | | | | | | $8.18\ 10^{-7}$ |
| Lo | 191 | 42.7 | 62.2 | 47.3 | 40.1 | |
| Hi | 163 | NR | 83.8 | 76.0 | 68.4 | |
| $GZMB_{IM}$ | | | | | | $1.55\ 10^{-2}$ |
| Lo | 152 | 50.8 | 67.4 | 50.7 | 44.3 | |
| Hi | 152 | 100.8 | 77.5 | 68.9 | 58.2 | |
| $CD45RO_{CT}$ | | | | | | $6.92\ 10^{-4}$ |
| Lo | 153 | 46.9 | 65.7 | 49.1 | 43.6 | |
| Hi | 153 | 111.3 | 78.6 | 72.0 | 62.9 | |
| $CD45RO_{IM}$ | | | | | | $1.49\ 10^{-3}$ |
| Lo | 158 | 43.1 | 66.3 | 46.4 | 41.5 | |
| Hi | 155 | 115.0 | 78.6 | 72.8 | 64.6 | |
| $CD8_{CT}$ | | | | | | $2.05\ 10^{-5}$ |
| Lo | 180 | 41.7 | 65.8 | 45.7 | 41.1 | |
| Hi | 179 | NR | 79.6 | 74.9 | 64.8 | |
| $CD8_{IM}$ | | | | | | $2.16\ 10^{-3}$ |
| Lo | 157 | 50.8 | 71.9 | 51.0 | 42.0 | |
| Hi | 157 | NR | 75.3 | 69.5 | 63.2 | |
| $CD3_{CT}$ | | | | | | $7.04\ 10^{-6}$ |
| Lo | 179 | 39.2 | 61.5 | 45.6 | 38.5 | |
| Hi | 178 | 115.1 | 82.5 | 73.7 | 66.1 | |
| $CD3_{IM}$ | | | | | | $9.38\ 10^{-5}$ |
| Lo | 177 | 46.9 | 66.4 | 49.3 | 40.5 | |
| Hi | 176 | NR | 77.0 | 70.5 | 64.2 | |

TABLE 15-continued

Table S6: Overall survival analyses for all patients according to median cut-offs

| | Overall Survival (OS) for all patients | | | | |
|---|---|---|---|---|---|
| | No. of patients | Median months | Rate at 2 yr % | Rate at 4 yr % | Rate at 5 yr % | P value* |
| $GZMB_{CT/IM}$ | | | | | | $2.88 \; 10^{-3}$ |
| Lo/Lo | 92 | 46.9 | 67.4 | 49.6 | 45.4 | |
| Het | 92 | 51.3 | 66.9 | 54.4 | 39.3 | |
| Hi/Hi | 86 | 115.1 | 83.9 | 76.5 | 69.9 | |
| $CD45RO_{CT/IM}$ | | | | | | $7.43 \; 10^{-5}$ |
| Lo/Lo | 92 | 40.3 | 65.2 | 45.3 | 41.0 | |
| Het | 119 | 52.9 | 66.7 | 55.1 | 45.3 | |
| Hi/Hi | 89 | NR | 85.9 | 83.0 | 75.4 | |
| $CD8_{CT/IM}$ | | | | | | $1.04 \; 10^{-4}$ |
| Lo/Lo | 98 | 36.4 | 66.0 | 42.3 | 36.8 | |
| Het | 92 | 59.6 | 72.6 | 58.7 | 46.9 | |
| Hi/Hi | 93 | NR | 80.2 | 77.5 | 70.3 | |
| $CD3_{CT/IM}$ | | | | | | $2.08 \; 10^{-6}$ |
| Lo/Lo | 98 | 35.1 | 60.3 | 41.3 | 31.0 | |
| Het | 119 | 60.0 | 69.7 | 56.7 | 50.5 | |
| Hi/Hi | 101 | NR | 85.4 | 80.6 | 73.0 | |

*Log-rank P value for median cut-off
NR: Not Reached,
Het: Hi/Lo and Lo/Hi

TABLE 16

Table S7: Disease-free survival analyses for UICC-TNM, I, II, III patients, according to the minimum P-value cut-offs

| | Disease-Free Survival (DFS) for UICC-TNM, I, II, III patients | | | | | | |
|---|---|---|---|---|---|---|---|
| | No. of patients | Median months | Rate at 2 yr % | Rate at 4 yr % | Rate at 5 yr % | P value* | P value† | P value‡ |
| $GZMB_{CT}$ | | | | | | $9.17 \; 10^{-1}$ | $3.87 \; 10^{-1}$ | $3.99 \; 10^{-1}$ |
| Lo | 166 | NR | 77.0 | 68.2 | 68.2 | | | |
| Hi | 107 | NR | 87.7 | 83.7 | 83.7 | | | |
| $GZMB_{IM}$ | | | | | | $3.47 \; 10^{-1}$ | $1.51 \; 10^{-1}$ | $1.46 \; 10^{-1}$ |
| Lo | 126 | NR | 74.1 | 68.7 | 68.7 | | | |
| Hi | 112 | NR | 89.1 | 82.5 | 82.5 | | | |
| $CD45RO_{CT}$ | | | | | | $3.58 \; 10^{-3}$ | $2.01 \; 10^{-3}$ | $1.69 \; 10^{-3}$ |
| Lo | 25 | 23.1 | 42.4 | 37.1 | 37.1 | | | |
| Hi | 218 | NR | 84.4 | 77.3 | 77.3 | | | |
| $CD45RO_{IM}$ | | | | | | $3.49 \; 10^{-1}$ | $1.68 \; 10^{-1}$ | $1.73 \; 10^{-1}$ |
| Lo | 121 | NR | 74.2 | 64.4 | 64.4 | | | |
| Hi | 125 | NR | 85.8 | 81.5 | 81.5 | | | |
| $CD8_{CT}$ | | | | | | $5.62 \; 10^{-4}$ | $1.76 \; 10^{-4}$ | $1.58 \; 10^{-4}$ |
| Lo | 85 | 77.6 | 64.1 | 55.7 | 55.7 | | | |
| Hi | 193 | NR | 88.3 | 82.0 | 82.0 | | | |
| $CD8_{IM}$ | | | | | | $2.20 \; 10^{-1}$ | $1.43 \; 10^{-1}$ | $1.81 \; 10^{-1}$ |
| Lo | 138 | NR | 74.0 | 65.5 | 65.5 | | | |
| Hi | 111 | NR | 87.9 | 82.9 | 82.9 | | | |
| $CD3_{CT}$ | | | | | | $1.93 \; 10^{-4}$ | $1.22 \; 10^{-3}$ | $1.16 \; 10^{-3}$ |
| Lo | 69 | 68.7 | 62.6 | 53.8 | 53.8 | | | |
| Hi | 209 | NR | 87.9 | 80.9 | 80.9 | | | |
| $CD3_{IM}$ | | | | | | $4.78 \; 10^{-6}$ | $6.23 \; 10^{-6}$ | $6.32 \; 10^{-6}$ |
| Lo | 103 | NR | 72.0 | 60.5 | 60.5 | | | |
| Hi | 171 | NR | 88.1 | 83.3 | 83.3 | | | |
| $GZMB_{CT/IM}$ | | | | | | $7.81 \; 10^{-1}$ | $3.33 \; 10^{-1}$ | $3.42 \; 10^{-1}$ |
| Lo/Lo | 87 | NR | 70.4 | 64.3 | 64.3 | | | |
| Het | 69 | NR | 81.7 | 73.2 | 73.2 | | | |
| Hi/Hi | 58 | NR | 90.8 | 85.9 | 85.9 | | | |
| $CD45RO_{CT/IM}$ | | | | | | $1.45 \; 10^{-2}$ | $4.04 \; 10^{-2}$ | $4.14 \; 10^{-2}$ |
| Lo/Lo | 16 | 20.1 | 40.2 | 40.2 | 40.2 | | | |
| Het | 110 | NR | 76.8 | 64.8 | 64.8 | | | |
| Hi/Hi | 112 | NR | 88.3 | 85.9 | 85.9 | | | |
| $CD8_{CT/IM}$ | | | | | | $1.94 \; 10^{-3}$ | $3.52 \; 10^{-3}$ | $3.84 \; 10^{-3}$ |
| Lo/Lo | 61 | 35.8 | 59.0 | 48.9 | 48.9 | | | |
| Het | 76 | NR | 82.2 | 76.2 | 76.2 | | | |
| Hi/Hi | 87 | NR | 87.8 | 81.6 | 81.6 | | | |
| $CD3_{CT/IM}$ | | | | | | $8.57 \; 10^{-7}$ | $2.49 \; 10^{-4}$ | $2.93 \; 10^{-4}$ |
| Lo/Lo | 30 | 23.1 | 49.9 | 38.0 | 38.0 | | | |
| Het | 95 | NR | 76.4 | 65.6 | 65.6 | | | |
| Hi/Hi | 124 | NR | 91.0 | 87.1 | 87.1 | | | |

*Log-rank P value corrected (Allman et al. 1994),
†P value median 100 * CV Log-rank
‡p value median 100 * CV stratified Log-rank
NR: Not Reached,
Het: Hi/Lo and Lo/Hi

TABLE 17

Table S8: Overall survival analyses for UICC-TNM, I, II, III patients, according to the minimum P-value cut-offs Overall Survival (OS) for UICC-TNM, I, II, III patients

| | No. of patients | Median months | Rate at 2 yr % | Rate at 4 yr % | Rate at 5 yr % | P value* | P value† | P value‡ |
|---|---|---|---|---|---|---|---|---|
| $GZMB_{CT}$ | | | | | | $1.52\ 10^{-1}$ | $1.13\ 10^{-1}$ | $8.16\ 10^{-2}$ |
| Lo | 168 | 89.0 | 83.5 | 69.2 | 61.1 | | | |
| Hi | 107 | NR | 85.9 | 79.7 | 71.8 | | | |
| $GZMB_{IM}$ | | | | | | $5.38\ 10^{-1}$ | $7.30\ 10^{-1}$ | $7.16\ 10^{-1}$ |
| Lo | 126 | 101.0 | 81.7 | 69.1 | 61.8 | | | |
| Hi | 112 | 115.0 | 85.6 | 76.2 | 64.5 | | | |
| $CD45RO_{CT}$ | | | | | | $2.53\ 10^{-4}$ | $2.92\ 10^{-3}$ | $2.25\ 10^{-3}$ |
| Lo | 25 | 43.0 | 69.7 | 41.8 | 32.5 | | | |
| Hi | 218 | NR | 83.9 | 75.4 | 67.8 | | | |
| $CD45RO_{IM}$ | | | | | | $1.22\ 10^{-1}$ | $3.86\ 10^{-1}$ | $4.33\ 10^{-1}$ |
| Lo | 121 | 101.0 | 80.1 | 64.2 | 56.5 | | | |
| Hi | 125 | NR | 84.3 | 79.4 | 70.6 | | | |
| $CD8_{CT}$ | | | | | | $6.00\ 10^{-5}$ | $1.09\ 10^{-4}$ | $1.03\ 10^{-4}$ |
| Lo | 85 | 65.3 | 74.8 | 56.1 | 50.2 | | | |
| Hi | 193 | NR | 88.2 | 81 | 71.8 | | | |
| $CD8_{IM}$ | | | | | | $3.03\ 10^{-2}$ | $4.32\ 10^{-1}$ | $4.20\ 10^{-1}$ |
| Lo | 138 | 76.1 | 82.4 | 66.3 | 57 | | | |
| Hi | 111 | NR | 86.8 | 81.2 | 73.7 | | | |
| $CD3_{CT}$ | | | | | | $2.51\ 10^{-7}$ | $1.65\ 10^{-5}$ | $1.47\ 10^{-5}$ |
| Lo | 69 | 35.5 | 69.5 | 47.6 | 40.1 | | | |
| Hi | 209 | NR | 88.5 | 81.4 | 73.2 | | | |
| $CD3_{IM}$ | | | | | | $7.35\ 10^{-3}$ | $7.61\ 10^{-2}$ | $6.25\ 10^{-2}$ |
| Lo | 103 | 69.3 | 80.7 | 65 | 53.7 | | | |
| Hi | 171 | NR | 85.9 | 78.7 | 71.7 | | | |
| $GZMB_{CT/IM}$ | | | | | | $8.29\ 10^{-2}$ | $5.30\ 10^{-1}$ | $4.99\ 10^{-1}$ |
| Lo/Lo | 87 | NR | 83.2 | 69.2 | 63.3 | | | |
| Het | 69 | 69.3 | 80.8 | 67.7 | 51.8 | | | |
| Hi/Hi | 58 | NR | 85.6 | 79.2 | 71.8 | | | |
| $CD45RO_{CT/IM}$ | | | | | | $1.02\ 10^{-2}$ | $4.39\ 10^{-2}$ | $3.72\ 10^{-2}$ |
| Lo/Lo | 16 | 43.0 | 73.1 | 36.5 | 36.5 | | | |
| Het | 110 | 87.3 | 80.1 | 67.3 | 56.3 | | | |
| Hi/Hi | 112 | NR | 85.3 | 80.8 | 74.8 | | | |
| $CD8_{CT/IM}$ | | | | | | $7.02\ 10^{-4}$ | $1.60\ 10^{-2}$ | $1.96\ 10^{-2}$ |
| Lo/Lo | 61 | 56.2 | 72.7 | 52.2 | 45.3 | | | |
| Het | 76 | 111.4 | 88.6 | 77.3 | 65.1 | | | |
| Hi/Hi | 87 | NR | 86.7 | 81.1 | 73.6 | | | |
| $CD3_{CT/IM}$ | | | | | | $2.90\ 10^{-6}$ | $2.72\ 10^{-4}$ | $1.21\ 10^{-4}$ |
| Lo/Lo | 30 | 35.5 | 71.4 | 43.4 | 32.8 | | | |
| Het | 95 | 72.1 | 76.6 | 64.6 | 54.8 | | | |
| Hi/Hi | 124 | NR | 90.8 | 85.9 | 78.6 | | | |

*Log-rank P value,
†P value median 100 * CV Log-rank
‡P value median 100 * CV stratified Log-rank
NR: Not Reached,
Het: Hi/Lo end Lo/Hi

TABLE 18

Table S9: DFS analyses for UICC-TNM, I, II, III patients according to median cut-offs Disease-Free Survival (DFS) for UICC-TNM, I, II, III patients

| | No. of patients | Median months | Rate at 2 yr % | Rate at 4 yr % | Rate at 5 yr % | P value* |
|---|---|---|---|---|---|---|
| $GZMB_{CT}$ | | | | | | $8.07\ 10^{-2}$ |
| Lo | 140 | NR | 77.8 | 68.1 | 68.1 | |
| Hi | 133 | NR | 84.8 | 80.6 | 80.6 | |
| $GZMB_{IM}$ | | | | | | $2.26\ 10^{-2}$ |
| Lo | 119 | NR | 74.7 | 69.1 | 69.1 | |
| Hi | 119 | NR | 87.9 | 81.5 | 81.5 | |
| $CD45RO_{CT}$ | | | | | | $2.27\ 10^{-1}$ |
| Lo | 122 | NR | 76.5 | 70.7 | 70.7 | |
| Hi | 121 | NR | 84.1 | 75.9 | 75.9 | |
| $CD45RO_{IM}$ | | | | | | $1.96\ 10^{-2}$ |
| Lo | 124 | NR | 74.6 | 65.1 | 65.1 | |
| Hi | 122 | NR | 85.6 | 81.1 | 81.1 | |
| $CD8_{CT}$ | | | | | | $6.53\ 10^{-4}$ |
| Lo | 139 | NR | 73.3 | 65.1 | 65.1 | |
| Hi | 139 | NR | 89.4 | 83.9 | 83.9 | |
| $CD8_{IM}$ | | | | | | $3.99\ 10^{-2}$ |
| Lo | 125 | NR | 75.9 | 66.5 | 66.5 | |
| Hi | 124 | NR | 84.7 | 80.1 | 80.1 | |
| $CD3_{CT}$ | | | | | | $4.48\ 10^{-4}$ |
| Lo | 139 | NR | 72.6 | 66.1 | 66.1 | |

TABLE 18-continued

Table S9: DFS analyses for UICC-TNM, I, II, III patients according to median cut-offs

| | | Disease-Free Survival (DFS) for UICC-TNM, I, II, III patients | | | |
|---|---|---|---|---|---|
| | No. of patients | Median months | Rate at 2 yr % | Rate at 4 yr % | Rate at 5 yr % | P value* |

TABLE 18-continued

Table S9: DFS analyses for UICC-TNM, I, II, III patients according to median cut-offs

| | No. of patients | Median months | Rate at 2 yr % | Rate at 4 yr % | Rate at 5 yr % | P value* |
|---|---|---|---|---|---|---|
| $CD3_{IM}$ | | | | | | $4.42\ 10^{-4}$ |
| Lo | 138 | NR | 74.4 | 65.4 | 65.4 | |
| Hi | 136 | NR | 90.1 | 84.9 | 84.9 | |
| $GZMB_{CT/IM}$ | | | | | | $5.63\ 10^{-2}$ |
| Lo/Lo | 72 | NR | 69.4 | 61.9 | 61.9 | |
| Het | 74 | NR | 85.6 | 77.8 | 77.8 | |
| Hi/Hi | 66 | NR | 84.1 | 79.8 | 79.8 | |
| $CD45RO_{CT/IM}$ | | | | | | $6.94\ 10^{-2}$ |
| Lo/Lo | 71 | NR | 72.9 | 67.0 | 67.0 | |
| Het | 100 | NR | 79.4 | 68.9 | 68.9 | |
| Hi/Hi | 67 | NR | 87.6 | 85.6 | 85.6 | |
| $CD8_{CT/IM}$ | | | | | | $3.36\ 10^{-3}$ |
| Lo/Lo | 80 | 100.3 | 66.8 | 57.8 | 57.8 | |
| Het | 65 | NR | 82.9 | 75.6 | 75.6 | |
| Hi/Hi | 79 | NR | 86.4 | 81.3 | 81.3 | |
| $CD3_{CT/IM}$ | | | | | | $6.20\ 10^{-5}$ |
| Lo/Lo | 73 | 100.3 | 65.4 | 58.8 | 58.8 | |
| Het | 102 | NR | 82.4 | 73.1 | 73.1 | |
| Hi/Hi | 74 | NR | 94.2 | 89.1 | 89.1 | |

*Log-rank P value for median cut-off
NR: Not Reached, Het: Hi/Lo and Lo/Hi

TABLE 19

Table S10: OS analyses for UICC-TNM, I, II, III patients according to median cut-offs

| | No. of patients | Median months | Rate at 2 yr % | Rate at 4 yr % | Rate at 5 yr % | P value* |
|---|---|---|---|---|---|---|
| $GZMB_{CT}$ | | | | | | $5.06\ 10^{-2}$ |
| Lo | 140 | 27.1 | 81.2 | 66.7 | 59.0 | |
| Hi | 133 | NR | 87.8 | 80.0 | 71.5 | |
| $GZMB_{IM}$ | | | | | | $7.28\ 10^{-1}$ |
| Lo | 119 | 30.4 | 83.3 | 70.2 | 62.5 | |
| Hi | 119 | 115.1 | 83.7 | 74.8 | 63.7 | |
| $CD45RO_{CT}$ | | | | | | $2.13\ 10^{-2}$ |
| Lo | 122 | 21.4 | 79.0 | 63.5 | 57.1 | |
| Hi | 121 | NR | 86.0 | 80.8 | 71.4 | |
| $CD45RO_{IM}$ | | | | | | $1.31\ 10^{-1}$ |
| Lo | 124 | 21.4 | 79.8 | 64.3 | 56.8 | |
| Hi | 122 | NR | 84.7 | 79.7 | 70.8 | |
| $CD8_{CT}$ | | | | | | $8.49\ 10^{-3}$ |
| Lo | 139 | 24.8 | 82.5 | 63.9 | 55.7 | |
| Hi | 139 | NR | 85.9 | 82.9 | 74.6 | |
| $CD8_{IM}$ | | | | | | $7.20\ 10^{-2}$ |
| Lo | 125 | 30.0 | 84.2 | 67.6 | 57.3 | |
| Hi | 124 | NR | 84.6 | 78.5 | 71.8 | |
| $CD3_{CT}$ | | | | | | $9.15\ 10^{-3}$ |
| Lo | 139 | 18.9 | 78.0 | 62.5 | 54.8 | |
| Hi | 139 | NR | 89.4 | 83.0 | 74.6 | |

TABLE 19-continued

Table S10: OS analyses for UICC-TNM, I, II, III patients according to median cut-offs

| | No. of patients | Median months | Rate at 2 yr % | Rate at 4 yr % | Rate at 5 yr % | P value* |
|---|---|---|---|---|---|---|
| $CD3_{IM}$ | | | | | | $2.80\ 10^{-2}$ |
| Lo | 138 | 26.0 | 82.7 | 67.1 | 58.7 | |
| Hi | 136 | NR | 85.3 | 80.5 | 72.3 | |
| $GZMB_{CT/IM}$ | | | | | | $6.09\ 10^{-1}$ |
| Lo/Lo | 72 | 111.4 | 82.6 | 66.9 | 63.3 | |
| Het | 74 | 76.1 | 82.3 | 72.3 | 54.7 | |
| Hi/Hi | 68 | 115.1 | 84.5 | 75.5 | 69.2 | |
| $CD45RO_{CT/IM}$ | | | | | | $2.48\ 10^{-2}$ |
| Lo/Lo | 71 | 67.3 | 78.4 | 69.2 | 55.8 | |
| Het | 100 | 74.2 | 81.1 | 71.1 | 58.1 | |
| Hi/Hi | 67 | NR | 87.7 | 85.7 | 79.9 | |
| $CD8_{CT/IM}$ | | | | | | $1.56\ 10^{-2}$ |
| Lo/Lo | 80 | 59.6 | 79.3 | 60.4 | 49.6 | |
| Het | 65 | NR | 88.5 | 73.4 | 64.1 | |
| Hi/Hi | 79 | NR | 83.7 | 82.2 | 75.5 | |
| $CD3_{CT/IM}$ | | | | | | $5.35\ 10^{-3}$ |
| Lo/Lo | 73 | 59.6 | 76.0 | 57.1 | 48.4 | |
| Het | 102 | 78.8 | 82.9 | 73.6 | 65.0 | |
| Hi/Hi | 74 | NR | 90.3 | 87.1 | 78.8 | |

*Log-rank P value for median cut-off
NR: Not Reached, Het: Hi/Lo and Lo/Hi

TABLE 20

Table S11a: Multivariate proportional hazard Cox analysis for DFS

| Variable | Hazard ratio | 95% CI | P value |
|---|---|---|---|
| T-stage | 1.574 | (1.09-2.26) | 0.02 |
| N-stage‡ | 1.398 | (0.83-2.36) | 0.21 |
| Differentiation | 0.77 | (0.42-1.43) | 0.41 |
| $CD3_{CT}/CD3_{IM}$ patterns | 2.391* | (1.68-3.41)* | $1.4\ 10^{-6}$ |
| | 2.379† | (1.67-3.39)† | |

*Minimum P-value cut-off with 3 groups (HiHi, LoLo, Het)
†Leave-one-out method, correction using $C = 1 - (SE[coef]/coef)^2 = 0.9573126$ (heuristic shrinkage factor, Holländer et al). Similar results obtained using bootstrap
‡Note:
N violates the proportional hazards assumption. A model stratifying by this factor was performed and $CD3_{CT}/CD3_{IM}$ remained an independent prognostic factor for disease free survival. P-values from the stratified model: T = 0.01; Diff = 0.32; $CD3_{CT}/CD3_{IM} = 9.4 \times 10^{-7}$
HR from the stratified model: T = 1.572(1.10-2.25);
Diff = 0.728 (0.39-1.37); $CD3_{CT}/CD3_{IM} = 2.451(1.71-3.51)$. Shrinkage factor: c = 0.9583

Table S11b: Multivariate proportional hazard Cox analysis for DFS

| Variable | Hazard ratio | 95% CI | P value |
|---|---|---|---|
| T-stage | 1.370 | (0.86-2.19) | 0.19 |
| N-stage‡ | 1.210 | (0.60-2.47) | 0.59 |
| Differentiation | 1.020 | (0.50-2.08) | 0.97 |

TABLE 20-continued

| | | | |
|---|---|---|---|
| $CD3_{CT}/CD3_{IM}$ patterns | 6.200* | (2.96-12.99)* | $1.3\ 10^{-6}$ |
| | 5.940† | (2.83-12.43)† | |

*Minimum P-value cut-off with 3 groups (HiHi, LoLo)
†Leave-one-out method, correction using C = 1 -(SE[coef]/coef)$^2$ = 0.9573126 (heuristic shrinkage factor, Holländer et al). Similar results obtained using bootstrap
‡Note:
N violates the proportional hazards assumption. A model stratifying by this factor was performed and $CD3_{CT}/CD3_{IM}$ remained an independent prognostic factor for disease free survival. P-values from the stratified model: T = 0.02; Diff = 0.97; $CD3_{CT}/CD3_{IM} = 1.3 \times 10^{-6}$.
HR from the stratified model: T = 1.408(0.88-2.26); Diff = 0.986(0.48-2.02); $CD3_{CT}/CD3_{IM}$ = 6.322(2.99-13.35). Shrinkage factor: c = 0.9573

Table S11c: Multivariate proportional hazard Cox analysis for DFS UICC-TNM, I, II, III patients according to median cut-off

| Variable* | Hazard ratio | 95% CI | P value |
|---|---|---|---|
| T-stage | 1.560 | (1.074-2.26) | 0.02 |
| N-stage | 1.490 | (0.882-2.53) | 0.14 |
| Differentiation | 1.290 | (0.682-2.45) | 0.43 |
| $CD3_{CT}/CD3_{IM}$ patterns§ | 1.870 | (1.311-2.66) | $5.5\ 10^{4}$ |

§cut-off at the median, with 3 groups (HiHi, LoLo, Het)

Table S11d: Multivariate proportional hazard Cox analysis for DFS UICC-TNM, I, II, III patients according to median cut-off

| Variable* | Hazard ratio | 95% CI | P value |
|---|---|---|---|
| T-stage | 1.484 | (0.361-6.10) | 0.58 |
| N-stage | 2.065 | (0.736-5.80) | 0.17 |
| Differentiation | 1.532 | (0.571-4.11) | 0.40 |
| $CD3_{CT}/CD3_{IM}$ patterns§ | 4.626 | (1.736-12.33) | $2.2\ 10^{3}$ |

§cut-off at the median, with 2 groups (HiHi, LoLo)

TABLE 21

Table S12a: Multivariate proportional hazard Cox analysis for OS

| Variable | Hazard ratio | 95% CI | P value |
|---|---|---|---|
| T-stage | 1.170 | (0.90-1.52) | 0.25 |
| N-stage | 1.370 | (0.90-2.11) | 0.15 |
| Differentiation | 1.050 | (0.68-1.62) | 0.84 |
| $CD3_{CT}/CD3_{IM}$ patterns* | 1.890 | (1.42-2.51) | $1.2\ 10^{-5}$ |

*Minimum P-value cut-off with 3 groups (HiHi, LoLo, Het)

Table S12b: Multivariate proportional hazard Cox analysis for OS

| Variable | Hazard ratio | 95% CI | P value |
|---|---|---|---|
| T-stage | 0.980 | (0.69-1.39) | 0.91 |
| N-stage | 1.370 | (0.75-2.52) | 0.31 |
| Differentiation | 1.590 | (0.97-2.61) | 0.07 |
| $CD3_{CT}/CD3_{IM}$ patterns* | 3.710 | (1.97-6.97) | $4.7\ 10^{-5}$ |

*Minimum P-value cut-off, with 2 groups (HiHi, LoLo)

Table S12c: Multivariate proportional hazard Cox analysis for OS in UICC-TNM, I, II, III patients according to median cut-off

| Variable | Hazard ratio | 95% CI | P value |
|---|---|---|---|
| T-stage | 1.200 | (0.912-1.57) | 0.20 |
| N-stage | 1.450 | (0.940-2.22) | 0.09 |
| Differentiation | 1.080 | (0.689-1.68) | 0.75 |
| $CD3_{CT}/CD3_{IM}$ patterns§ | 1.460 | (1.107-1.92) | $7.2\ 10^{-3}$ |

§cut-off at the median, with 3 groups (HiHi, LoLo, Het)

Table S12d: Multivariate proportional hazard Cox analysis for OS in UICC-TNM, I, II, III patients according to median cut-off

| Variable | Hazard ratio | 95% CI | P value |
|---|---|---|---|
| T-stage | 1.160 | (0.818-1.66) | 0.40 |
| N-stage | 1.240 | (0.696-2.19) | 0.47 |
| Differentiation | 1.480 | (0.892-2.45) | 0.13 |
| $CD3_{CT}/CD3_{IM}$ patterns§ | 2.200 | (1.219-3.97) | $8.8\ 10^{-3}$ |

§cut-off at the median, with 2 groups (HiHi, LoLo)

The invention claimed is:

1. An in vitro method for the prognosis of survival time of a patient suffering from cancer, which method comprises the following steps:
    a) removing one or more pieces or slices of tissue from a tumor, wherein said one or more pieces or slices of tissue include either or both tumor center (CT) tissue from the center of the tumor and invasive margin (IM) tissue from the invasive margin of the tumor, said removing step obtaining both said CT tissue and said IM tissue;
    b) separately quantifying for said CT tissue and for said IM tissue in said one or more pieces or slices, cell densities of each of at least two types of cells selected from the group consisting of CD45RO cells, CD8 cells, CD3 cells and Granzyme B (GZMB) cells, wherein said step of quantifying includes the step of binding antibodies specifically to biological markers expressed by said at least two types of cells;
    c) providing predetermined cut-off reference values for cell densities of CD3, CD8, CD45RO, and GZMB cells in CT and IM tumor tissue samples, wherein said predetermined cut-off reference values are correlated with a specific prognosis of survival time;
    d) comparing cell density quantification values obtained at step b) with corresponding predetermined cut-off reference values selected from the predetermined cut-off reference values provided in step c, and and
    e) determining a prognosis for said patient, wherein
    a favorable prognosis of survival time is provided for said patient when the quantification values for said cell densities of each of said at least two types of cells are, in both said CT tumor tissue and in said IM tumor tissue, higher than said corresponding predetermined cut-off reference values; and wherein
    a poor prognosis of survival time is provided for said patient when the quantification values for said cell densities of each of said at least two types of cells are, in both said CT tumor tissue and in said IM tumor tissue, lower than said corresponding predetermined cut-off reference values.

2. The method of claim 1, wherein said step of providing cut-off reference values is performed by
    a) selecting a biological marker for which a reference value is to be determined;
    b) providing a collection of tumor tissue samples from cancer patients by removing one or more pieces or slices of tissue from the tumor, wherein said one or more pieces or slices of tissue include tumor center (CT) tissue from the center of the tumor and invasive margin (IM) tissue from the invasive margin of the tumor;
    c) providing, for each tumor sample provided at step b), information relating to the actual clinical outcome for the corresponding cancer patient;

d) providing a series of arbitrary quantification values for the biological marker selected at step a);
e) quantifying the biological marker in each tumor tissue sample contained in the collection provided at step b);
f) classifying the tumor samples in two groups for one specific arbitrary quantification value provided at step c), wherein: (i) a first group comprising tumor samples that exhibit a quantification value for the biological marker that is lower than the arbitrary quantification value contained in the serial of quantification values; and (ii) a second group comprising tumor samples that exhibit a quantification value for the biological marker that is higher than the arbitrary quantification value contained in the serial of quantification values; whereby two groups of tumor samples are obtained for the specific quantification value, and wherein the tumors samples of each group are separately enumerated;
g) calculating the statistical significance between (i) the quantification value for the biological marker obtained at step e) and (ii) the actual clinical outcome of the patients from which tumor samples contained in the first and second groups defined at step f) derive;
h) reiterating steps f) and g) until every arbitrary quantification value provided, at step d) is tested;
i) setting said cut-off reference value as consisting of the arbitrary quantification value for which the highest statistical significance has been calculated at step g).

3. The in vitro method according to claim 1, wherein the cancer is colorectal cancer.

4. The in vitro method according to claim 1, wherein the survival time is disease-free survival (DFS).

5. The in vitro method according to claim 1, wherein the survival time is overall survival (OS).

6. The in vitro method according to claim 1, wherein said at least two types of cells include CD45RO cells.

7. The in vitro method according to claim 1, wherein said at least two types of cells include CD8 cells.

8. The in vitro method according to claim 1, wherein said at least two types of cells includes CD3 cells.

9. The in vitro method according to claim 1, wherein said at least two types of cells includes GZMB cells.

10. The in vitro method according to claim 1, further comprising the step of carrying out Tumor-Node-Metastasis (TNM) classification for said patient and providing said TMN classification with said prognosis.

11. The in vitro method according to claim 1, further comprising providing an intermediate prognosis of survival time for said patient when a quantification value for cell density of one or more of the at least two types of cells that are tested is higher than predetermined reference values for cell density and a quantification value for cell density for one or more of the remaining at least two types of cells that are tested is lower than a predetermined reference value.

12. The in vitro method according to claim 1, wherein cell densities of at least three types of cells are quantified.

13. The in vitro method according to claim 1, wherein said at least two types of cells are CD3 cells and CD8 cells.

14. The in vitro method according to claim 1, wherein said at least two types of cells are CD3 cells and CD45RO cells.

15. The in vitro method according to claim 1, wherein said at least two types of cells are CD8 cells and CD45RO cells.

16. The method of claim 1, further comprising the step of identifying said patient as being at high risk for recurrence of said cancer and likely to benefit from adjuvant therapy when said step of comparing results in provision of a poor prognosis for said patient.

17. The method of claim 1, wherein
i) said method is carried out prior to administering an anticancer agent in order to provide a pre-administration prognosis of survival time; and
ii) said method is carried out after administering said anticancer agent in order to provide a post-administration prognosis of survival time;
and wherein said method further comprises a step of determining the effectiveness of said anticancer agent by comparing said pre-administration prognosis of survival time with said post-administration prognosis of survival time,
wherein
if said post-administration prognosis of survival time is improved compared to said pre-administration prognosis of survival time, then said anticancer agent is determined to be effective,
and if said post-administration prognosis of survival time is not improved compared to said pre-administration prognosis of survival time, then said anticancer agent is determined to be ineffective.

18. An in vitro method for the prognosis of survival time of a patient suffering from cancer, which method comprises the following steps:
a) removing one or more pieces or slices of tissue from a tumor, wherein said one or more pieces or slices of tissue include either or both tumor center (CT) tissue from the center of the tumor and invasive margin (IM) tissue from the invasive margin of the tumor, said removing step obtaining both said CT tissue and said IM tissue;
b) separately quantifying for said CT tissue and for said IM tissue in said one or more pieces or slices, cell densities of each of at least two types of cells selected from the group consisting of CD45RO cells, CD3 cells and Granzyme B (GZMB) cells, wherein said step of quantifying includes the step of binding antibodies specifically to biological markers expressed by said at least two types of cells;
c) providing predetermined cut-off reference values for cell densities of CD45RO, CD3, and GZMB cells in CT and IM tumor tissue samples, wherein said predetermined cut-off reference values are correlated with a specific prognosis of survival time;
d) comparing cell density quantification values obtained at step b) with corresponding predetermined cut-off reference values selected from the predetermined cut-off reference values provided in step c, and and
e) determining a prognosis for said patient, wherein
a favorable prognosis of survival time is provided for said patient when the quantification values for said cell densities of each of said at least two types of cells are, in both said CT tumor tissue and in said IM tumor tissue, higher than said corresponding predetermined cut-off reference values; and wherein
a poor prognosis of survival time is provided for said patient when the quantification values for said cell densities of each of said at least two types of cells are, in both said CT tumor tissue and in said IM tumor tissue, lower than said corresponding predetermined cut-off reference values.

19. The method of claim 18, wherein said step of providing cut-off reference values is performed by
a) selecting a biological marker for which a reference value is to be determined;
b) providing a collection of tumor tissue samples from cancer patients by removing one or more pieces or slices of tissue from the tumor, wherein said one or more pieces or slices of tissue include tumor center (CT) tissue from the center of the tumor and invasive margin (IM) tissue from the invasive margin of the tumor; , c) providing, for each tumor sample provided at step b), information relating to the actual clinical outcome for the corresponding cancer patient;

d) providing a series of arbitrary quantification values for the biological marker selected at step a);

e) quantifying the biological marker in each tumor tissue sample contained in the collection provided at step b);

f) classifying the tumor samples in two groups for one specific arbitrary quantification value provided at step c), wherein: (i) a first group comprising tumor samples that exhibit a quantification value for the biological marker that is lower than the arbitrary quantification value contained in the serial of quantification values; and (ii) a second group comprising tumor samples that exhibit a quantification value for the biological marker that is higher than the arbitrary quantification value contained in the serial of quantification values; whereby two groups of tumor samples are obtained for the specific quantification value, and wherein the tumors samples of each group are separately enumerated;

g) calculating the statistical significance between (i) the quantification value for the biological marker obtained at step e) and (ii) the actual clinical outcome of the patients from which tumor samples contained in the first and second groups defined at step f) derive;

h) reiterating steps f) and g) until every arbitrary quantification value provided, at step d) is tested;

i) setting the said cut-off reference value as consisting of the arbitrary quantification value for which the highest statistical significance is been calculated at step g).

20. The in vitro method according to claim 19, wherein cell densities of at least three types of cells are quantified.

21. The in vitro method according to claim 18, wherein the cancer is colorectal cancer.

22. The in vitro method according to claim 18, wherein the survival time is disease-free survival (DFS).

23. The in vitro method according to claim 18, wherein the survival time is overall survival (OS).

24. The in vitro method according to claim 18, wherein said at least one type of cell includes CD45RO cells.

25. The in vitro method according to claim 18, wherein said at least one type of cell includes CD3 cells.

26. The in vitro method according to claim 18, wherein said at least one type of cell includes GZMB cells.

27. The in vitro method according to claim 18, further comprising the step of carrying out Tumor-Node-Metastasis (TNM) classification for said patient and providing said TMN classification with said prognosis.

28. The in vitro method according to claim 18, further comprising
performing steps a)-e) for a plurality of cell types and
providing an intermediate prognosis of survival time for said patient when a quantification value for cell density of at least one of the plurality of cell types is higher than a predetermined reference value for cell density and a quantification value for cell density for at least one of the remaining cell types tested is lower than a predetermined reference value.

29. The in vitro method according to claim 18, wherein cell densities of at least two types of cells are quantified.

30. The in vitro method according to claim 18, further comprising the steps of:
quantifying, in said at least two tumor tissue samples from said patient, a cell density of CD8 cells;
comparing quantification values for CD8 cells obtained in said quantifying step with predetermined reference values for CD8 cells; and
providing a favorable prognosis of survival time for said patient when said quantification values for CD8 cells are higher than said predetermined reference values for CD8 cells or
providing a poor prognosis of survival time for said patient when said quantification values for CD8 cells are lower than said predetermined reference values for CD8 cells.

31. The method of claim 18, further comprising the step of identifying said patient as being at high risk for recurrence for said cancer and likely to benefit from adjuvant therapy when said step of comparing results in provision of a poor prognosis for said patient.

32. The method of claim 18, wherein
i) said method is carried out prior to administering an anticancer agent in order to provide a pre-administration prognosis of survival time; and
ii) at least a second pair of said at least four tumor tissue samples is obtained after administering said anticancer agent in order to provide a post-administration prognosis of survival time; and wherein said method further comprises a step of
determining the effectiveness of said anticancer agent by comparing said pre-administration prognosis of survival time with said post-administration prognosis of survival time,
wherein
if said post-administration prognosis of survival time is improved compared to said pre-administration prognosis of survival time, then said anticancer agent is determined to be effective,
and if said post-administration prognosis of survival time is not improved compared to said pre-administration prognosis of survival time, then said anticancer agent is determined to be ineffective.

33. An in vitro method for the prognosis of survival time of a patient suffering from cancer, which method comprises the following steps:
a) removing one or more pieces or slices of tissue from a tumor, wherein said one or more pieces or slices of tissue include either or both tumor center (CT) tissue from the center of the tumor and invasive margin (IM) tissue from the invasive margin of the tumor, said removing step obtaining both said CT tissue and said IM tissue;
b) separately quantifying for said CT tissue and for said IM tissue in said one or more pieces or slices, cell densities of each of CD45RO cells, CD8 cells, CD3 cells and Granzyme B (GZMB) cells, wherein said step of quantifying includes the step of binding antibodies specifically to biological markers expressed by said cells;
c) providing predetermined cut-off reference values for CT and IM tumor tissue sample cell densities for CD3, CD8, CD45RO, and GZMB cells, wherein said predetermined cut-off reference values are correlated with a specific prognosis of survival time;
d) comparing quantification values obtained at step b) for said cell densities of said CD3, CD8, CD45RO, and GZMB cells in said CT tumor tissue sample with said predetermined cut-off reference values for CD3, CD8, CD45RO, and GZMB cell densities in CT tumor tissue samples, and
e) comparing quantification values obtained at step b) for said cell densities of said CD3, CD8, CD45RO, and GZMB cells in said IM tumor tissue sample with said predetermined cut-off reference values for CD3, CD8, CD45RO, and GZMB cell densities in IM tumor tissue samples; and f) determining a prognosis for said patient, wherein a favorable prognosis of survival time is provided for said patient when the quantification values for said cell densities of said CD3, CD8, CD45RO, and GZMB cells in said CT tumor tissue sample are higher than said predetermined cut-off reference values for CD3, CD8, CD45RO, and GZMB cell densities in CT tumor tissue samples, and said quantification values for said cell densities of said CD3, CD8, CD45RO, and GZMB cells in said IM tumor tissue sample are higher than said predetermined cut-off reference values for CD3, CD8, CD45RO, and GZMB cell densities in IM tumor tissue samples; and wherein a poor prognosis of survival time is provided for said patient when the quantification values for said cell densities of said CD3, CD8, CD45RO, and GZMB cells in said CT tumor tissue sample are lower than said predetermined cut-off reference values for CD3, CD8, CD45RO, and GZMB cell densities in CT tumor tissue samples, and said quantification values for said cell densities of CD3, CD8, CD45RO, and GZMB cells in said IM tumor tissue sample are lower than said predetermined cut-off reference values for CD3, CD8, CD45RO, and GZMB cell densities in IM tumor tissue samples.

* * * * *

UNITED STATES PATENT AND TRADEMARK OFFICE
CERTIFICATE OF CORRECTION

PATENT NO. : 8,481,271 B2  
APPLICATION NO. : 12/090832  
DATED : July 9, 2013  
INVENTOR(S) : J. Galon et al.

It is certified that error appears in the above-identified patent and that said Letters Patent is hereby corrected as shown below:

On the title page, item (54) and in the specification, column 1, line 1, delete current title and insert corrected title --IN VITRO METHOD FOR THE PROGNOSIS OF PROGRESSION OF A CANCER AND OF THE OUTCOME IN A PATIENT AND MEANS FOR PERFORMING SAID METHOD--

Signed and Sealed this  
Third Day of September, 2013

Teresa Stanek Rea  
*Acting Director of the United States Patent and Trademark Office*